(12) United States Patent
Xiao et al.

(10) Patent No.: US 9,550,781 B2
(45) Date of Patent: Jan. 24, 2017

(54) KINASE MODULATING COMPOUNDS, COMPOSITIONS CONTAINING THE SAME AND USE THEREOF

(71) Applicants: CENTAURUS BIOPHARMA CO., LTD., Beijing (CN); CHIA TAI TIANQING PHARMACEUTICAL GROUP CO., LTD, Lianyungang (CN)

(72) Inventors: Dengming Xiao, Beijing (CN); Jijun Li, Beijing (CN); Yan Zhu, Beijing (CN); Yuandong Hu, Beijing (CN); Huting Wang, Beijing (CN); Zhe Wang, Beijing (CN); Zanping Wang, Beijing (CN); Yongheng Wei, Beijing (CN); Yinghui Sun, Beijing (CN); Qiong Wu, Beijing (CN); Hui Zhang, Beijing (CN); Yong Peng, Beijing (CN); Fansheng Kong, Beijing (CN); Ying Sun, Beijing (CN); Hong Luo, Beijing (CN); Yongxin Han, Beijing (CN)

(73) Assignees: Centaurus Biopharma Co., Ltd., Beijing (CN); Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 47 days.

(21) Appl. No.: 13/261,878

(22) PCT Filed: Nov. 14, 2012

(86) PCT No.: PCT/CN2012/084595
§ 371 (c)(1),
(2) Date: May 14, 2014

(87) PCT Pub. No.: WO2013/071865
PCT Pub. Date: May 23, 2013

(65) Prior Publication Data
US 2014/0296261 A1    Oct. 2, 2014

Related U.S. Application Data

(60) Provisional application No. 61/559,451, filed on Nov. 14, 2011.

(51) Int. Cl.
*A61K 31/519* (2006.01)
*C07D 487/04* (2006.01)
*C07D 473/00* (2006.01)

(52) U.S. Cl.
CPC ........... *C07D 473/00* (2013.01); *C07D 487/04* (2013.01)

(58) Field of Classification Search
CPC .................................................... C07D 487/04
See application file for complete search history.

(56) References Cited

FOREIGN PATENT DOCUMENTS

WO    2010/126895 A1    11/2010
WO    2012/074249 A2    6/2012

OTHER PUBLICATIONS

Ahn, et al., "The role of autophagy in cytotoxicity induced by new oncogenic B-Raf inhibitor UI-152 in v-Ha-*ras* transformed fibroblasts," *Biochemical and Biophysical Research Communications*, vol. 417, Issue 2, pp. 857-863 (2012).
International Search Report for PCT/CN2012/084595 mailed on Feb. 28, 2013.

*Primary Examiner* — Brian McDowell
(74) *Attorney, Agent, or Firm* — Kilpatrick Townsend & Stockton LLP

(57) ABSTRACT

The invention provides a compound represented by formula (I) which may modulate a kinase, and a pharmaceutical composition thereof, as well as the method for preventing or treating a protein kinase mediated disease or condition.

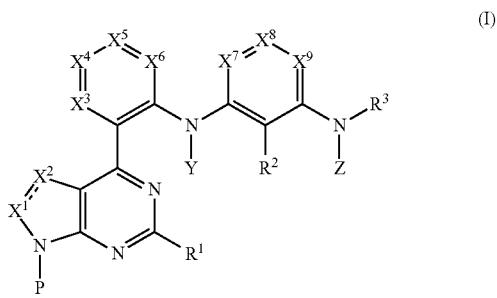

14 Claims, No Drawings

KINASE MODULATING COMPOUNDS, COMPOSITIONS CONTAINING THE SAME AND USE THEREOF

This application is the national stage of PCT/CN2012/084595, filed Nov. 14, 2012, which claims the benefit of U.S. Provisional Application No. 61/559,451, filed on Nov. 14, 2011.

FIELD OF THE INVENTION

The present invention relates to kinase modulating compounds, pharmaceutical compositions thereof, and methods for preventing or treating a protein kinase mediated disease or condition, as well as uses in manufacturing a medicament or the pharmaceutical composition for preventing or treating the disease or condition.

BACKGROUND ART

The information provided herein is intended solely to assist the understanding of the reader. None of the information provided nor references cited is admitted to be prior art to the present invention.

Protein kinase is known as protein phosphatase, which distributes throughout the nuclear, mitochondrial, microsomal and cytosol. The human genome contains about 500 protein kinase genes and they constitute about 2% of all human genes. Up to 30% of all human proteins may be modified by kinase activity, and kinases are known to regulate the majority of cellular pathways, especially those involved in signal transduction. It has been found to have more than 400 kinds of human diseases associated with protein kinase.

Specific disease states associated with aberrant regulation of protein kinases include, for example without limitation, melanoma, colorectal cancer, colon cancer, gastric cancer, pelvic cancer, esophageal cancer, brain cancer, testicular cancer, bone cancer, lymphoma, lung cancer, breast cancer, pancreatic cancer, thyroid cancer, ovarian cancer, liver cancer, kidney cancer, glioma, sarcoma, medullary thyroid carcinoma, carcinoid, small cell lung cancer, leukemia, neurofibromatosis, myelodysplastic syndrome, tumor angiogenesis, neuropathic pain, inflammatory pain, acute and chronic pain, cancer-related pain, migraine headaches, heart failure, ischemic stroke, cardiac hypertrophy, thrombosis, atherosclerosis, multi-infarct dementia, head injury, spinal cord injury, Parkinson's disease, Alzheimer's disease, psoriasis, arthritis, bone and joint inflammation, fibrois, rheumatoid arthritis, inflammatory bowel disease, immune deficiency diseases, organ transplant rejection, graft versus host disease, diabetic nephropathy, polycystic kidney disease, nephrosclerosis, glomerulonephritis, prostatic hyperplasia, diabetes, obesity, *H. pylori* infection, hepatitis infection, influenza virus infection, fever, sepsis, chronic obstructive pulmonary disease, acute respiratory distress syndrome, muscular dystrophy, motor neuron disease, neuromuscular disease, endocrine abnormalities of the disease, peripheral nerve diseases, glandular diseases, body and muscle metabolic diseases.

SUMMARY OF THE INVENTION

The present invention concerns compounds active on protein kinases in general, including, but not limited to, Ab1, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, 1GF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk 1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, Yes, and/or Zap70, including any mutations of these kinases, and the use thereof in treating disease and conditions associated with regulation of the activity of the kinase. In particular, the invention concerns compounds of Formula I as described below. Thus, the invention provides novel use of compounds for therapeutic methods involving modulation of protein kinases, as well as novel compounds that can be used for therapeutic methods involving modulation of protein kinases.

In one aspect, the invention provides a compound represented by Formula (I), or a pharmaceutically acceptable salt, solvate, poly-morph, tautomer or prodrug thereof:

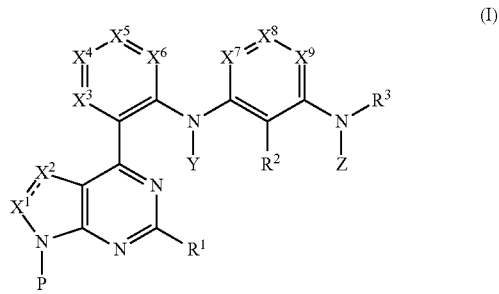

(I)

wherein:

$R^1$ is selected from hydrogen, alkyl, alkenyl, alkynyl, cycloalkyl, heterocloalkyl, aryl, heteroaryl, alkoxy, alkylthio, or halogen, wherein the above said groups are optionally substituted with one or more substituents selected from the group consisting of halogen, —OH, —NH$_2$, lower alkyl, lower alkoxy, lower alkylthio, lower mono-alkylamino, lower di-allylamino, and lower cycloalkylanimo;

$R^2$ is selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, wherein the above said groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo;

$R^3$ is selected from the group consisting of —S(=O)$_2$R$^a$; —S(=O)$_2$NR$^a$R$^b$; —S(=O)R$^a$; —S(=O)NR$^a$R$^b$; —C(=O)R$^a$; —C(=O)NR$^a$R$^b$; —C(=O)OR$^a$;

$R^a$ and $R^b$ are independently selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, wherein those groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, cycloalkylamino, and aryl optionally substituted with one or more halogen, hydroxyl, amino, lower alkyl, lower alkoxy, lower alkylthio; or $R^a$ and $R^b$ combine to form a cycloalkyl or heterocycloalkyl, wherein the cycloalkyl or heterocycloalkyl is optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo; or $R^a$ and $R^b$ are independently selected from the group consisting of —(CR$^c$R$^d$)$_n$R$^e$ and —(CR$^c$R$^d$)$_n$OR$^e$;

$R^c$ and $R^d$ are independently selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, wherein those groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo; or $R^c$ and $R^d$ combine to form a cycloalkyl or heterocycloalkyl, wherein the cycloalkyl or heterocycloalkyl is optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo;

$R^e$ is selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, wherein those groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo;

n is 0, 1, 2, 3, 4, 5 or 6;

$X^1$ and $X^2$ are independently selected from the group consisting of CR$^4$, N, NR$^5$ to form a 5 membered heterocycloalkyl or a 5 membered heteroaryl;

$R^4$ and $R^5$ are independently selected from the group consisting of hydrogen, halogen, lower alkyl, alkenyl, alkynyl, cycloalkyl, heterocloalkyl, aryl, heteroaryl, alkoxy, alkylthio, alkoxycarbonyl, cyano, —OH, —NHC(=O)-alkyl, —S(=O)$_2$-alkyl, —S(=O)$_2$-cycloalkyl, —S(=O)$_2$NH$_2$, —S(=O)$_2$NH-alkyl, —N(alkyl), —S(=O)$_2$-alkyl, —NHS(=O)$_2$-alkyl, —NHS(=O)$_2$-cycloalkyl, —NHS(=O)$_2$-aryl, —NHS(=O)$_2$-heteroaryl, —S(=O)$_2$N-(alkyl)$_2$, —C(=O)NH-alkyl, —C(=O)N-(alkyl)$_2$, —S(=O)-alkyl, —S(=O)-heteroalkyl, —C(=O)NH$_2$, triazole, tetrazole, wherein the said groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo;

$X^3$, $X^4$, $X^5$ and $X^6$ are independently selected from the group consisting of CR$^6$, N, NR$^7$ to form a 6 membered aryl or heteroaryl;

$R^6$ and $R^7$ are independently selected from the group consisting of hydrogen, halogen, alkyl, alkenyl, alkynyl, cycloalkyl, heterocloalkyl, aryl, heteroaryl, alkoxy, alkoxycarbonyl, cyano, —OH, —NHC(=O)-alkyl, —S(=O)$_2$-alkyl, —S(=O)$_2$-cycloalkyl, —S(=O)$_2$NH$_2$, —S(=O)$_2$NH-alkyl, —N(alkyl), —S(=O)$_2$-alkyl, —C(=O)-alkyl, —NO$_2$, —NHS(=O)$_2$-alkyl, —NHS(=O)$_2$-cycloalkyl, —NHS(=O)$_2$-aryl, —NHS(=O)$_2$-heteroaryl, —S(=O)$_2$N-(alkyl)$_2$, —C(=O)NH-alkyl, —C(=O)N-(alkyl)$_2$, —S(=O)-alkyl, —S(=O)-heteroalkyl, —C(=O)NH$_2$, triazole, tetrazole, wherein the said groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo;

$X^7$, $X^8$ and $X^9$ are independently selected from the group consisting of CR$^8$, N, NR$^9$ to form a 6 membered aryl or heteroaryl;

$R^8$ and $R^9$ are independently selected from the group consisting of hydrogen, halogen, alkyl, alkenyl, alkynyl, cycloalkyl, heterocloalkyl, aryl, heteroaryl, alkoxy, alkylthio, alkoxycarbonyl, cyano, —OH, —NHC(=O)-alkyl, —S(=O)$_2$-alkyl, —S(=O)$_2$-cycloalkyl, —S(=O)$_2$NH$_2$; —S(=O)$_2$NH-alkyl, —N(alkyl), —S(=O)$_2$-alkyl, —C(=O)-alkyl, —NO$_2$, —NHS(=O)$_2$-alkyl, —NHS(=O)$_2$-cycloalkyl, —NHS(=O)$_2$-aryl, —NHS(=O)$_2$-heteroaryl, —S(=O)$_2$N-(alkyl)$_2$, —C(=O)NH-alkyl, —C(=O)N-(alkyl)$_2$, —S(=O)-alkyl, —S(=O)-heteroalkyl, —C(=O)NH$_2$, triazole, tetrazole, wherein the said groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo;

P, Y and Z are independently, selected from the group consisting of hydrogen, alkyl, alkenyl, alkynyl, cycloalkyl, heterocloalkyl, aryl and heteroaryl, wherein those groups are optionally substituted with one or more substituents selected from halogen, hydroxyl, amino, and cyano.

In some embodiments, the compounds of the invention are those represented by formula (I) wherein $R^3$ is —S(=O)$_2$R$^{10}$, and R$^{10}$ is selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, wherein those groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, cycloalkylanimo, and aryl optionally substituted with one or more halogen, hydroxyl, amino, lower alkyl, lower alkoxy, lower alkylthio; or $R^{10}$ is selected from the group consisting of —(CR$^{11}$R$^{12}$)$_m$R$^{13}$ and —(CR$^{11}$R$^{12}$)$_m$OR$^{13}$, wherein R$^{11}$ and R$^{12}$ are independently selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, and these groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo; or $R^{11}$ and $R^{12}$ combine to form a cycloalkyl or heterocycloalkyl, wherein the cycloalkyl or heterocycloalkyl is optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo; $R^{13}$ is selected from the group consisting of hydrogen, halogen, alkyl, alkenyl, alkynyl, cycloalkyl, heterocloalkyl, aryl, heteroaryl, alkoxy, alkoxycarbonyl, alkylthio, cyano, —OH, —NH$_2$, wherein those groups are optionally substituted with one or more substituents selected from the group consisting of halogen, —OH, —NH$_2$, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylanimo; and m is 0, 1, 2, 3, 4, 5 or 6.

In some embodiments, the compounds of the present invention are those represented by Formula (A):

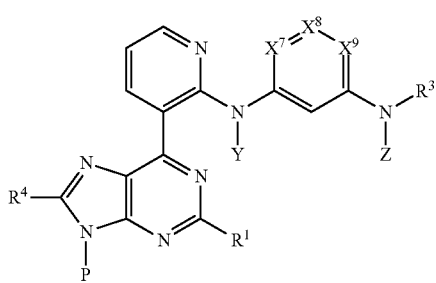

(A)

wherein, $R^1$, $R^3$, $R^4$, $X^7$, $X^8$, $X^9$, P, Y and Z are defined as above.

In some embodiments, the compounds of the present invention are those represented by formula (A), wherein $R^1$ is selected from hydrogen, lower alkyl, lower alkenyl, lower alkynyl, lower cycloalkyl, lower heterocloalkyl, lower alkoxy, lower alkylthio, or halogen, wherein the said groups are optionally substituted with one or more substituents selected from the group consisting of halogen, —OH and —NH$_2$;
$R^3$ is =S(=O)$_2$R$^{10}$, wherein R$^{10}$ is selected from the group consisting of hydrogen, lower alkyl, lower alkenyl, lower alkynyl, lower cycloalkyl, lower heterocloalkyl, monocyclic aryl, monocyclic heteroaryl, lower alkoxy and lower alkylthio, wherein those groups are optionally substituted with one or more substituents selected from the group consisting of halogen, —OH, —NH$_2$, lower alkyl, halogen substituted lower alkyl, lower cycloalkyl, halogen substituted lower cycloalkyl, lower alkoxy, halogen substituted lower alkoxy, lower alkylthio, halogen substituted lower alkylthio, mono-lower alkylamino, di-lower alkylamino, and lower cycloalkylanimo;
$R^4$ is selected from the group consisting of hydrogen, halogen, lower alkyl, lower alkenyl, lower alkynyl, lower cycloalkyl, lower heterocloalkyl, monocyclic aryl, monocyclic heteroaryl, lower alkoxy, lower alkylthio, lower alkoxycarbonyl, cyano, —OH, —NHC(=O)-lower alkyl, —S(=O)$_2$-lower alkyl, —S(=O)$_2$-lower cycloalkyl, —S(=O)$_2$NH$_2$, —S(=O)$_2$NH-lower alkyl, —N(lower alkyl)-S(=O)$_2$-lower alkyl, —C(=O)-lower alkyl, —NO$_2$, —NHS(=O)$_2$-lower alkyl, —NHS(=O)$_2$— lower cycloalkyl, —NHS(=O)$_2$-monocyclic aryl, —NHS(=O)$_2$-monocyclic heteroaryl, —S(=O)$_2$N-(lower alkyl)$_2$, —C(=O)NH-lower alkyl, —C(=O)N-(lower alkyl)$_2$, —S(=O)-lower alkyl, —S(=O)-lower cycloalkyl, —C(=O)NH$_2$, triazole, tetrazole, wherein the said groups are optionally substituted with one or more substituents selected from the group consisting of halogen, —OH, —NH$_2$, lower alkyl, lower alkoxy, lower alkylthio, lower cycloalkyl, halogen substituted lower alkyl, halogen substituted lower alkoxy, halogen substituted lower alkylthio, halogen substituted lower cycloalkyl, mono-lower alkylamino, di-lower alkylamino, and lower cycloalkylanimo;
$X^7$ is CR$^8$, and $X^8$ and $X^9$ are independently selected from the group consisting of CR$^8$, N, NR$^9$ to form a 6 membered aryl or heteroaryl; wherein $R^8$ and $R^9$ are independently selected from the group consisting of hydrogen, halogen, lower alkyl, lower alkenyl, lower alkynyl, lower cycloalkyl, lower heterocloalkyl, monocyclic aryl, monocyclic heteroaryl, lower alkoxy, lower alkylthio, lower alkoxycarbonyl, cyano, —OH, —NHC(=O)-lower alkyl, —S(=O)$_2$-lower alkyl, —S(=O)$_2$-lower cycloalkyl, —S(=O)$_2$NH$_2$, —S(=O)$_2$NH-lower alkyl, —S(=O)$_2$N-(lower alkyl)$_2$, —N(lower alkyl)-S(=O)$_2$-alkyl, —C(=O)-lower alkyl, —NO$_2$, —NHS(=O)$_2$-lower alkyl, —NHS(=O)$_2$-lower cycloalkyl, —NHS(=O)$_2$-monocyclic aryl, —NHS(=O)$_2$-monocyclic heteroaryl, —C(=O)NH-lower alkyl, —C(=O)N-(lower alkyl)$_2$, —S(=O)-lower alkyl, —S(=O)-lower cycloalkyl, —C(=O)NH$_2$, triazole, tetrazole, wherein the said groups are optionally substituted with one or more substituents selected from the group consisting of halogen, —OH, —NH$_2$, lower alkyl, halogen substituted lower alkyl, lower cycloalkyl, halogen substituted lower cycloalkyl, lower alkoxy, halogen substituted lower alkoxy, lower alkylthio, halogen substituted lower alkylthio, mono-alkylamino, di-alkylamino, and lower cycloalkylanimo; and P, Y and Z are independently selected from the group consisting of hydrogen, lower alkyl, lower alkenyl, lower alkynyl, lower cycloalkyl, lower heterocloalkyl, monocyclic aryl and monocyclic heteroaryl, wherein said groups are optionally substituted with one or more substituents selected from halogen, hydroxyl, amino, and cyano.

In some embodiments, the compounds of the present invention are those represented by formula (A), wherein P, Y and Z are hydrogen.

In some embodiments, the compounds of the present invention are those represented by formula (A), wherein $R^1$ is selected from hydrogen, lower alkyl, lower cycloalkyl, lower heterocloalkyl, lower alkoxy or halogen, wherein the said groups are optionally substituted with one or more substituents selected from the group consisting of halogen, —OH and —NH$_2$; and/or $R^3$ is —S(=O)$_2$R$^{10}$, wherein R$^{10}$ is selected from the group consisting of hydrogen, lower alkyl, lower alkenyl, lower alkynyl, lower cycloalkyl, lower heterocloalkyl, lower alkoxy, lower alkylthio, wherein those groups are optionally substituted with one or more substituents selected from the group consisting of halogen, —OH and —NH$_2$.

In some embodiments, the compounds of the invention are those represented by formula (A), wherein R$^3$ is —S(=O)$_2$R$^{10}$, in which R$^{10}$ is selected from the group consisting of hydrogen, lower alkyl, lower alkenyl, lower cycloalkyl, monocyclic aryl and monocyclic heteroaryl, and these groups are optionally substituted with one or more substituents selected from the group consisting of halogen, —OH, —NH$_2$, monocyclic aryl and monocyclic aryl substituted with one or more halogen, hydroxyl, lower alkyl, lower alkoxy, lower alkylthio.

In some embodiments, the compounds of the present invention are those represented by formula (A), wherein $R^4$ is selected from the group consisting of hydrogen, halogen, lower alkyl, lower alkenyl, lower alkynyl, lower cycloalkyl, lower heterocloalkyl, lower alkoxy, cyano and —OH, and the said groups are optionally substituted with one or more substituents selected from the group consisting of halogen, —OH and —$NH_2$.

In some embodiments, the compounds of the present invention are those represented by formula (A), wherein $X^7$ is $CR^8$, and $X^8$ and $X^9$ are independently selected from the group consisting of $CR^8$, N, $NR^9$ to form a 6 membered aryl (such as phenyl) or heteroaryl (such as pyridyl); and $R^8$ and $R^9$ are independently selected from the group consisting of hydrogen, halogen, lower alkyl, lower cycloalkyl, lower heterocloalkyl and lower alkoxy; wherein the said groups are optionally substituted with one or more substituents selected from the group consisting of halogen, —OH and —$NH_2$.

In some embodiments, the compounds of the present invention are those represented by any of the following formula:

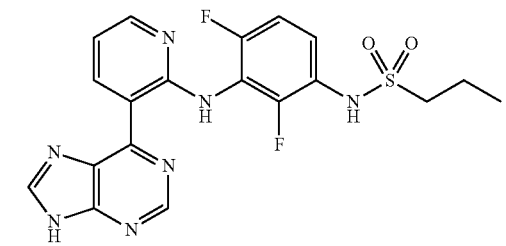

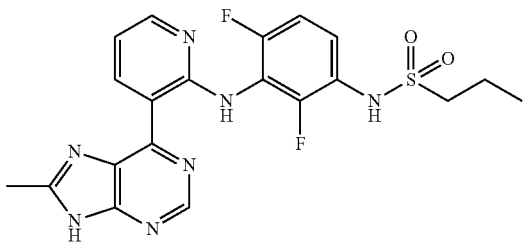

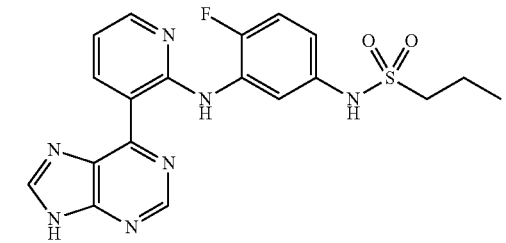

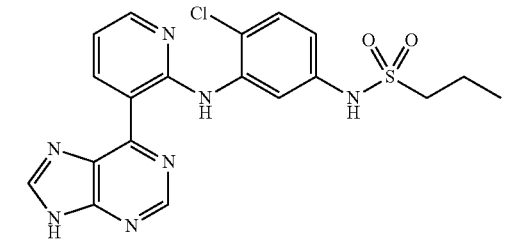

-continued

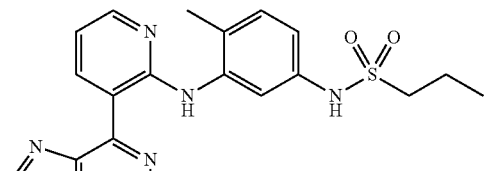

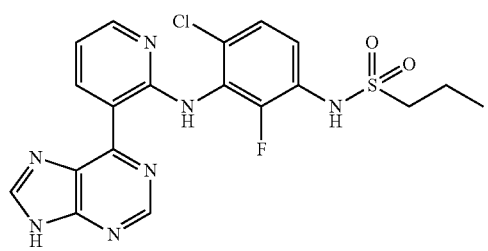

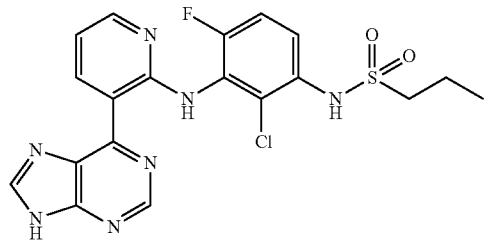

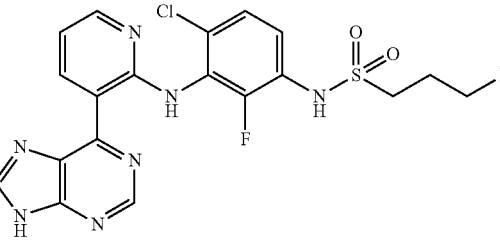

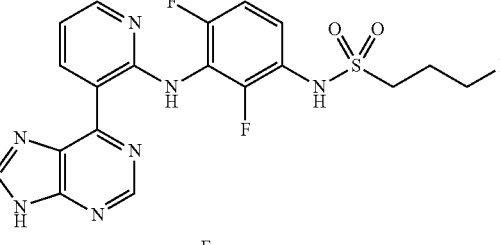

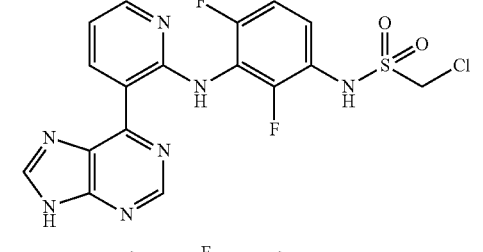

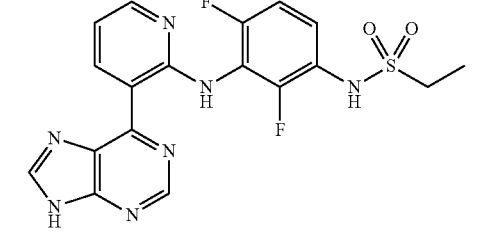

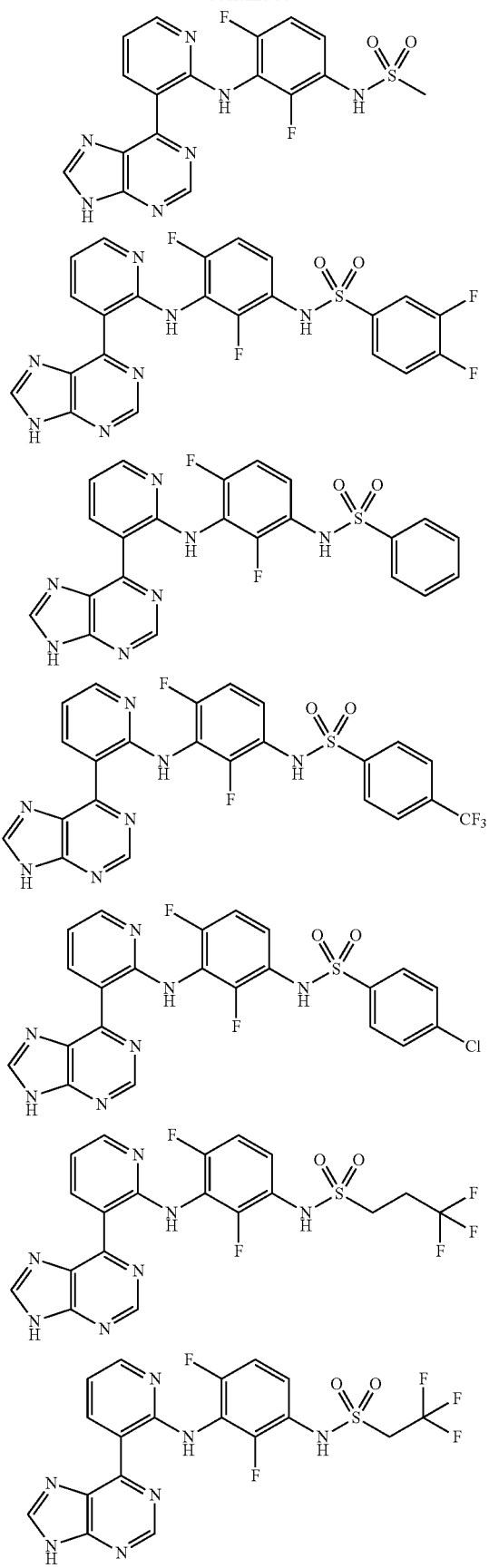
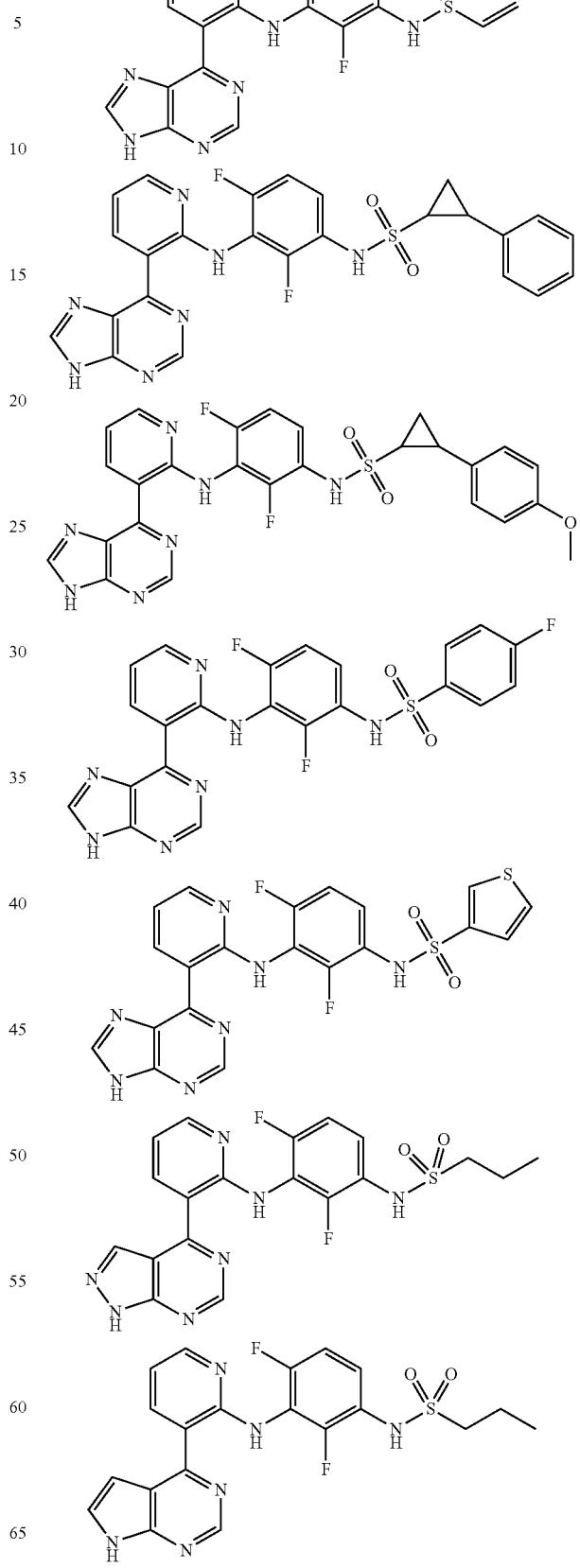

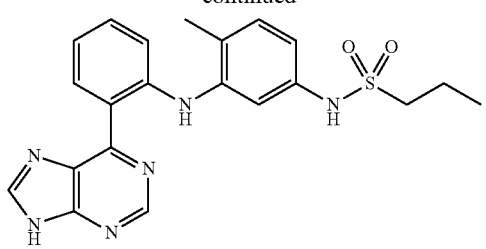

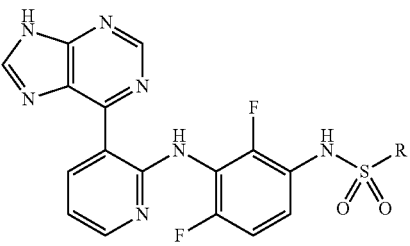

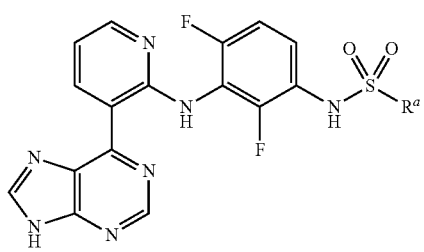

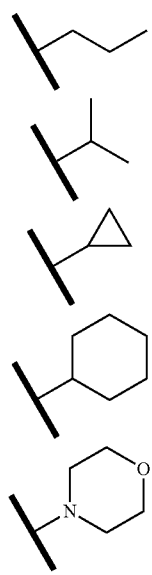

In some embodiments, the compounds of the invention defined as above do not include any of the compounds represented by the following formula (B):

(B)

wherein, $R^a$ is any of those defined as above in formula (I), or $R^a$ is $R^{10}$ as any of those defined above in formula A.

In some embodiments, the compounds of the invention defined as above do not include any of the compounds represented by the following formula (C):

(C)

wherein, R is linear or branched $C_1$-$C_6$ alkyl; unsubstituted $C_3$-$C_6$ cycloalkyl or $C_3$-$C_6$ cycloalkyl substituted by one or more substituents selected from the group consisting of halogen and linear or branched $C_1$-$C_6$ alkyl; unsubstituted $C_5$-$C_6$ aryl or $C_5$-$C_6$ aryl substituted by one or more substituents selected from the group consisting of halogen, linear or branched $C_1$-$C_6$ alkyl or $C_1$-$C_6$ alkoxy, and linear or branched $C_1$-$C_6$ alkyl or $C_1$-$C_6$ alkoxy substituted by halogen; unsubstituted monocyclic or bicyclic $C_5$-$C_{12}$ heteroaryl or monocyclic or bicyclic $C_5$-$C_{12}$ heteroaryl substituted by unsubstituted linear or branched $C_1$-$C_6$ alkyl or linear or branched $C_1$-$C_6$ alkyl substituted by halogen, linear or branched $C_1$-$C_6$ alkoxycarbony, and $C_5$-$C_6$ heterocycloalkyl having one or more oxygen (O) as a ring atom; unsubstituted $C_5$-$C_6$ heterocycloalkyl or $C_5$-$C_6$ heterocycloalkyl substituted by one or more substituents selected form the group consisting of halogen and linear or branched $C_1$-$C_6$ alkyl; or unsubstituted $C_5$-$C_6$ aryl-linear or branched $C_1$-$C_6$ alkyl or $C_5$-$C_6$ aryl-linear or branched $C_1$-$C_6$ alkyl substituted by one or more substituents selected from the group consisting of halogen, nitro and linear or branched $C_1$-$C_6$ alkyl, where the said heteroaryl or heterocycloalkyl contains one or more heteroatoms as a ring atom selected from the group consisting of N, O and S.

In some embodiments, the compounds of the invention defined as above do not include any of the compounds represented by the formula (C), wherein, R is any of the groups or moieties selected from the group consisting of the followings:

-continued
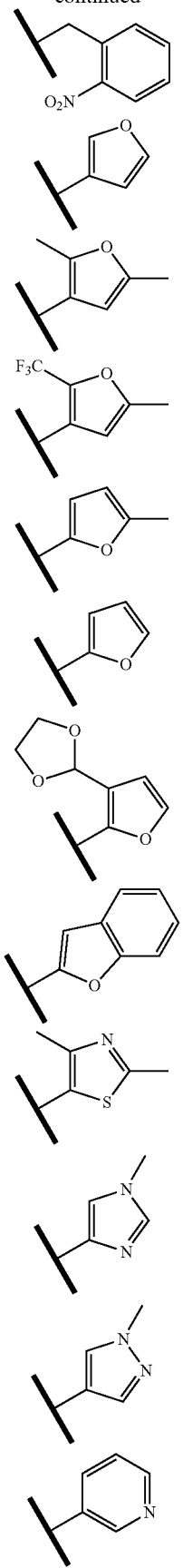
-continued
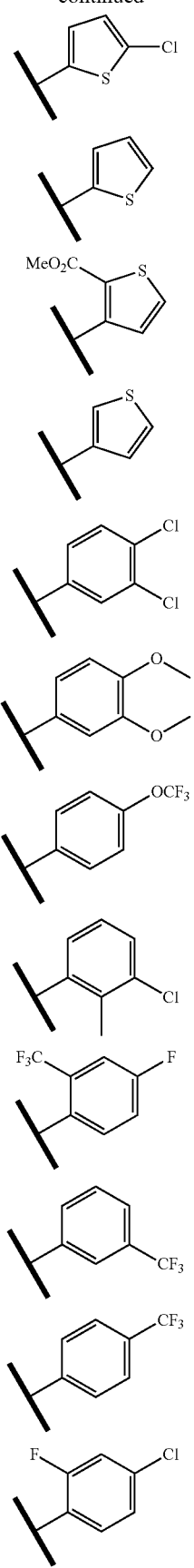

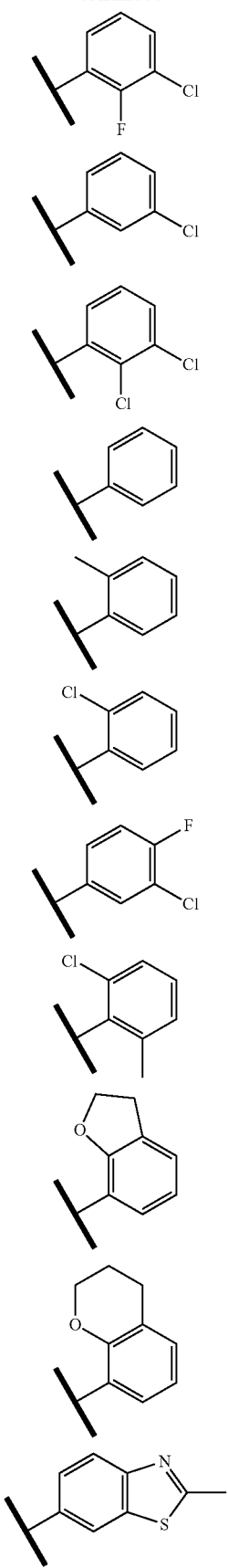
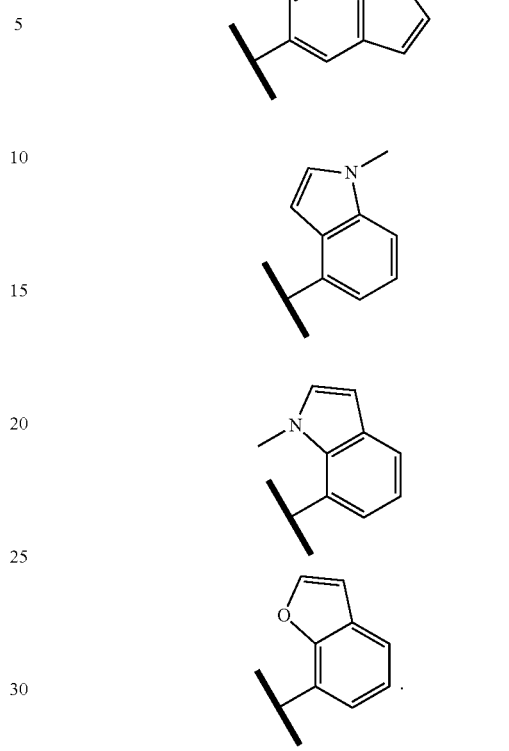
In, some embodiments, the compounds of the invention defined as above do not include any of the compounds represented by the following formula:
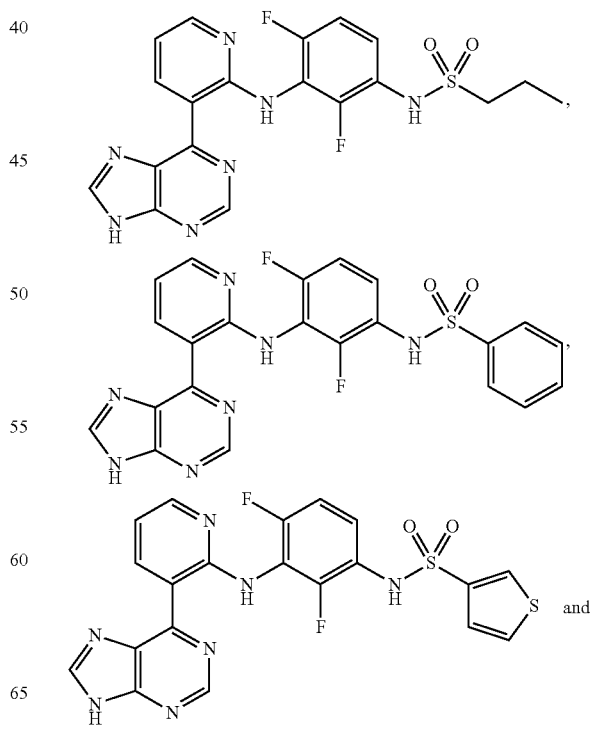

-continued

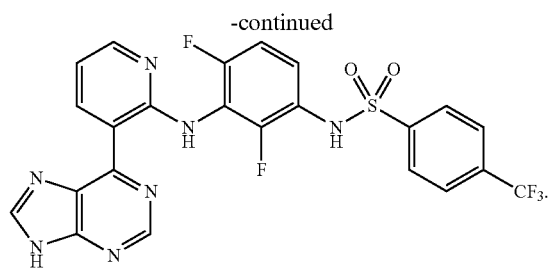

In another aspect, the invention provides a pharmaceutical composition comprising at least one compound of the invention or pharmaceutically acceptable salt, solvate, poly-morph, tautomer or prodrug thereof and a pharmaceutically acceptable carrier.

In another aspect, the invention provides a method for modulating a protein kinase (in vivo or in vitro). In some embodiments, some compounds can inhibit some protein kinases. In some embodiments, the compounds of the invention can be used for modulating a kinase.

In another aspect, the invention provides a compound of the invention for modulating a kinase. In some embodiments, some compounds can inhibit some protein kinases.

In another aspect, the invention provides a method for preventing or treating a subject suffering from or at risk of a protein kinase mediated disease or condition, comprising administering to said subject an effective amount of a compound of this invention or a pharmaceutically acceptable salt, solvate, poly-morph, tautomer or prodrug thereof or a pharmaceutical composition of this invention.

In another aspect, the invention provides use of a compound of the invention or a pharmaceutically acceptable salt, solvate, poly-morph, tautomer or prodrug thereof in the preparation of a medicament for preventing or treating a subject suffering from or at risk of a protein kinase mediated disease or condition.

In another aspect, the invention provides a kit comprising a compound of the invention or a pharmaceutically acceptable salt, solvate, poly-morph, tautomer or prodrug thereof, or a pharmaceutical composition of the invention. In some embodiments, the kit is used for preventing or treating a subject suffering from or at risk of a protein kinase mediated disease or condition.

In some embodiments, the subject is a mammal, such as human.

In some embodiments, the disease or condition is selected from the group consisting of melanoma, colorectal cancer, colon cancer, gastric cancer, pelvic cancer, esophageal cancer, brain cancer, testicular cancer, bone cancer, lymphoma, lung cancer, breast cancer, pancreatic cancer, thyroid cancer, ovarian cancer, liver cancer, kidney cancer, glioma, sarcoma, medullary thyroid carcinoma, carcinoid, small cell lung cancer, leukemia, neurofibromatosis, myelodysplastic syndrome, tumor angiogenesis, neuropathic pain, inflammatory pain, acute and chronic pain, cancer-related pain, migraine headaches, heart failure, ischemic stroke, cardiac hypertrophy, thrombosis, atherosclerosis, multi-infarct dementia, head injury, spinal cord injury, Parkinson's disease, Alzheimer's disease, psoriasis, arthritis, bone and joint inflammation, fibrosis, rheumatoid arthritis, inflammatory bowel disease, immune deficiency diseases, organ transplant rejection, graft versus host disease, diabetic nephropathy, polycystic kidney disease, nephrosclerosis, glomerulonephritis, prostatic hyperplasia, diabetes, obesity, *H. pylori* infection, hepatitis infection, influenza virus infection, fever; sepsis, chronic obstructive pulmonary disease, acute respiratory distress syndrome, muscular dystrophy, motor neuron disease, neuromuscular disease, endocrine abnormalities of the disease, peripheral nerve diseases, glandular diseases, body and muscle metabolic diseases.

In another aspect, the invention provided methods for treating a Raf protein kinase mediated disease or condition in an animal subject, wherein the method involves administering to the subject an effective amount of one or more compounds of Formula I. The Raf protein kinase includes, but not limited to, A-Raf, mutations of A-Raf, B-Raf, mutations of B-Raf, c-Raf and mutations of c-Raf. In some embodiments, the Raf protein kinase is B-Raf mutation V600E. In some embodiments, the disease or condition is a cancer that is amenable to treatment by an inhibitor of the V600E mutant B-Raf.

In another aspect, the invention provides a method of treating a cancer by administering to the subject an effective amount of a composition including one or more compounds of Formula I, in combination with one or more other therapies or medical procedures effective in treating cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant).

In another aspect, involving treatment or prophylaxis of a disease or condition with one or more compounds of Formula I, the disease or condition is selected but not limited from the group consisting of melanoma, colorectal cancer, colon cancer, gastric cancer, pelvic cancer, esophageal cancer, brain cancer, testicular cancer, bone cancer, lymphoma, lung cancer, breast cancer, pancreatic cancer, thyroid cancer, ovarian cancer, liver cancer, kidney cancer, glioma, sarcoma, medullary thyroid carcinoma, carcinoid, small cell lung cancer, leukemia, neurofibromatosis, myelodysplastic syndrome, tumor angiogenesis, neuropathic pain, inflammatory pain, acute and chronic pain, cancer-related pain, migraine headaches, heart failure, ischemic stroke, cardiac hypertrophy, thrombosis, atherosclerosis, multi-infarct dementia, head injury, spinal cord injury, Parkinson's disease, Alzheimer's disease, psoriasis, arthritis, bone and joint inflammation, fibrosis, rheumatoid arthritis, inflammatory bowel disease, immune deficiency diseases, organ transplant rejection, graft versus host disease, diabetic nephropathy, polycystic kidney disease, nephrosclerosis, glomerulonephritis, prostatic hyperplasia, diabetes, obesity, *H. pylori* infection, hepatitis infection, influenza virus infection, fever, sepsis, chronic obstructive pulmonary disease, acute respiratory distress syndrome, muscular dystrophy, motor neuron disease, neuromuscular disease, endocrine abnormalities of the disease, peripheral nerve diseases, glandular diseases, body and muscle metabolic diseases.

In another aspect, the present invention is directed to a pharmaceutical composition comprising a compound of this invention or a pharmaceutically acceptable salt, solvate, polymorph, tautomer or prodrug thereof. In some embodiments, the pharmaceutical composition is in a form suitable for administration including but not limited to oral administration, parenteral administration, topical administration and rectal administration. In further or additional embodiments, the pharmaceutical composition is in the form of a tablet, capsule, pill, powder, sustained release formulation, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent.

In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In some embodiments, the individual is a mammal. In further or additional embodiments, the individual is a human. In some embodiments, the composition comprising a compound of formula I is administered in combination with an additional therapy.

In another aspect, the present invention is directed to a process for preparing a compound of formula I or a pharmaceutically acceptable salt, solvate, polymorph, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY $4^{th}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-Cn, includes $C_1$-$C_2$, $C_1$-$C_3$ ... $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges. $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having, for example, from one to about eighteen, or one to about ten carbon atoms, more preferably one to six carbon atoms. The term "lower alkyl" as used herein, alone or in combination, refers to an alkyl having relatively less carbon atoms, for example having one to about eight carbon atoms, preferably having one to about 6, or one to about four carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The "alkyl" as used in combination includes but not limited to the "alkyl" included in "alkoxy", "alkylthio", "mono-alkylamino" and "di-alkylamino", etc.

The term "alkylene" as used herein, alone or in combination, refers to a diradical derived from the above-defined monoradical, alkyl. Examples include, but are not limited to methylene (—CH$_2$), ethylene (—CH$_2$CH$_2$), propylene (—CH$_2$CH$_2$CH$_2$), isopropylene (—CH(CH$_3$)CH$_2$) and the like.

The term "alkenyl" as used herein, alone or in combination, refers to an optionally substituted straight-chain, or optionally substituted branched-chain hydrocarbon monoradical having one or more carbon-carbon double-bonds and having, for example, from two to about eighteen or two to about ten carbon atoms, more preferably two to about six carbon atoms. The group may be in either the cis or trans conformation about the double bond(s), and should be understood to include both isomers. The term "lower alkenyl" as used herein, alone or in combination, refers to an alkenyl having relatively less carbon atoms, for example having two to about eight carbon atoms, preferably having two to about 6, or two to about four carbon atoms. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" or "C$_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (CH—CH), the propenylene isomers (e.g., CH$_2$CH=CH and C(CH$_3$)=CH) and the like.

The term "alkynyl" as used herein, alone or in combination, refers to an optionally substituted straight-chain or optionally substituted branched-chain hydrocarbon monoradical having one or more carbon-carbon triple-bonds and having, for example, from two to about eighteen or two to about ten carbon atoms, more preferably from two to about six carbon atoms. The term "lower alkynyl" as used herein, alone or in combination, refers to an alkynyl having relatively less carbon atoms, for example having two to about eight carbon atoms, preferably having two to about 6, or two to about four carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—CC—), propargylene (—CH$_2$CC—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl, trifluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo, chloro, fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). The cycloalkyl may have three to about ten, or three to about eight, or three to about six, or three to five ring atoms. The examples include but not limited to cyclopropyl, cyclobutyl, cyclopentyl, and cyclohexyl.

The term "lower cycloalkyl" as used herein, alone or in combination, refers to those having relatively less ring atoms, for example, having five to about ten or five to about eight, or five to six ring atoms, or three to six ring atoms, for example, having three, four, five or six ring atoms.

A non-limiting example of "heterocycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized at-electron system containing 4n+2 n electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl), and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings. Moreover, the term aryl includes but not limited to monocycle, bicycle and tricycle or more cycles. The aryl (for example monocyclic aryl) contains, for example, from six to about twelve, or six to about ten, or six to about eight ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A single ring heteroaryl (monocyclic heteroaryl) includes but not limited to those having five to about twelve, or five to about ten, or five to seven, or six ring atoms. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heteroarylene" as used herein, alone or in combination, refers to a diradical derived from the above-defined monoradical heteroaryl. Examples include, but are not limited to pyridinylene and pyrimidinylene.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. The "heterocycle" includes heterocycloalkyl. The "lower heterocycle" or "lower heterocycloalkyl" or the like refers to those having relatively less ring atoms, for example, having five to about ten, or five to about eight, or five or six ring atoms.

The term "carbocyclyl" as used herein, alone or in combination, refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "alkoxy" as used herein, alone or in combination, refers to an alkyl ether radical, 0-alkyl, including the groups 0-aliphatic and 0-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tertbutoxy and the like.

The term "alkylthio" as used herein, alone or in combination, refers to an group of "—S-alkyl", which includes —S-aliphatic groups and —S-carbocycle. The meanings of alkyl, aliphatic groups and carbocycle are the same as defined above. The examples of alkylthio includes but not limited to methylthio, ethylthio, propylthio, butylthio, etc.

The term "lower alkyl", "lower alkoxy" and "lower alkylthio" as used herein, alone or in combination, refers to those having one to about eight, or one to six, or one to five, or one to four, or one to three or one to two carbon atoms.
Certain Pharmaceutical Terminology The term "subject", "patient" or "individual" as used herein in reference to individuals suffering from a disorder, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, y-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19.). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, IV' ($C_{1-4}$alkyl)$_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

EXPERIMENTAL

General Methods: All operations involving moisture and/or oxygen sensitive materials were conducted under an atmosphere of dry nitrogen in pre-dried glassware. Unless noted otherwise, materials were Obtained from commercially available sources and used without further purification.

Column chromatography was performed on Qingdao Haiyang Chemical CO., LTD. silica gel (200-300 mesh). Thin layer chromatography was performed using precoated plates purchased from E. Merck (silica gel 60 $PF_{254}$, 0.25 mm).

Nuclear magnetic resonance (NMR) spectra were recorded on Varian VNMRS-400 resonance spectrometer. $^1$H NMR chemical shifts are giving in parts per million (δ) downfield from tetramethylsilane (TMS). $^1$H NMR information is tabulated in the following format: number of protons, multiplicity (s, singlet; d, doublet; t, triplet; q, quarter; m, multiplet), coupling constant(s) (J) in Hertz.

LC/MS was taken on Mass Spectrometer on FINNIGAN Thermo LCQ Advantage MAX, Agilent LC 1200 series (Column: Waters Symmetry C18, Ø4.6×50 mm, 5 μm, 35° C.) operating in ESI(+) ionization mode.

Scheme 1. General Synthesis Route 1

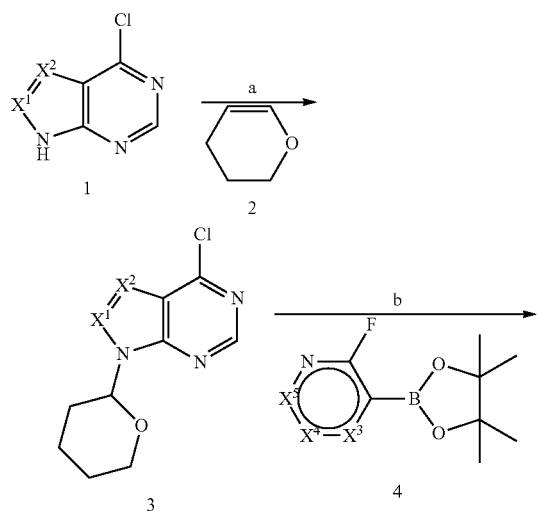

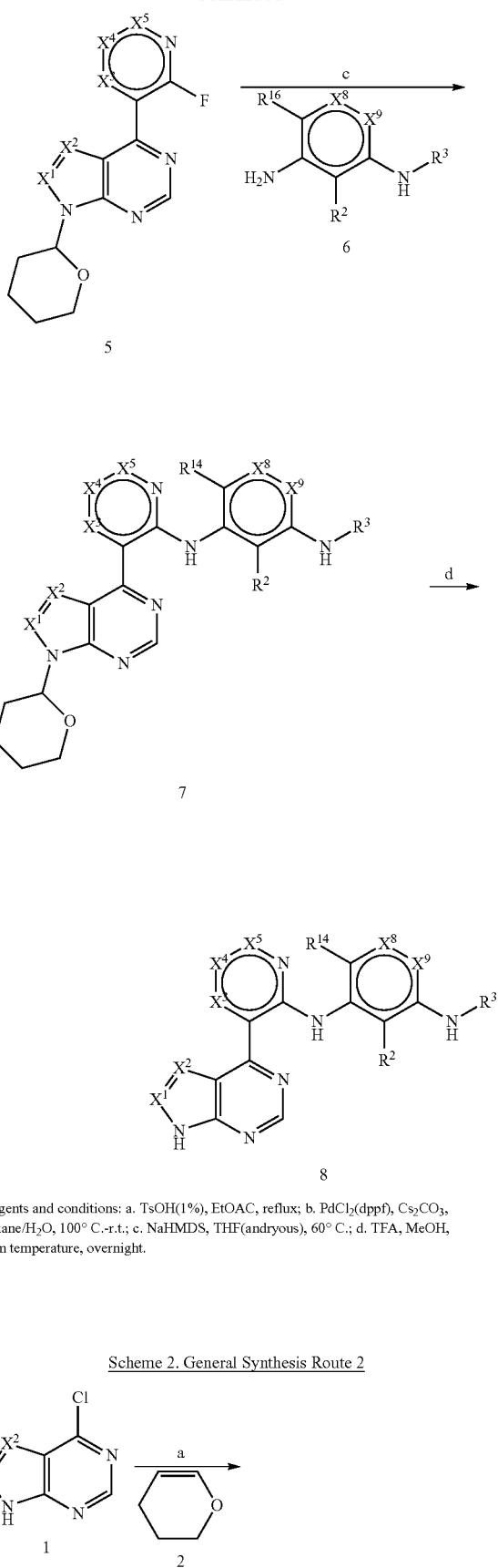

Reagents and conditions: a. TsOH(1%), EtOAC, reflux; b. PdCl$_2$(dppf), Cs$_2$CO$_3$, dioxane/H$_2$O, 100° C.-r.t.; c. NaHMDS, THF(andryous), 60° C.; d. TFA, MeOH, room temperature, overnight.

Scheme 2. General Synthesis Route 2

33
-continued

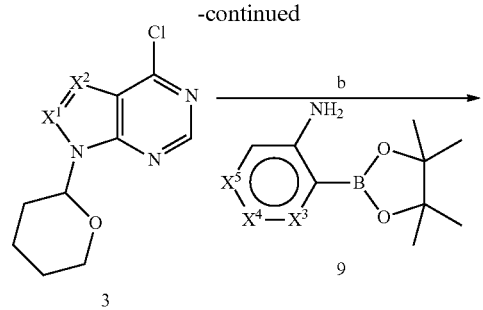

3

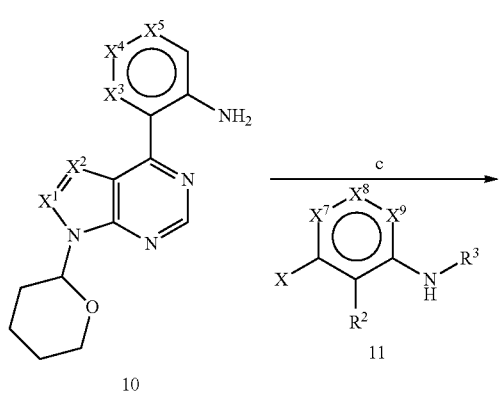

10

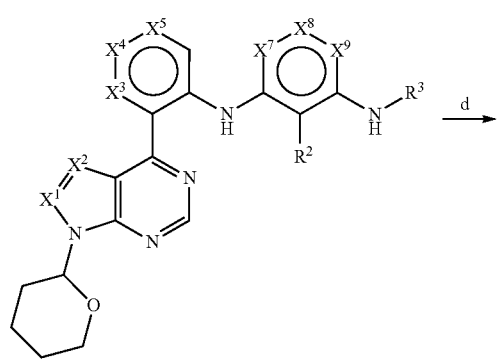

12

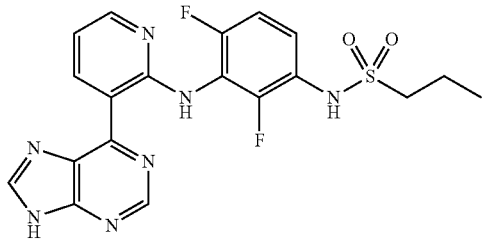 [SMILES: CCCS(=O)(=O)Nc1ccc(F)c(Nc2ncccc2-c2ncnc3[nH]cnc23)c1F]

13

Reagents and conditions: a. TsOH(1%), EtOAC, reflux; b. PdCl2(dppf), Cs2CO3, toluene(andryous), 100° C.; c. Pd or Cu (cata.)coupling; d. TFA, MeOH, room temperature, overnight.

Example 1

N-(3-(3-(9H-purin-6-yl)pyridin-2-ylamino)-2,4-difluorophenyl)propane-1-sulfonamide

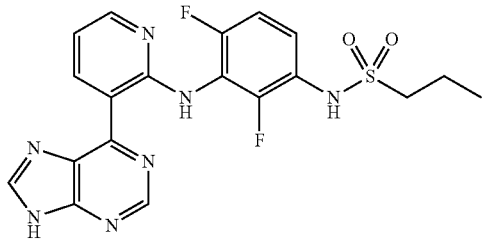 [SMILES: CCCS(=O)(=O)Nc1ccc(F)c(Nc2ncccc2-c2ncnc3[nH]cnc23)c1F]

Step 1: 6-chloro-9-(tetrahydro-2H-pyran-2-yl)-9H-purine

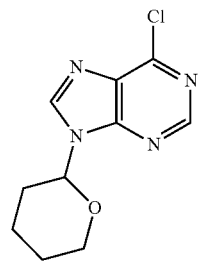 [SMILES: Clc1ncnc2c1ncn2C1CCCCO1]

To a solution of 6-chloro-9H-purine (61.8 g, 0.4 mol) in EtOAc (300 mL) was added 3,4-dihydro-2H-pyran (101 g, 1.2 mol), followed by 4-methylbenzenesulfonic acid (1%) and the resulting reaction mixture was heated to refluxing for 2 hrs. The mixture was diluted with water, extracted with EtOAc, washed with brine, dried over Na$_2$SO$_4$, filtered and concentrated in vacuo. The residue was recrystallized with ether to afford the desired product (65.8 g, 69%).

1H NMR (CDCl$_3$): δ 8.74 (1H, s), 8.33 (1H, s), 5.80-5.76 (1H, m), 4.20-4.16 (1H, m), 3.81-3.75 (1H, m), 2.09-2.00 (3H, m), 1.86-1.65 (4H, m).

Step 2: methyl 2,6-difluorobenzoate

To a solution of 2,6-difluorobenzoic acid (100 g, 0.63 mol) in sulfurous dichloride (150 mL) and the resulting reaction mixture was heated to refluxing for 2 hrs. Sulfurous dichloride was removed in vacuo, the residue in pyridine (100 ml) was added McOH (100 mL) slowly and stirred at room temperature for 2 hrs. The solvent was removed in vacuo, the residue was dissolved in EtOAc (200 mL) and washed with aqueous NaOH (1N), HCl (1N) and brine. The solution was dried over Na$_2$SO$_4$, filtered and concentrated to afford the desired product (78.8 g, 73%).

1H NMR (CDCl$_3$): δ 7.46-7.38 (1H, m), 6.98-9.93 (2H, m), 3.95 (3H, d, J=2.0 Hz).

Step 3: methyl 2,6-difluoro-3-nitrobenzoate

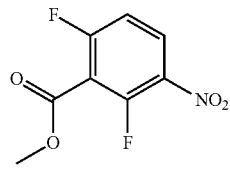

To a solution of methyl 2,6-difluorobenzoate (68.8 g, 0.4 mol) in con. H$_2$SO$_4$ (300 mL) was added potassium nitroperoxous acid (48.5 g, 0.48 mol) for three times and the resulting reaction mixture was stirred at room temperature for 2 hrs. The mixture was dropped into ice-water (500 mL) and filtered. The solid was washed with water and dried to afford the desired product (89 g, 100%).

1H NMR (DMSO-d$_6$): δ 8.49-8.43 (1H, m), 7.56-7.51 (1H, m), 3.95 (3H, s).

Step 4: methyl 3-amino-2,6-difluorobenzoate

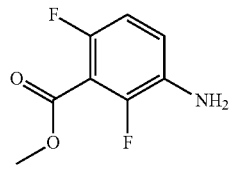

To a solution of methyl 2,6-difluoro-3-nitrobenzoate (50 g, 0.23 mol) in MeOH (150 mL) was added Pd/C (10%) and the resulting reaction mixture was stirred at room temperature for overnight under H$_2$ atmosphere. The mixture was filtered. The filtrate was concentrated in vacuo to afford the desired product (38.8 g, 91%).

1H NMR (CDCl$_3$): δ 6.84-6.73 (2H, m), 3.94 (3H, s), 3.69 (2H, br).

Step 5: methyl 2,6-difluoro-3-(propylsulfonamido)benzoate

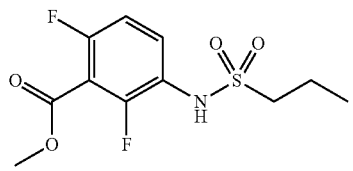 [SMILES: CCCS(=O)(=O)Nc1ccc(F)c(C(=O)OC)c1F]

To a solution of methyl 3-amino-2,6-difluorobenzoate (26.3 g, 0.14 mol) in 1,2-dichloroethane (50 mL) was added pyridine (50 mL), followed by propane-1-sulfonyl chloride (22.0 g, 0.154 mol) and the resulting reaction mixture was heated to 100° C. for 5 hrs. The mixture was diluted with water, extracted with CH$_2$Cl$_2$, washed with brine, dried over Na$_2$SO$_4$, filtered and concentrated in vacuo. The residue was purified with column chromatography (Petrol ether: EtOAc=3:1 to 1:1) to afford the desired product (22.3 g, 54%).

1H NMR (CDCl$_3$): δ 7.74-7.69 (1H, m), 7.02-6.97 (1H, m), 6.45 (1H, br), 3.98 (3H, br), 3.08-3.04 (2H, m), 1.93-1.83 (2H, m), 1.06 (3H, t, J=7.6 Hz).

Step 6: 2,6-difluoro-3-(propylsulfonamido)benzoic acid

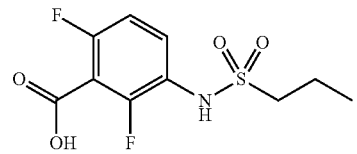 [SMILES: CCCS(=O)(=O)Nc1ccc(F)c(C(=O)O)c1F]

To a solution of methyl 2,6-difluoro-3-(propylsulfonamido)benzoate (22.3 g, 76 mmol) in THF (100 mL) was added LiOH aqueous (2.5 eq.) and the resulting reaction mixture was stirred at room temperature for overnight. The solvent was removed in vacuo and the residue was neutralized with HCl (6N) to pH<1 and filtered. The solid was washed with water and dried to afford the desired product (20.4 g, 96%).

1H NMR (DMSO-d$_6$): δ 9.73 (1H, s), 7.55-7.49 (1H, m), 7.21-7.17 (1H, m), 3.09-3.05 (2H, m), 1.77-1.64 (2H, m), 0.96 (3H, t, J=7.2 Hz).

Step 7: N-(3-amino-2,4-difluorophenyl)propane-1-sulfonamide

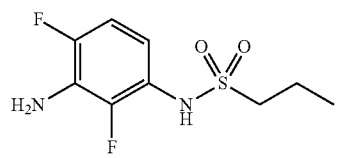 [SMILES: CCCS(=O)(=O)Nc1ccc(F)c(N)c1F]

To a solution of 2,6-difluoro-3-(propylsulfonamido)benzoic acid (18.9 g, 68 mmol) in THF (100 mL) was added Et$_3$N (2.5 eq.), followed by DPPA (22.4 g, 82 mmol) and the resulting reaction mixture was stirred at room temperature for 3 hrs, then continued for 2 hrs at 80° C. Water (10 mL) was added to the solution and stirred for overnight at 80° C. The mixture was diluted with water and extracted with EtOAc, washed with brine, dried over Na$_2$SO$_4$, filtered and concentrated in vacuo. The residue was purified with column chromatography (petrol ether: EtOAc=2:1 to 1:1) to afford the desired product (9.5 g, 55%).

1H NMR (CDCl$_3$): δ 6.92-6.80 (2H, m), 6.33 (1H, br), 3.84 (2H, br), 3.09-3.05 (2H, m), 1.93-1.84 (2H, m), 1.06 (3H, t, J=7.2 Hz).

Step 8: 2-fluoro-3-(4,4,5,5-tetramethyl-1,3,2-dioxa-borolan-2-yl)pyridine

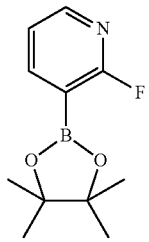 [SMILES: CC1(C)OB(c2cccnc2F)OC1(C)C]

To a solution of diisopropylamine (42.5 g, 0.42 mol) in THF (200 mL) was added n-BuLi (2.5 M, 175 mL) at 0° C. under N₂ atmosphere and the mixture was stirred for 30 hrs. 2-fluoropyridine (34.0 g, 0.35 mol) in ether (50 mL) was added under −60° C. After stirring for 1 hrs at −60° C., triisopropyl borate (82.4 g, 0.44 mol) was drop-wised and the mixture was warmed to room temperature and stirred for 2 hrs. Then pinacol (55.6 g, 0.47 mol) was added, followed by HOAc (22.1 g, 0.37 mol) and the resulting reaction mixture was stirred at room temperature for overnight. The mixture was filtered, the filtrate was extracted with aqueous NaOH (5%), the aqueous was neutralized with HCl (3N) to pH=6-7 and extracted with EtOAc, washed with brine, dried over Na₂SO₄, filtered and concentrated in vacuo to afford the desired product (27.0 g, 34%).

1H NMR (CDCl₃): δ 8.31-8.29 (1H, m), 5.19-8.15 (1H, m), 7.27-7.16 (1H, m), 1.37 (12H, s).

Step 9: 6-(2-fluoropyridin-3-yl)-9-(tetrahydro-2H-pyran-2-yl)-9H-purine

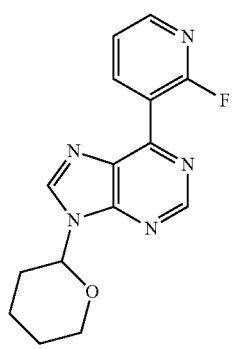 [SMILES: Fc1ncccc1-c1ncnc2c1ncn2C1CCCCO1]

To a solution of 6-chloro-9-(tetrahydro-2H-pyran-2-yl)-9H-purine (7.16 g, 30 mmol) in dioxane/H₂O (100 mL, 10/1) was added 2-fluoro-3-(4,4,5,5-tetramethyl-1,3,2-dioxaborolan-2-yl)pyridine (6.76 g, 30 mmol) and pumped N₂ for 30 min, then PdCl₂(dppf) (3%) and Cs₂CO₃ (24.44 g, 75 mmol) were added and the resulting reaction mixture was stirred at 100° C. for 3 hrs under N₂ atmosphere. The mixture was diluted with water and extracted with EtOAc, washed with brine, dried over Na₂SO₄, filtered and concentrated in vacuo. The residue was purified with column chromatography (petrol ether: EtOAc=2:1 to 1:1) to afford the desired product (6.6 g, 74%).

1H NMR (CDCl₃): δ 9.10 (1H, s), 8.55-8.50 (1H, m), 8.40-8.37 (2H, m), 7.42-7.39 (1H, m), 5.89-5.85 (1H, m), 4.23-4.19 (1H, m) 3.86-3.79 (1H, m), 2.23-2.04 (3H, m), 1.89-1.73 (3H, m).

Step 10: N-(2,4-difluoro-3-(3-(9-(tetrahydro-2H-pyran-2-yl)-9H-purin-6-yl)pyridin-2-ylamino)phenyl)propane-1-sulfonamide

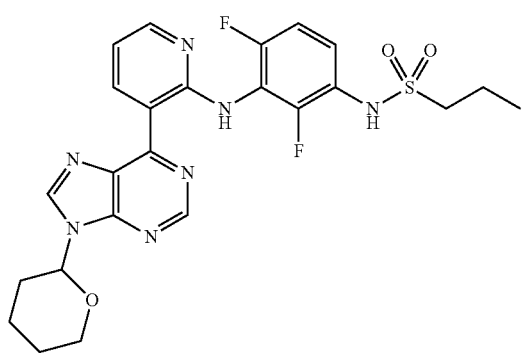 [SMILES: CCCS(=O)(=O)Nc1ccc(F)c(Nc2ncccc2-c2ncnc3c2ncn3C2CCCCO2)c1F]

To a solution of 6-(2-fluoropyridin-3-yl)-9-(tetrahydro-2H-pyran-2-yl)-9H-purine (1.0 g, 3.34 mmol) in THF (10 mL) was added N-(3-amino-2,4-difluorophenyl)propane-1-sulfonamide (0.84 g, 3.34 mmol), followed by NaHMDS (2 M, 6.7 mL) and the resulting reaction mixture was stirred at 60° C. for 2 hrs. The mixture was quenched with HCl (3N), neutralized with saturated aqueous NaHCO₃ and extracted with EtOAc, washed with brine, dried over Na₂SO₄, filtered and concentrated in vacuo. The residue was purified with column chromatography (petrol ether: EtOAc=2:1 to 1:1) to afford the desired product (0.95 g, 54%).

¹H NMR (CDCl₃): δ 11.64 (1H, s), 9.69-9.66 (1H, m), 9.04 (1H, d, J=1.2 Hz), 8.40 (1H, d, J=1.4 Hz), 8.27-8.25 (1H, m), 7.46-7.40 (1H, m), 7.05-6.97 (2H, m), 6.39 (1H, s), 5.91 (1H, d, J=10.4 Hz), 4.26-4.22 (1H, m), 3.88-3.82 (1H, m), 3.13-3.09 (2H, m), 2.24-1.71 (8H, m), 1.09-1.05 (3H, m).

Step 11: N-(3-(3-(9H-purin-6-yl)pyridin-2-ylamino)-2,4-difluorophenyl)propane-1-sulfonamide

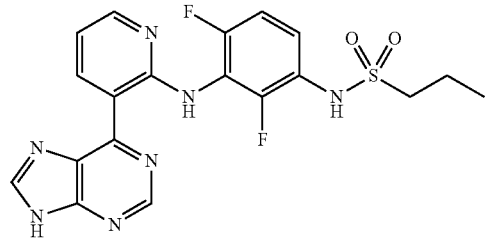 [SMILES: CCCS(=O)(=O)Nc1ccc(F)c(Nc2ncccc2-c2ncnc3[nH]cnc23)c1F]

To a solution of N-(2,4-difluoro-3-(3-(9-(tetrahydro-2H-pyran-2-yl)-9H-purin-6-yl)pyridin-2-ylamino)phenyl)propane-1-sulfonamide (185 mg, 0.35 mmol) in MeOH (5 mL) was added TFA (5 mL) and the resulting reaction mixture was stirred at room temperature for overnight. The mixture was neutralized with saturated aqueous NaHCO₃ to pH>10 and extracted with EtOAc, washed with brine, dried over Na₂SO₄, filtered and concentrated in vacuo. The residue was purified with recrystallized to afford the desired product (150 mg, 96%).

¹H NMR (CDCl₃): δ 13.84 (1H, br), 11.55 (1H, s), 9.67 (2H, br), 9.02 (1H, s), 8.72 (1H, s), 8.19-8.18 (1H, m), 7.30-7.25 (1H, m), 7.19-7.14 (1H, m), 7.04-7.01 (1H, m), 3.08-3.04 (2H, m), 1.79-1.70 (2H, m), 0.96 (3H, t, J=7.2 Hz).

Example 2

N-(3-(3-(8-chloro-9H-purin-6-yl)pyridin-2-ylamino)-2,4-difluorophenyl)propane-1-sulfonamide

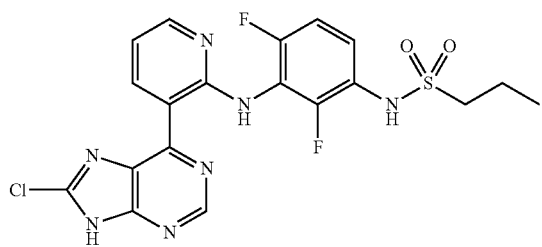 [SMILES: CCCS(=O)(=O)Nc1ccc(F)c(Nc2ncccc2-c2ncnc3[nH]c(Cl)nc23)c1F]

Step 1: N-(3-(3-(8-chloro-9-(tetrahydro-2H-pyran-2-yl)-9H-purin-6-yl)pyridin-2-ylamino)-2,4-difluorophenyl)propane-1-sulfonamide

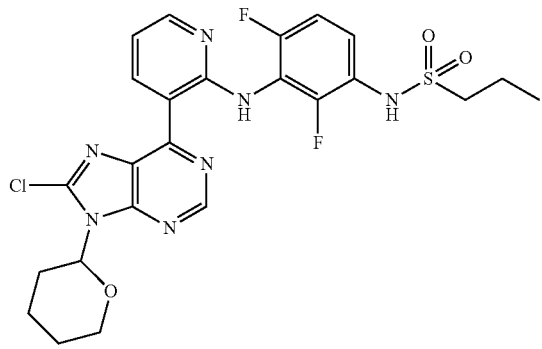 [SMILES: CCCS(=O)(=O)Nc1ccc(F)c(Nc2ncccc2-c2ncnc3c2nc(Cl)n3C2CCCCO2)c1F]

To a solution of N-(2,4-difluoro-3-(3-(9-(tetrahydro-2H-pyran-2-yl)-9H-purin-6-yl)pyridin-2-ylamino)phenyl)propane-1-sulfonamide (Example 2, step 10) (200 mg, 0.378 mmol) in anhydrous THF (8 mL) was added LDA (2 M, 0.66 mL). After the resulting reaction mixture was stirred at −78° C. for 1 hrs, then was added perchloroethane (179 mg, 0.756 mmol) in THF (2 mL) and continued to stirring at −78° C. for 1 hrs. The mixture was quenched with saturated aqueous NH₄Cl, extracted with EtOAc, washed with brine, dried over Na₂SO₄, filtered and concentrated in vacuo. The residue was purified with column chromatography (petrol ether: EtOAc=5:2 to 3:2) to afford the desired product (130 mg, 61%).

1H NMR (CDCl₃): δ 11.48 (1H, s), 9.51-9.48 (1H, m), 8.99 (1H, s, 8.24-8.22 (1H, m), 8.27-8.25 (1H, m), 7.44-7.38 (1H, m), 7.03-6.94 (2H, m), 6.38 (1H, s), 5.88-5.84 (1H, m), 4.26-4.22 (1H, m), 3.80-3.74 (1H, m), 3.11-3.07 (2H, m), 3.03-2.97 (1H, m), 2.22-2.15 (1H, m), 1.94-1.87 (6H, m), 1.05 (3H, t, J=7.2 Hz).

Step 2: N-(3-(3-(8-chloro-9H-purin-6-yl)pyridin-2-ylamino)-2,4-difluorophenyl)propane-1-sulfonamide

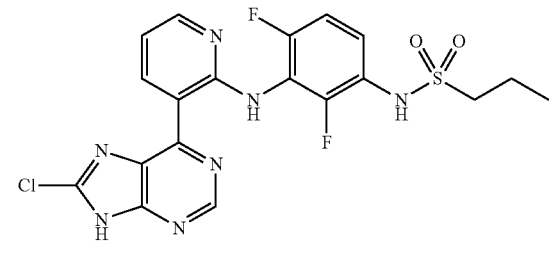 [SMILES: CCCS(=O)(=O)Nc1ccc(F)c(Nc2ncccc2-c2ncnc3[nH]c(Cl)nc23)c1F]

N-(3-(3-(8-chloro-9H-purin-6-yl)pyridin-2-ylamino)-2,4-difluorophenyl)propane-1-sulfonamide was synthesized from N-(3-(3-(8-chloro-9-(tetrahydro-2H-pyran-2-yl)-9H-purin-6-yl)pyridin-2-ylamino)-2,4-difluorophenyl)propane-1-sulfonamide (Example 2, Step 1) in a similar manner as described in Example 1, Step 11.

1H NMR (CD3OD): δ 9.46-9.44 (1H, m), 8.94 (1H, s), 8.15-8.14 (1H, m), 7.43-7.36 (1H, m), 7.09-7.04 (1H, m), 7.02-6.99 (1H, m), 3.13-3.09 (2H, m), 1.90-1.84 (2H, m), 1.07-1.03 (3H, m).

Example 3

N-(2,4-difluoro-3-(3-(8-methyl-9H-purin-6-yl)pyridin-2-ylamino)phenyl)propane-1-sulfonamide

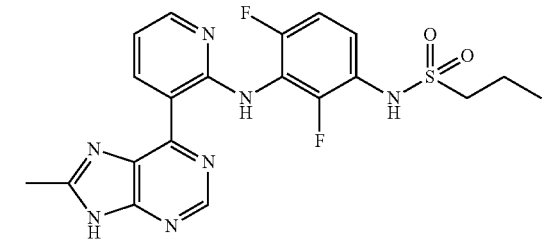 [SMILES: CCCS(=O)(=O)Nc1ccc(F)c(Nc2ncccc2-c2ncnc3[nH]c(C)nc23)c1F]

Step 1: 6-chloro-8-methyl-9-(tetrahydro-2H-pyran-2-yl)-9H-purine

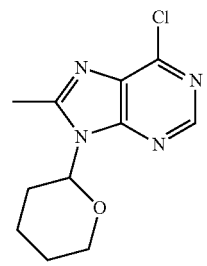 [SMILES: Cc1nc2c(Cl)ncnc2n1C1CCCCO1]

To a solution of 6-chloro-9-(tetrahydro-2H-pyran-2-yl)-9H-purine (Example 1, step 1) (1.00 g, 4.19 mmol) in anhydrous THF (8 mL) was added LDA (2 M, 0.66 mL). After the resulting reaction mixture was stirred at −78° C. for 1 hrs, then was added iodomethane (2.6 mL, 41.9 mmol) and continued to stirring at −78° C. for 3 hrs. The mixture was quenched with saturated aqueous NH₄Cl, extracted with EtOAc, washed with brine, dried over Na₂SO₄, filtered and concentrated in vacuo to afford the desired product (850 mg, 80%).

¹H NMR (CDCl₃): δ 8.67 (1H, s), 5.80-5.76 (1H, m), 4.23-4.19 (1H, m), 3.77-3.70 (1H, m), 2.81 (3H, s), 2.51-2.43 (1H, m), 2.14-2.10 (1H, m), 1.94-1.65 (4H, m).

Step 2: 6-(2-fluoropyridin-3-yl)-8-methyl-9-(tetrahydro-2H-pyran-2-yl)-9H-purine

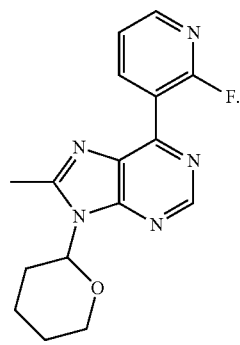 [SMILES: Cc1nc2c(-c3cccnc3F)ncnc2n1C1CCCCO1]

6-(2-fluoropyridin-3-yl)-8-methyl-9-(tetrahydro-2H-pyran-2-yl)-9H-purine was synthesized from 6-chloro-8-methyl-9-(tetrahydro-2H-pyran-2-yl)-9H-purine (Example 3, Step 1) and 2-fluoro-3-(4,4,5,5-tetramethyl-1,3,2-dioxaborolan-2-yl)pyridine (Example 1, Step 8) in a similar manner as described in Example 1, Step 9.

¹H NMR (CDCl₃): δ 9.00 (1H, s), 8.48-8.44 (1H, m), 8.37-8.35 (1H, m), 7.39-7.36 (1H, m), 5.88-5.85 (1H, m), 4.23-4.20 (1H, m), 3.79-3.73 (1H, m), 2.81 (3H, s), 2.57-2.46 (1H, m), 2.14-2.09 (1H, m), 1.97-1.65 (4H, m).

Step 3: N-(2,4-difluoro-3-(3-(8-methyl-9H-purin-6-yl)pyridin-2-ylamino)phenyl)propane-1-sulfonamide

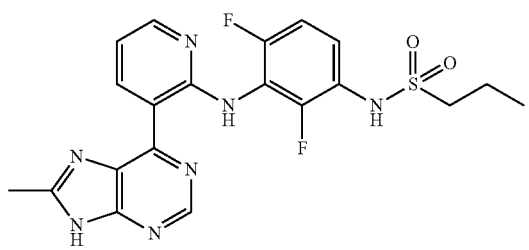 [SMILES: CCCS(=O)(=O)Nc1ccc(F)c(Nc2ncccc2-c2ncnc3[nH]c(C)nc23)c1F]

N-(2,4-difluoro-3-(3-(8-methyl-9H-purin-6-yl)pyridin-2-ylamino)phenyl)propane-1-sulfonamide was synthesized from 6-(2-fluoropyridin-3-yl)-8-methyl-9-(tetrahydro-2H-pyran-2-yl)-9H-purine (Example 3, Step 2) and N-(3-amino-2,4-difluorophenyl)propane-1-sulfonamide (Example 1, Step 7) in a similar manner as described in Example 1, Step 10.

¹H NMR (CDCl₃): δ 12.26 (1H, s), 11.18 (1H, s), 10.11 (1H, s), 9.74-9.72 (1H, m), 9.08 (1H, s), 8.35-8.33 (1H, m), 7.50-7.44 (1H, m), 7.04-6.99 (2H, m), 3.19-3.15 (2H, m), 2.78 (3H, s), 1.96-1.90 (2H, m), 1.02 (3H, t, J=7.2 Hz).

Example 4

N-(3-(3-(9H-purin-6-yl)pyridin-2-ylamino)-4-fluorophenyl)propane-1-sulfonamide

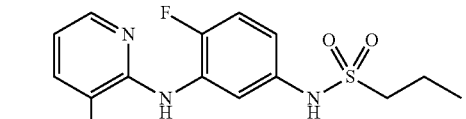

Step 1:
N-(4-fluoro-3-nitrophenyl)propane-1-sulfonamide

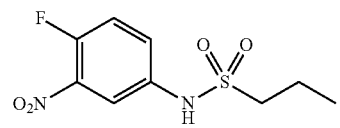

To a solution of 4-fluoro-3-nitroaniline (781 mg, 5 mmol) in 1,2-dichloroethane (8 mL) was added pyridine (8 mL), followed by propane-1-sulfonyl chloride (784 mg, 5.5 mmol) and the resulting reaction mixture was heated to 100° C. for 2 hrs. The mixture was diluted with water, extracted with CH₂Cl₂, washed with brine, dried over Na₂SO₄, filtered and concentrated in vacuo to afford the desired product (889 mg, 68%). The crude product was used for next step without further purification.

Step 2:
N-(3-amino-4-fluorophenyl)propane-1-sulfonamide

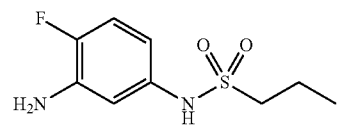 [SMILES: CCCS(=O)(=O)Nc1ccc(F)c([N+](=O)[O-])c1]

To a solution of N-(4-fluoro-3-nitrophenyl)propane-1-sulfonamide (680 mg, 2.6 mmol) in EtOH/H₂O (20 mL, 4/1) was added Fe (612 mg, 10.4 mmol), followed by NH₄Cl (209 mg, 3.9 mmol) and the resulting reaction mixture was heated to 80° C. for 2 hrs. The mixture was filtered, dried over Na₂SO₄, filtered and concentrated in vacuo. The residue was purified by column chromatography (petrol ether: EtOAc=3:1 to 2:1) to afford the desired product (513 mg, 85%).

¹H NMR (CDCl₃): δ 6.95-6.91 (1H, m), 6.77-6.75 (1H, m), 6.66 (1H, br), 6.49-6.46 (1H, m), 3.86 (2H, br), 3.07-3.03 (2H, m), 1.88-1.82 (2H, m), 1.03 (3H, t, J=7.2 Hz).

Step 3: N-(4-fluoro-3-(3-(9-(tetrahydro-2H-pyran-2-yl)-9H-purin-6-yl)pyridin-2-ylamino)phenyl)propane-1-sulfonamide

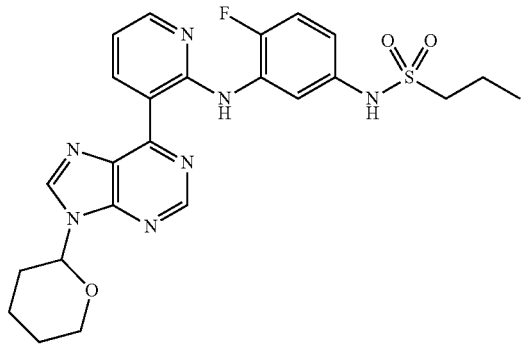 [SMILES: CCCS(=O)(=O)Nc1ccc(F)c(Nc2ncccc2-c2ncnc3c2ncn3C2CCCCO2)c1]

N-(4-fluoro-3-(3-(9-(tetrahydro-2H-pyran-2-yl)-9H-purin-6-yl)pyridin-2-ylamino)phenyl)propane-1-sulfonamide was synthesized from 6-(2-fluoropyridin-3-yl)-9-(tetrahydro-2H-pyran-2-yl)-9H-purine (Example 1, Step 9) and N-(3-amino-4-fluorophenyl)propane-1-sulfonamide (Example 4, Step 2) in a similar manner as described in Example 1, Step 10.

$^1$H NMR (CDCl$_3$): δ 12.89 (1H, d, J=2.0 Hz), 9.76-9.74 (1H, m), 9.06 (1H, s), 8.75-8.72 (1H, m), 8.40-8.38 (2H, m), 7.13-7.00 (2H, m), 6.94-6.90 (1H, m), 6.29 (1H, s), 5.91-5.88 (1H, m), 4.25-4.21 (1H, m), 3.87-3.81 (1H, m), 3.14-3.10 (2H, m), 2.23-1.69 (8H, m), 1.05 (3H, t, J=7.2 Hz).

Step 4: N-(3-(3-(9H-purin-6-yl)pyridin-2-ylamino)-4-fluorophenyl)propane-1-sulfonamide

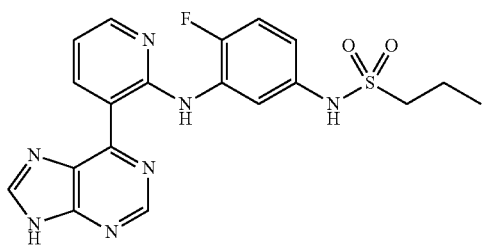

N-(3-(3-(9H-purin-6-yl)pyridin-2-ylamino)-4-fluorophenyl)propane-1-sulfonamide was synthesized from N-(4-fluoro-3-(3-(9-(tetrahydro-2H-pyran-2-yl)-9H-purin-6-yl)pyridin-2-ylamino)phenyl)propane-1-sulfonamide (Example 4, Step 3) in a similar manner as described in Example 1, Step 11.

$^1$H NMR (DMSO-d$_6$): δ 12.81 (1H, d, J=1.6 Hz), 9.81-9.70 (2H, m), 9.02 (1H, s), 8.72 (1H, s), 8.64-8.62 (1H, m), 8.38-8.36 (1H, m), 7.24 (1H, dd, J=8.8 Hz, 11.2 Hz), 7.11 (1H, dd, J=4.8 Hz, 8.0 Hz), 6.85-6.81 (1H, m), 3.08-3.04 (2H, m), 1.76-1.67 (2H, m), 0.94 (3H, t, J=7.2 Hz).

Example 5

N-(3-(3-(9H-purin-6-yl)pyridin-2-ylamino)-4-chlorophenyl)propane-1-sulfonamide

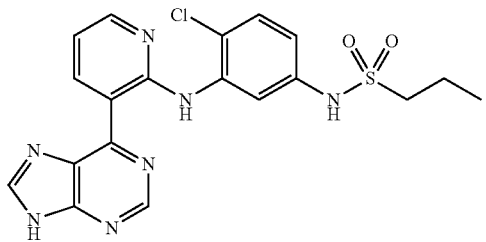 [SMILES: CCCS(=O)(=O)Nc1ccc(F)c(Nc2ncccc2-c2ncnc3[nH]cnc23)c1]

Step 1: N-(4-chloro-3-nitrophenyl)propane-1-sulfonamide

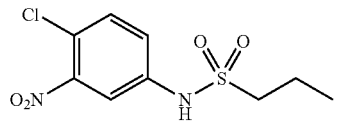

N-(4-chloro-3-nitrophenyl)propane-1-sulfonamide was synthesized from 4-chloro-3-nitroaniline and propane-1-sulfonyl chloride in a similar manner as described in Example 4, Step 1.

$^1$H NMR (CDCl$_3$): δ 7.75 (1H, d, J=2.4 Hz), 7.51 (1H, d, J=8.8 Hz), 7.42-7.39 (1H, m), 3.17-3.13 (2H, m), 1.93-1.83 (2H, m), 1.06 (3H, t, J=7.2 Hz).

Step 2: N-(3-amino-4-chlorophenyl)propane-1-sulfonamide

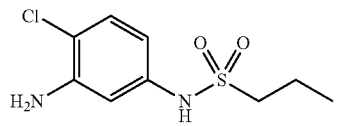 [SMILES: CCCS(=O)(=O)Nc1ccc(Cl)c([N+](=O)[O-])c1]

N-(3-amino-4-chlorophenyl)propane-1-sulfonamide was synthesized from N-(4-chloro-3-nitrophenyl)propane-1-sulfonamide (Example 5, Step 1) in a similar manner as described in Example 4, Step 2.

$^1$H NMR (CDCl$_3$): δ 7.17 (1H, 1H, J=8.4 Hz), 6.87 (1H, br), 6.74 (1H, d, J=2.8 Hz), 6.50-6.47 (1H, m), 4.18 (2H, br), 3.10-3.06 (2H, m), 1.89-1.79 (2H, m), 1.02 (3H, t, J=7.2 Hz).

Step 3: N-(4-chloro-3-(3-(9-(tetrahydro-2H-pyran-2-yl)-9H-purin-6-yl)pyridin-2-ylamino)phenyl)propane-1-sulfonamide

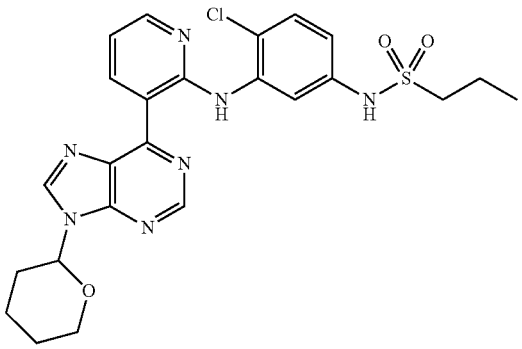 [SMILES: CCCS(=O)(=O)Nc1ccc(Cl)c(Nc2ncccc2-c2ncnc3c2ncn3C2CCCCO2)c1]

N-(4-chloro-3-(3-(9-(tetrahydro-2H-pyran-2-yl)-9H-purin-6-yl)pyridin-2-ylamino)phenyl)propane-1-sulfonamide was synthesized from 6-(2-fluoropyridin-3-yl)-9-(tetrahydro-2H-pyran-2-yl)-9H-purine (Example 1, Step 9) and N-(3-amino-4-chlorophenyl)propane-1-sulfonamide (Example 5, Step 2) in a similar manner as described in Example 1, Step 10.

$^1$H NMR (CDCl$_3$): δ 12.92 (1H, s), 9.71 (1H, dd, J=1.6 Hz, 7.6 Hz), 9.08 (1H, s), 8.80 (1H, d, J=2.8 Hz), 8.42-8.39 (2H, m), 7.39 (1H, d, J=8.8 Hz), 7.05 (1H, dd, J=4.8 Hz, 8.0 Hz), 6.93 (1H, dd, J=2.8 Hz, 8.8 Hz), 6.40 (1H, s), 5.93-5.90 (1H, m), 4.27-4.23 (1H, m), 3.89-3.83 (1H, m), 3.19-3.15 (2H, m), 2.37-1.71 (8H, m), 1.07 (3H, t, J=7.2 Hz).

Step 4: N-(3-(3-(9H-purin-6-yl)pyridin-2-ylamino)-4-chlorophenyl)propane-1-sulfonamide

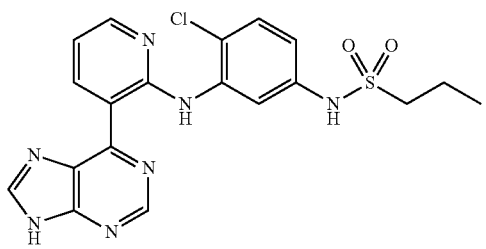 [SMILES: CCCS(=O)(=O)Nc1ccc(Cl)c(Nc2ncccc2-c2ncnc3[nH]cnc23)c1]

N-(3-(3-(9H-purin-6-yl)pyridin-2-ylamino)-4-chlorophenyl)propane-1-sulfonamide was synthesized from N-(4-chloro-3-(3-(9-(tetrahydro-2H-pyran-2-yl)-9H-purin-6-yl)pyridin-2-ylamino)phenyl)propane-1-sulfonamide (Example 5, Step 3) in a similar manner as described in Example 1, Step 11.

$^1$H NMR (CDCl$_3$): δ 13.90 (1H, br), 13.03 (1H, br), 9.91-9.81 (2H, m), 9.10 (1H, s), 8.80 (1H, d, J=2.4 Hz), 8.74 (1H, s), 8.40 (1H, dd, J=2.0 Hz, 4.8 Hz), 7.45 (1H, d, J=8.8 Hz), 7.16 (1H, dd, J=4.8 Hz, 8.0 Hz), 6.85 (1H, dd, J=2.8 Hz, 8.8 Hz), 3.16-3.12 (2H, m), 1.77-1.68 (2H, m), 0.96 (3H, t, J=7.2 Hz).

Example 6

N-(3-(3-(9H-purin-6-yl)pyridin-2-ylamino)-4-methylphenyl)propane-1-sulfonamide

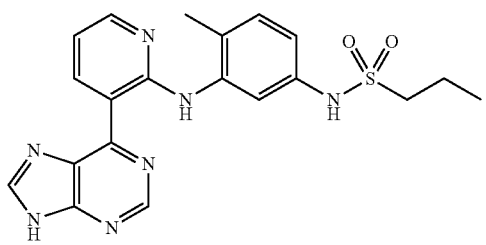 [SMILES: CCCS(=O)(=O)Nc1ccc(C)c(Nc2ncccc2-c2ncnc3[nH]cnc23)c1]

Step 1: N-(4-methyl-3-nitrophenyl)propane-1-sulfonamide

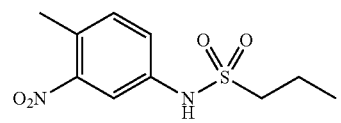

N-(4-methyl-3-nitrophenyl)propane-1-sulfonamide was synthesized from 4-methyl-3-nitroaniline and propane-1-sulfonyl chloride in a similar manner as described in Example 4, Step 1.

Step 2: N-(3-amino-4-methylphenyl)propane-1-sulfonamide

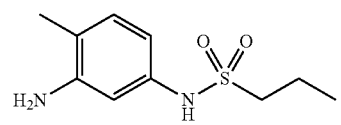 [SMILES: CCCS(=O)(=O)Nc1ccc(C)c([N+](=O)[O-])c1]

N-(3-amino-4-methylphenyl)propane-1-sulfonamide was synthesized from N-(4-methyl-3-nitrophenyl)propane-1-sulfonamide (Example 6, Step 1) in a similar manner as described in Example 4, Step 2.

$^1$H NMR (CDCl$_3$): δ 6.97 (1H, d, J=8.0 Hz), 6.62 (1H, d, J=2.0 Hz), 6.45 (1H, dd, 0.1=2.4 Hz, 8.0 Hz), 3.69 (2H, br), 3.06-3.03 (2H, m), 1.89-1.79 (2H, m), 1.01 (3H, t, J=7.6 Hz).

Step 3: N-(4-methyl-3-(3-(9-(tetrahydro-2H-pyran-2-yl)-9H-purin-6-yl)pyridin-2-ylamino)phenyl)propane-1-sulfonamide

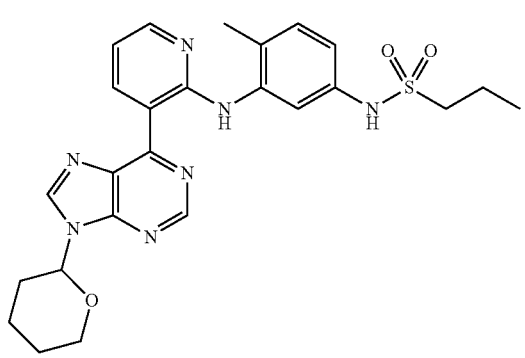 [SMILES: CCCS(=O)(=O)Nc1ccc(C)c(Nc2ncccc2-c2ncnc3c2ncn3C2CCCCO2)c1]

N-(4-methyl-3-(3-(9-(tetrahydro-2H-pyran-2-yl)-9H-purin-6-yl)pyridin-2-ylamino)phenyl)propane-1-sulfonamide was synthesized from 6-(2-fluoropyridin-3-yl)-9-(tetrahydro-2H-pyran-2-yl)-9H-purine (Example 1, Step 9) and N-(3-amino-4-methylphenyl)propane-1-sulfonamide (Example 6, Step 2) in a similar manner as described in Example 1, Step 10.

Step 4: N-(3-(3-(9H-purin-6-yl)pyridin-2-ylamino)-4-methylphenyl)propane-1-sulfonamide

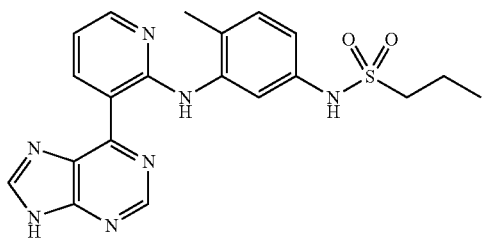 [SMILES: CCCS(=O)(=O)Nc1ccc(C)c(Nc2ncccc2-c2ncnc3[nH]cnc23)c1]

N-(3-(3-(9H-purin-6-yl)pyridin-2-ylamino)-4-methylphenyl)propane-1-sulfonamide was synthesized from N-(4-methyl-3-(3-(9-(tetrahydro-2H-pyran-2-yl)-9H-purin-6-yl)pyridin-2-ylamino)phenyl)propane-1-sulfonamide (Example 6, Step 3) in a similar manner as described in Example 1, Step 11.

$^1$H NMR (CDCl$_3$): δ 12.22 (1H, s), 9.77 (2H, dd, J=1.6 Hz, 8.0 Hz), 9.01 (1H, s), 8.39-8.38 (2H, m), 8.28 (1H, s), 7.20 (1H, d, J=8.0 Hz), 7.00-6.92 (2H, m), 6.33 (1H, s), 3.18-3.14 (2H, m), 1.95-1.89 (2H, m), 1.05 (3H, t, J=7.2 Hz).

Example 7

N-(3-(3-(9H-purin-6-yl)pyridin-2-ylamino)-4-chloro-2-fluorophenyl)propane-1-sulfonamide

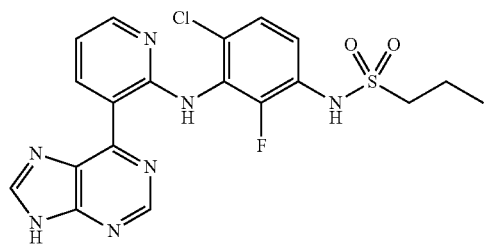 [SMILES: CCCS(=O)(=O)Nc1ccc(Cl)c(Nc2ncccc2-c2ncnc3[nH]cnc23)c1F]

Step 1: benzyl 3-amino-6-chloro-2-fluorobenzoate

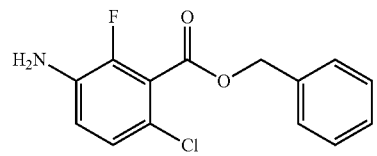 [SMILES: Nc1ccc(Cl)c(C(=O)OCc2ccccc2)c1F]

To a solution of 4-chloro-2-fluoroaniline (5.0 g, 34.3 mmol) in anhydrous THF (50 mL) was added n-BuLi (2.5 M, 14.7 mL) at −78° C. under N$_2$ atmosphere. After stirred at −78° C. for 20 min, 1,2-Bio(chlorodimethylsilyl)ethane (7.8 g, 36.1 mmol) in THF (20 mL) was added drop-wise, followed by n-BuLi (2.5 M, 15.6 mL). The mixture was warmed to room temperature for 1 hrs, then n-BuLi (2.5 M, 15.6 mL) was added again at −78° C. and continued to stirring at −78° C. for 1 hrs. Benzyl carbonochloridate (7.4 g, 41.2 mmol) was added and the mixture was warmed to room temperature for 1 hrs. The resulting reaction mixture was quenched with water, extracted with EtOAc, washed with brine, dried over Na$_2$SO$_4$, filtered and concentrated in vacuo. The residue was purified with column chromatography (petrol ether: EtOAc=5:1 to 3:1) to afford the desired product (4.3 g, 45%).

$^1$H NMR (CDCl$_3$): δ 7.48-7.37 (5H, m), 7.07 (1H, dd, 0.1=2.0 Hz, 8.0 Hz), 6.87 (1H, t, J=8.0 Hz), 5.61 (2H, s), 3.81 (1H, s).

Step 2: benzyl 6-chloro-2-fluoro-3-(N-(propylsulfonyl)propylsulfonamido)benzoate

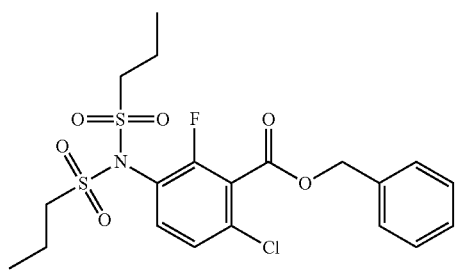 [SMILES: CCCS(=O)(=O)N(c1ccc(Cl)c(C(=O)OCc2ccccc2)c1F)S(=O)(=O)CCC]

To a solution of benzyl 3-amino-6-chloro-2-fluorobenzoate (4.3 g, 15.4 mmol) in CH₂Cl₂ (30 mL) was added Et₃N (5.4 mL, 38.5 mmol), followed by propane-1-sulfonyl chloride (3.6 mL, 32.3 mmol) and the resulting reaction mixture was stirred at room temperature for 3 hrs. The mixture was diluted with water, extracted with CH₂Cl₂, washed with brine, dried over Na₂SO₄, filtered and concentrated in vacuo. The residue was purified with column chromatography (Petrol ether: EtOAc=7:1 to 5:1) to afford the desired product (5.5 g, 72%).

¹H NMR (CDCl₃): δ 7.45-7.28 (7H, m), 5.42 (2H, s), 3.66-3.58 (2H, m), 3.52-3.43 (2H, m), 1.08 (6H, t, J=8.0 Hz).

Step 3: 6-chloro-2-fluoro-3-(propylsulfonamido)benzoic acid

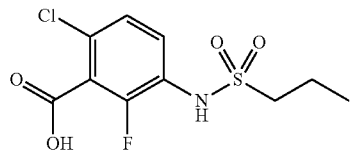 [SMILES: CCCS(=O)(=O)Nc1ccc(Cl)c(C(=O)O)c1F]

To a solution of benzyl 6-chloro-2-fluoro-3-(N-(propylsulfonyl)propylsulfonamido)benzoate (5.5 g, 11.1 mmol) in THF (20 mL) was added KOH aqueous (1M, 100 mL) and the resulting reaction mixture was heated to 100° C. for 16 hrs. The solvent was removed in vacuo and the residue was neutralized with HCl (6N) to pH=1 and filtered. The solid was washed with water and dried to afford the desired product (2.2 g, 68%).

¹H NMR (DMSO-d₆): δ 9.93 (1H, s), 7.49 (1H, t, J=8.0 Hz), 7.38 (1H, dd, J=8.0 Hz, J=2.0 Hz), 3.16-3.11 (2H, m), 1.78-1.68 (2H, m), 0.97 (3H, t, J=8.0 Hz).

Step 4: N-(3-amino-4-chloro-2-fluorophenyl)propane-1-sulfonamide

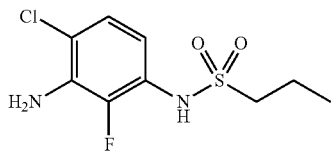 [SMILES: CCCS(=O)(=O)Nc1ccc(Cl)c(N)c1F]

N-(3-amino-4-chloro-2-fluorophenyl)propane-1-sulfonamide was synthesized from 6-chloro-2-fluoro-3-(propylsulfonamido)benzoic acid (Example 7, Step 3) in a similar manner as described in Example 1, Step 7.

¹H NMR (CDCl₃): δ 7.02 (1H, dd, J=2.0 Hz, 8.0 Hz), 6.90 (1H, t, J=8.0 Hz), 6.38 (1H, s), 4.11 (2H, s); 3.10-3.07 (2H, m), 1.89-1.82 (2H, m), 1.02 (3H, t, J=8.0 Hz).

Step 5: N-(4-chloro-2-fluoro-3-(3-(9-(tetrahydro-2H-pyran-2-yl)-9H-purin-6-yl)pyridin-2-ylamino)phenyl)propane-1-sulfonamide

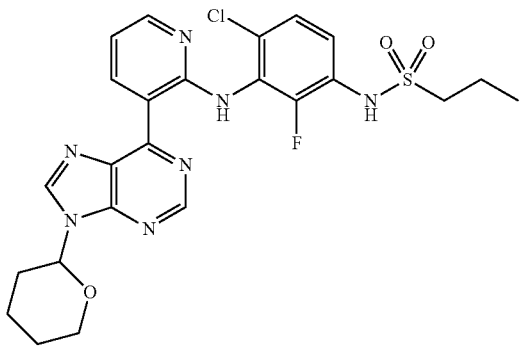 [SMILES: CCCS(=O)(=O)Nc1ccc(Cl)c(Nc2ncccc2-c2ncnc3c2ncn3C2CCCCO2)c1F]

N-(4-chloro-2-fluoro-3-(3-(9-(tetrahydro-2H-pyran-2-yl)-9H-purin-6-yl)pyridin-2-ylamino)phenyl)propane-1-sulfonamide was synthesized from 6-(2-fluoropyridin-3-yl)-9-(tetrahydro-2H-pyran-2-yl)-9H-purine (Example 1, Step 9) and N-(3-amino-4-chloro-2-fluorophenyl)propane-1-sulfonamide (Example 7, Step 4) in a similar manner as described in Example 1, Step 10.

¹H NMR (CDCl₃): δ 11.83 (1H, s), 9.66 (1H, dd, J=2.0 Hz, 8.0 Hz), 9.03 (1H, s), 8.41 (1H, s), 8.22-8.21 (1H, m), 7.44-7.42 (1H, m), 7.28-7.27 (1H, m), 6.97-6.96 (1H, m), 6.47 (1H, s), 5.91 (1H, d, 0.1=2.8 Hz), 4.24-4.22 (1H, m), 3.89-3.82 (1H, m), 3.13-3.11 (2H, m), 2.32-2.12 (5H, m), 2.02-1.88 (4H, m), 1.01 (3H, t, J=8.0 Hz).

Step 6: N-(3-(3-(9H-purin-6-yl)pyridin-2-ylamino)-4-chloro-2-fluorophenyl)propane-1-sulfonamide

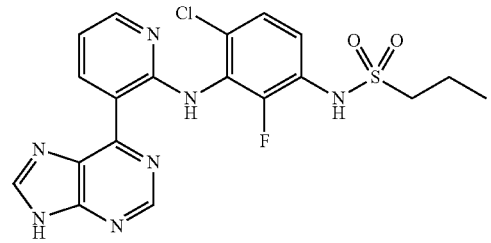 [SMILES: CCCS(=O)(=O)Nc1ccc(Cl)c(Nc2ncccc2-c2ncnc3[nH]cnc23)c1F]

N-(3-(3-(9H-purin-6-yl)pyridin-2-ylamino)-4-chloro-2-fluorophenyl)propane-1-sulfonamide was synthesized from N-(4-chloro-2-fluoro-3-(3-(9-(tetrahydro-2H-pyran-2-yl)-9H-purin-6-yl)pyridin-2-ylamino)phenyl)propane-1-sulfonamide (Example 7, Step 5) in a similar manner as described in Example 1, Step 11.

¹H NMR (DMSO-d₆): δ 13.82 (1H, s), 11.86 (1H, s), 9.88 (1H, s), 9.79 (1H, s), 9.04 (1H, s), 8.73 (1H, s), 8.18 (1H, dd, J=1.6 Hz, 4.8 Hz), 7.38-7.33 (1H, m), 7.31-7.29 (1H, m), 7.03 (1H, dd, J=2.0 Hz, 8.0 Hz), 3.13-3.10 (2H, m), 1.83-1.78 (4H, m), 0.96 (3H, t, J=8.0 Hz).

51

Example 8

N-(3-(3-(9H-purin-6-yl)pyridin-2-ylamino)-2-chloro-4-fluorophenyl)propane-1-sulfonamide

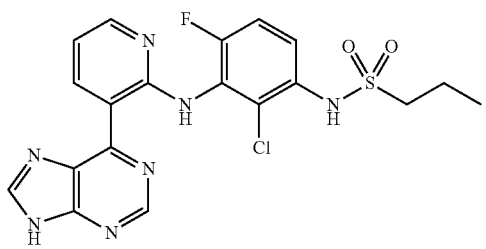 [SMILES: CCCS(=O)(=O)Nc1ccc(F)c(Nc2ncccc2-c2ncnc3[nH]cnc23)c1Cl]

Step 1: 2-chloro-6-fluoro-3-nitrobenzoic acid

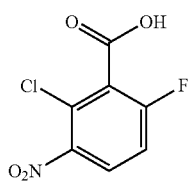 [SMILES: O=C(O)c1c(F)ccc([N+](=O)[O-])c1Cl]

To a solution of methyl 2-chloro-6-fluorobenzoic acid (5.0 g, 28.6 mmol) in con.H₂SO₄ (15 mL) was added nitric acid (98%) (1.3 mL, 35.3 mmol) at 0° C. and the resulting reaction mixture was stirred at room temperature for 30 min. The mixture was dropped into ice-water (80 mL) and extracted with EtOAc. The extract was washed with brine, dried over Na₂SO₄, filtered and concentrated in vacuo to afford the desired product (5.7 g, 90%).

¹H NMR (CDCl₃): δ 8.12-8.08 (1H, m), 7.28 (1H, s), 7.12 (1H, t, J=8.0 Hz).

Step 2: 3-amino-2-chloro-6-fluorobenzoic acid

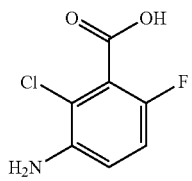

To a solution of 2-chloro-6-fluoro-3-nitrobenzoic acid (5.7 g, 26 mmol) in THF (150 mL) was added zinc (17.0 g, 260 mmol), followed by saturated aqueous NH₄Cl (100 mL) and the resulting reaction mixture was room temperature for 20 hrs. The mixture was filtered, extracted with EtOAc, washed with brine, dried over Na₂SO₄, filtered and concentrated in vacuo to afford the desired product (2.7 g, 55%).

¹H NMR (CDCl₃): δ 6.88 (1H, t, J=8.0 Hz), 6.76-6.71 (1H, m), 4.02 (2H, s).

52

Step 3: Methyl 3-amino-2-chloro-6-fluorobenzoate

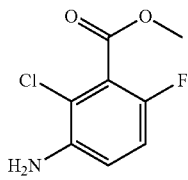

To a solution of 3-amino-2-chloro-6-fluorobenzoic acid (5.5 g, 11.1 mmol) in MeOH (60 mL) was added con. H₂SO₄ (3.0 mL) and the resulting reaction mixture was heated to refluxing for 24 hrs. The solvent was removed in vacuo and the residue was neutralized with saturated aqueous NaHCO₃ to pH=8 and extracted with EtOAc, washed with brine, dried over Na₂SO₄, filtered and concentrated in vacuo. The residue was purified by column chromatography (petrol ether: EtOAc=4:1 to 2:1) to afford the desired product (1.1 g, 41%).

¹H NMR (CDCl₃): δ 6.82 (1H, t, J=8.0 Hz), 6.69-6.63 (1H, m), 4.02 (2H, s), 3.97 (3H, s).

Step 4: Methyl 2-chloro-6-fluoro-3-(N-(propylsulfonyl)propylsulfonamido)benzoate

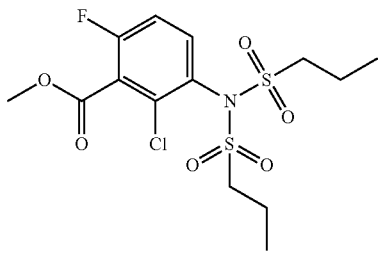 [SMILES: CCCS(=O)(=O)N(c1ccc(F)c(C(=O)OC)c1Cl)S(=O)(=O)CCC]

Methyl 2-chloro-6-fluoro-3-(N-(propylsulfonyl)propylsulfonamido)benzoate was synthesized from Methyl 3-amino-2-chloro-6-fluorobenzoate (Example 8, Step 3) and propane-1-sulfonyl chloride in a similar manner as described in Example 7, Step 2.

¹H NMR (CDCl₃): δ 7.25-7.18 (2H, m), 4.01 (3H, s), 3.66-3.58 (4H, m), 3.52-3.43 (4H, m), 1.08 (6H, t, J=8.0 Hz).

Step 5: 2-chloro-6-fluoro-3-(propylsulfonamido)benzoic acid

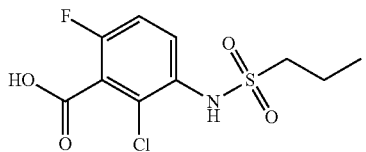 [SMILES: CCCS(=O)(=O)Nc1ccc(F)c(C(=O)O)c1Cl]

2-chloro-6-fluoro-3-(propylsulfonamido)benzoic acid was synthesized from Methyl 2-chloro-6-fluoro-3-(N-(propylsulfonyl)propylsulfonamido)benzoate (Example 8, Step 4) and propane-1-sulfonyl chloride in a similar manner as described in Example 7, Step 3.

¹H NMR (DMSO-d₆): δ 10.12 (1H, s), 7.39 (1H, m), 7.31 (1H, t, J=8.0 Hz), 3.16-3.13 (2H, m), 1.78-1.69 (2H, m), 0.98 (3H, t, J=8.0 Hz).

Step 6: N-(3-amino-2-chloro-4-fluorophenyl)propane-1-sulfonamide

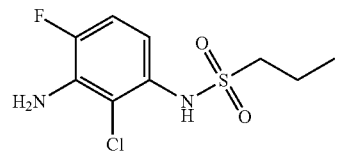 [SMILES: CCCS(=O)(=O)Nc1ccc(F)c(N)c1Cl]

N-(3-amino-2-chloro-4-fluorophenyl)propane-1-sulfonamide was synthesized from 2-chloro-6-fluoro-3-(propylsulfonamido)benzoic acid (Example 8, Step 5) and propane-1-sulfonyl chloride in a similar manner as described in Example 1, Step 7.

¹H NMR (CDCl₃): δ 7.02 (1H, m), 6.95 (1H, t, J=8.0 Hz), 6.36 (1H, s), 4.18 (2H, s), 3.06-3.02 (2H, m), 1.88-1.84 (2H, m), 1.02 (3H, t, J=8.0 Hz).

Step 7: N-(2-chloro-4-fluoro-3-(3-(9-(tetrahydro-2H-pyran-2-yl)-9H-purin-6-yl)pyridin-2-ylamino)phenyl)propane-1-sulfonamide

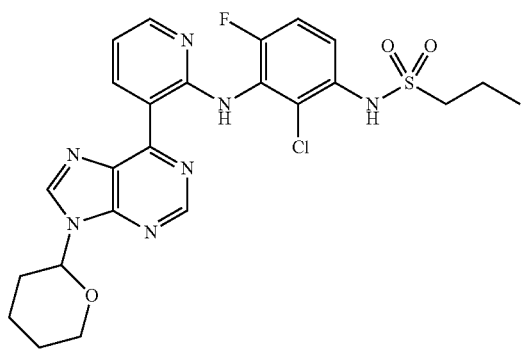

N-(2-chloro-4-fluoro-3-(3-(9-(tetrahydro-2H-pyran-2-yl)-9H-purin-6-yl)pyridin-2-ylamino)phenyl)propane-1-sulfonamide was synthesized from 6-(2-fluoropyridin-3-yl)-9-(tetrahydro-2H-pyran-2-yl)-9H-purine (Example 1, Step 9) and N-(3-amino-2-chloro-4-fluorophenyl)propane-1-sulfonamide (Example 8, Step 6) in a similar manner as described in Example 1, Step 10.

¹H NMR (CDCl₃): δ 11.79 (1H, s), 9.58 (1H, dd, J=2.0 Hz, 8.0 Hz), 9.03 (1H, s), 8.41 (1H, s), 8.12-8.08 (1H, m), 7.44-7.42 (1H, m), 7.18-7.16 (1H, m), 6.98-6.96 (1H, m), 6.47 (1H, s), 5.91 (1H, d, J=2.8 Hz), 4.24-4.22 (1H, m), 3.86-3.82 (1H, m), 3.12-3.11 (2H, m), 2.32-2.12 (5H, m), 2.02-1.89 (4H, m), 0.98 (3H, t, J=8.0 Hz).

Step 8: N-(3-(3-(9H-purin-6-yl)pyridin-2-ylamino)-2-chloro-4-fluorophenyl)propane-1-sulfonamide

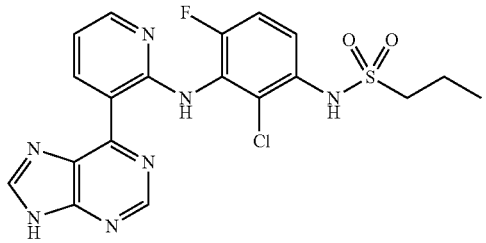 [SMILES: CCCS(=O)(=O)Nc1ccc(F)c(Nc2ncccc2-c2ncnc3[nH]cnc23)c1Cl]

N-(3-(3-(9H-purin-6-yl)pyridin-2-yl amino)-2-chloro-4-fluorophenyl)propane-1-sulfonamide was synthesized from N-(2-chloro-4-fluoro-3-(3-(9-(tetrahydro-2H-pyran-2-yl)-9H-purin-6-yl)pyridin-2-ylamino)phenyl)propane-1-sulfonamide (Example 8, Step 7) in a similar manner as described in Example 1, Step 11.

¹H NMR (DMSO-d₆): δ 13.89 (1H, s), 11.88 (1H, s), 9.88 (1H, s), 9.79 (1H, s), 9.04 (1H, s), 8.73 (1H, s), 8.19 (1H, dd, J=2.0 Hz, 8.0 Hz), 7.38-7.29 (2H, m), 7.03 (1H, dd, J=4.8 Hz, 8.0 Hz), 3.12-3.10 (2H, m), 1.82-1.79 (4H, m), 0.99 (3H, t, J=8.0 Hz).

Example 9

N-(3-(3-(9H-purin-6-yl)pyridin-2-ylamino)-4-chloro-2-fluorophenyl)-3-fluoropropane-1-sulfonamide

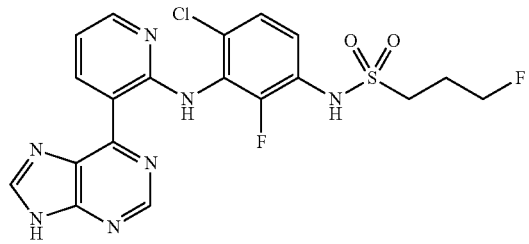

Step 1: N-(3-(3-(9H-purin-6-yl)pyridin-2-ylamino)-4-chloro-2-fluorophenyl)-3-fluoropropane-1-sulfonamide

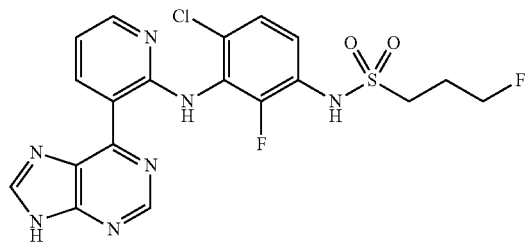 [SMILES: O=S(=O)(CCCF)Nc1ccc(Cl)c(Nc2ncccc2-c2ncnc3[nH]cnc23)c1F]

To a solution of 6-(2-fluoropyridin-3-yl)-9-(tetrahydro-2H-pyran-2-yl)-9H-purine (111 mg, 0.4 mmol) in anhydrous THF (20 mL) was added N-(3-amino-4-chloro-2-fluorophenyl)-3-fluoropropane-1-sulfonamide (100 mg, 0.4 mmol), followed by NaHMDS (2M, 0.6 mL) and the resulting reaction mixture was stirred at 60° C. for 2 hrs. The mixture was quenched with HCl (3N) to pH=2, neutralized with saturated aqueous NaHCO$_3$ to pH=8 and extracted with EtOAc, washed with brine, dried over Na$_2$SO$_4$, filtered and concentrated in vacuo. The residue was purified with column chromatography (petrol ether: EtOAc=1:1 to 1:2) to afford the desired product (98 mg, 47%).

$^1$H NMR (DMSO-d$_6$): δ 13.88 (1H, s), 11.77 (1H, s), 9.96 (1H, s), 9.71 (1H, s), 9.04 (1H, s), 8.73 (1H, s), 8.18 (1H, d, J=4.8 Hz), 7.42 (1H, d, J=8.0 Hz), 7.30 (1H, t, J=8.0 Hz), 7.03 (1H, dd, J=2.0 Hz, 8.0 Hz), 4.60 (1H, t, J=6.0 Hz), 4.48 (1H, t, J=6.0 Hz), 3.25-3.21 (2H, m), 2.05-1.99 (2H, m).

Example 10

N-(3-(3-(9H-purin-6-yl)pyridin-2-ylamino)-2,4-difluorophenyl)-3-fluoropropane-1-sulfonamide

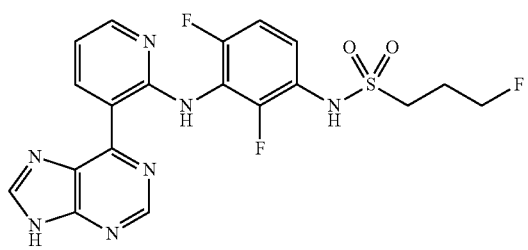 [SMILES: O=S(=O)(CCCF)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)-3-fluoropropane-1-sulfonamide

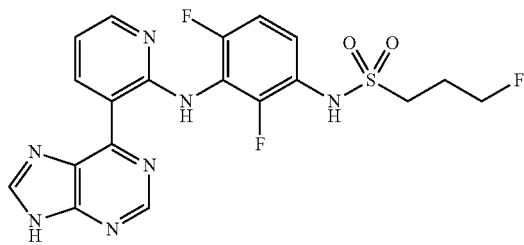 [SMILES: O=S(=O)(CCCF)Nc1ccc(F)c(Nc2ncccc2-c2ncnc3[nH]cnc23)c1F]

N-(3-(3-(9H-purin-6-yl)pyridin-2-ylamino)-2,4-difluorophenyl)-3-fluoropropane-1-sulfonamide was synthesized from 6-(2-fluoropyridin-3-yl)-9-(tetrahydro-2H-pyran-2-yl)-9H-purine and N-(3-amino-2,4-difluorophenyl)-3-fluoropropane-1-sulfonamide in a similar manner as described in Example 9, Step 1.

$^1$H NMR (DMSO-d$_6$): δ 13.88 (1H, s), 11.57 (1H, s), 9.92 (1H, s), 9.68 (1H, s), 9.03 (1H, s), 8.73 (1H, s), 8.19 (1H, d, J=4.8 Hz), 7.27-7.32 (1H, m), 7.19-7.22 (1H, m), 7.02-7.06 (1H, m), 4.60 (1H, t, J=6.0 Hz), 4.48 (1H, t, J=6.0 Hz), 3.21-3.25 (2H, m), 2.05-2.15 (2H, m).

Example 11

N-(3-(3-(9H-purin-6-yl)pyridin-2-ylamino)-2,4-difluorophenyl)-1-chloromethanesulfonamide

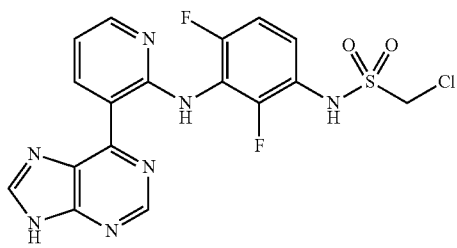 [SMILES: O=S(=O)(CCl)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)-1-chloromethanesulfonamide

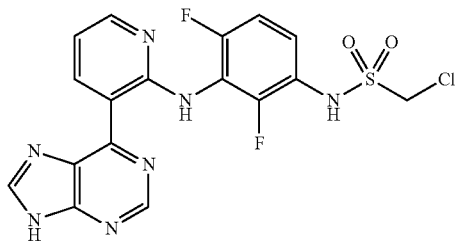 [SMILES: O=S(=O)(CCl)Nc1ccc(F)c(Nc2ncccc2-c2ncnc3[nH]cnc23)c1F]

N-(3-(3-(9H-purin-6-yl)pyridin-2-ylamino)-2,4-difluorophenyl)-1-chloromethanesulfonamide was synthesized from 6-(2-fluoropyridin-3-yl)-9-(tetrahydro-2H-pyran-2-yl)-9H-purine and N-(3-amino-2,4-difluorophenyl)-1-chloromethanesulfonamide in a similar manner as described in Example 9, Step 1.

$^1$H NMR (CD$_3$OD): δ 9.62 (1H, s), 9.01 (1H, s), 8.52 (1H, s), 8.16-8.15 (1H, m), 7.43-7.38 (1H, m), 7.10-7.06 (1H, m), 7.04-7.00 (1H, m), 4.80 (2H, m).

Example 12

N-(3-(3-(9H-purin-6-yl)pyridin-2-ylamino)-2,4-difluorophenyl)ethanesulfonamide

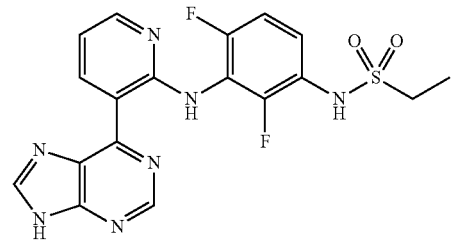 [SMILES: CCS(=O)(=O)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)ethanesulfonamide

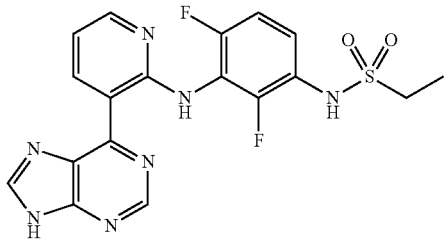 [SMILES: CCS(=O)(=O)Nc1ccc(F)c(Nc2ncccc2-c2ncnc3[nH]cnc23)c1F]

N-(3-(3-(9H-purin-6-yl)pyridin-2-ylamino)-2,4-difluorophenyl)ethanesulfonamide was synthesized from 6-(2-fluoropyridin-3-yl)-9-(tetrahydro-2H-pyran-2-yl)-9H-purine and N-(3-amino-2,4-difluorophenyl)ethanesulfonamide in a similar manner as described in Example 9, Step 1.

¹H NMR (CD₃OD): δ 9.20-9.18 (1H, m), 8.71 (1H, s), 8.21 (1H, s), 8.02-8.00 (1H, m), 7.24-7.18 (1H, m), 6.93-6.89 (1H, m), 6.83-6.78 (1H, m), 2.98-2.92 (2H, m), 1.31-1.26 (3H, m, J=4.8 Hz).

Example 13

N-(3-(3-(9H-purin-6-yl)pyridin-2-ylamino)-2,4-difluorophenyl)methanesulfonamide

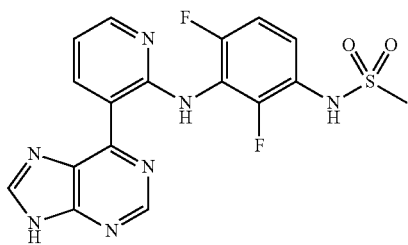 [SMILES: CS(=O)(=O)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)methanesulfonamide

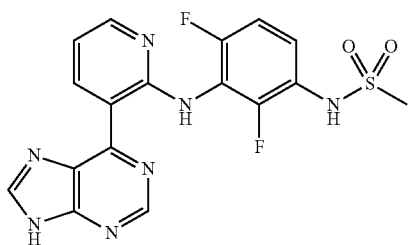 [SMILES: CS(=O)(=O)Nc1ccc(F)c(Nc2ncccc2-c2ncnc3[nH]cnc23)c1F]

N-(3-(3-(9H-purin-6-yl)pyridin-2-ylamino)-2,4-difluorophenyl)methanesulfonamide was synthesized from 6-(2-fluoropyridin-3-yl)-9-(tetrahydro-2H-pyran-2-yl)-9H-purine and N-(3-amino-2,4-difluorophenyl)methanesulfonamide in a similar manner as described in Example 9, Step 1.

¹H NMR (CDCl₃): δ 13.82 (1H, br), 11.53 (1H, s), 9.78-9.50 (2H, m), 9.00 (1H, s), 8.69 (1H, s), 8.19-8.15 (1H, m), 7.30-7.24 (1H, m), 7.23-7.12 (1H, m), 7.04-6.95 (1H, m), 3.00 (3H, s).

Example 14

N-(3-(3-(9H-purin-6-yl)pyridin-2-ylamino)-2,4-difluorophenyl)-3,4-difluorobenzenesulfonamide

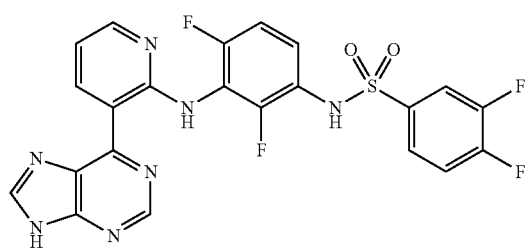 [SMILES: O=S(=O)(Nc1ccc(F)c(Nc2ncccc2-c2ncnc3[nH]cnc23)c1F)c1ccc(F)c(F)c1]

Step 1: N-(3-(3-(9H-purin-6-yl)pyridin-2-ylamino)-2,4-difluorophenyl)-3,4-difluorobenzenesulfonamide

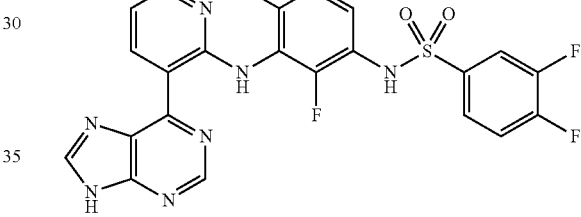

N-(3-(3-(9H-purin-6-yl)pyridin-2-ylamino)-2,4-difluorophenyl)-3,4-difluorobenzenesulfonamide was synthesized from 6-(2-fluoropyridin-3-yl)-9-(tetrahydro-2H-pyran-2-yl)-9H-purine and N-(3-amino-2,4-difluorophenyl)-3,4-difluorobenzenesulfonamide in a similar manner as described in Example 9, Step 1.

¹H NMR (DMSO-d₆): δ 13.82 (1H, br), 11.45 (1H, s), 10.33 (1H, s), 9.62 (1H, d, J=1.6 Hz), 8.97 (1H, s), 8.64 (1H, s), 8.14-8.13 (1H, m), 7.78-7.71 (1H, m), 7.69-7.62 (1H, m), 7.58-7.54 (1H, m), 7.19-7.08 (2H, m), 6.99-6.94 (1H, m).

Example 15

N-(3-(3-(9H-purin-6-yl)pyridin-2-ylamino)-2,4-difluorophenyl)benzenesulfonamide

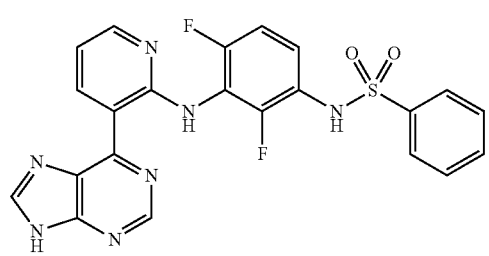 [SMILES: O=S(=O)(Nc1ccc(F)c(Nc2ncccc2-c2ncnc3[nH]cnc23)c1F)c1ccccc1]

Step 1: N-(3-(3-(9H-purin-6-yl)pyridin-2-ylamino)-2,4-difluorophenyl)benzenesulfonamide

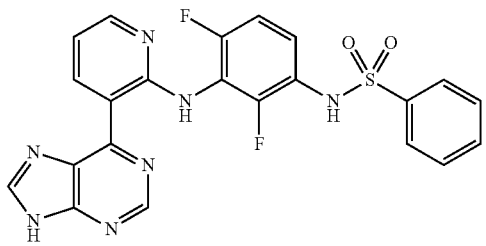 [SMILES: O=S(=O)(Nc1ccc(F)c(Nc2ncccc2-c2ncnc3[nH]cnc23)c1F)c1ccccc1]

N-(3-(3-(9H-purin-6-yl)pyridin-2-ylamino)-2,4-difluorophenyl)benzenesulfonamide was synthesized from 6-(2-fluoropyridin-3-yl)-9-(tetrahydro-2H-pyran-2-yl)-9H-purine and N-(3-amino-2,4-difluorophenyl)benzenesulfonamide in a similar manner as described in Example 9, Step 1.

$^1$H NMR (DMSO-d$_6$): δ 13.81 (1H, br), 11.43 (1H, s), 10.16 (1H, s), 9.62 (1H, m), 8.96 (1H, s), 8.68 (1H, s), 8.18-8.15 (1H, m), 7.75-7.70 (2H, m), 7.63-7.60 (1H, m), 7.58-7.51 (2H, m), 7.15-7.02 (2H, m), 7.00-6.95 (1H, m).

Example 16

N-(3-(3-(9H-purin-6-yl)pyridin-2-ylamino)-2,4-difluorophenyl)-4-(trifluoromethyl)benzenesulfonamide

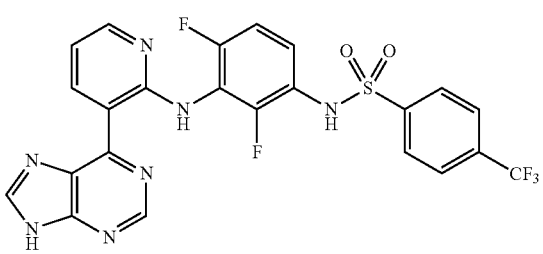 [SMILES: O=S(=O)(Nc1ccc(F)c(Nc2ncccc2-c2ncnc3[nH]cnc23)c1F)c1ccc(C(F)(F)F)cc1]

Step 1: N-(3-(3-(9H-purin-6-yl)pyridin-2-ylamino)-2,4-difluorophenyl)-4-(trifluoromethyl)benzenesulfonamide

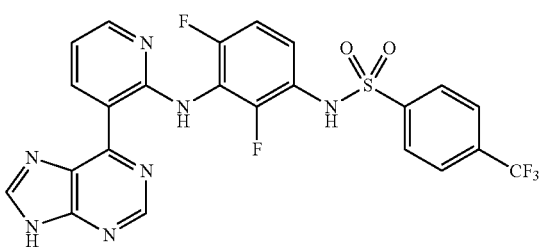 [SMILES: O=S(=O)(Nc1ccc(F)c(Nc2ncccc2-c2ncnc3[nH]cnc23)c1F)c1ccc(C(F)(F)F)cc1]

N-(3-(3-(9H-purin-6-yl)pyridin-2-ylamino)-2,4-difluorophenyl)-4-(trifluoromethyl)benzenesulfonamide was synthesized from 6-(2-fluoropyridin-3-yl)-9-(tetrahydro-2H-pyran-2-yl)-9H-purine and N-(3-amino-2,4-difluorophenyl)-4-(trifluoromethyl)benzenesulfonamide in a similar manner as described in Example 9, Step 1.

$^1$H NMR (DMSO-d$_6$): δ 13.88 (1H, s), 11.82 (1H, s), 9.96 (1H, s), 9.65 (1H, s), 8.98 (1H, s), 8.71 (1H, s), 8.11 (1H, d, J=2.8 Hz), 7.98 (2H, d, J=8.0 Hz), 7.88 (2H, d, J=8.0 Hz), 7.16-7.14 (2H, m), 7.00-6.99 (1H, m).

Example 17

N-(3-(3-(9H-purin-6-yl)pyridin-2-ylamino)-2,4-difluorophenyl)-4-chlorobenzenesulfonamide

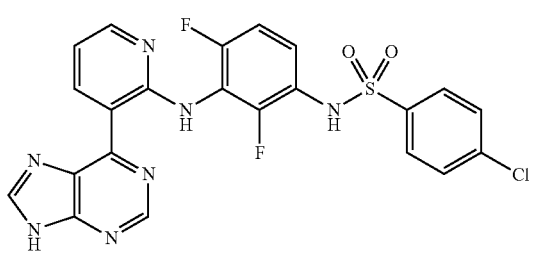 [SMILES: O=S(=O)(Nc1ccc(F)c(Nc2ncccc2-c2ncnc3[nH]cnc23)c1F)c1ccc(Cl)cc1]

Step 1: N-(3-(3-(9H-purin-6-yl)pyridin-2-ylamino)-2,4-difluorophenyl)-4-chlorobenzenesulfonamide

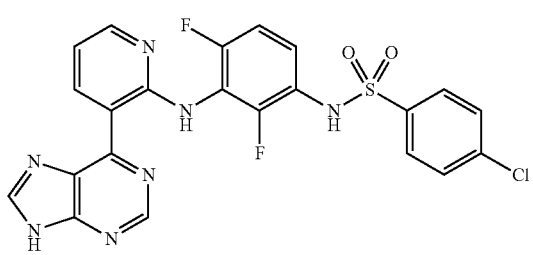 [SMILES: O=S(=O)(Nc1ccc(F)c(Nc2ncccc2-c2ncnc3[nH]cnc23)c1F)c1ccc(Cl)cc1]

N-(3-(3-(9H-purin-6-yl)pyridin-2-ylamino)-2,4-difluorophenyl)-4-chlorobenzenesulfonamide was synthesized from 6-(2-fluoropyridin-3-yl)-9-(tetrahydro-2H-pyran-2-yl)-9H-purine and N-(3-amino-2,4-difluorophenyl)-4-chlorobenzenesulfonamide in a similar manner as described in Example 9, Step 1.

$^1$H NMR (DMSO-d$_6$): δ 13.88 (1H, s), 11.52 (1H, s), 10.23 (1H, s), 9.75 (1H, s), 9.02 (1H, s), 8.75 (1H, s), 8.16 (1H, d, J=2.8 Hz), 7.68 (2H, d, J=8.0 Hz), 7.62 (2H, d, J=8.0 Hz), 7.16-7.13 (2H, m), 7.01-7.00 (1H, m).

Example 18

N-(3-(3-(9H-purin-6-yl)pyridin-2-ylamino)-2,4-difluorophenyl)-3,3,3-trifluoropropane-1-sulfon amide

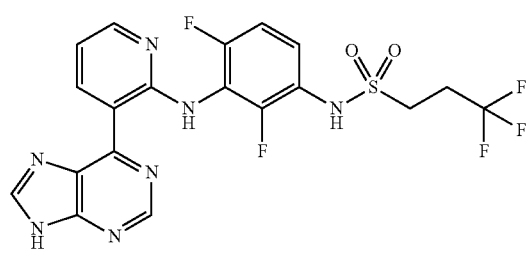 [SMILES: O=S(=O)(CCC(F)(F)F)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)-3,3,3-trifluoropropane-1-sulfonamide

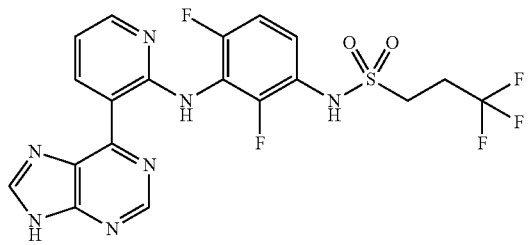 [SMILES: O=S(=O)(CCC(F)(F)F)Nc1ccc(F)c(Nc2ncccc2-c2ncnc3[nH]cnc23)c1F]

N-(3-(3-(9H-purin-6-yl)pyridin-2-ylamino)-2,4-difluorophenyl)-3,3,3-trifluoropropane-1-sulfon amide was synthesized from 6-(2-fluoropyridin-3-yl)-9-(tetrahydro-2H-pyran-2-yl)-9H-purine and N-(3-amino-2,4-difluorophenyl)-3,3,3-trifluoropropane-1-sulfonamide in a similar manner as described in Example 9, Step 1.

$^1$H NMR (CD$_3$OD): δ 9.56 (1H, br), 8.94 (1H, s), 8.45 (1H, s), 8.07-8.08 (1H, m), 7.29-7.33 (1H, m), 7.03 (1H, dd, J=1.6, 7.2 Hz), 6.93-6.96 (1H, m), 3.29-3.33 (2H, m), 2.64-2.71 (2H, m).

Example 19

N-(3-(3-(9H-purin-6-yl)pyridin-2-ylamino)-2,4-difluorophenyl)-2,2,2-trifluoromethanesulfonamide

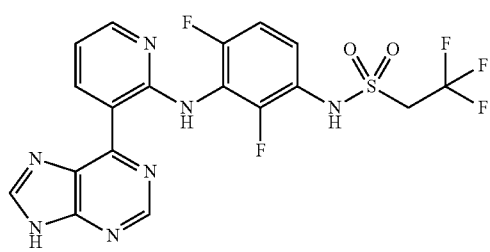 [SMILES: O=S(=O)(CC(F)(F)F)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)-2,2,2-trifluoroethanesulfonamide

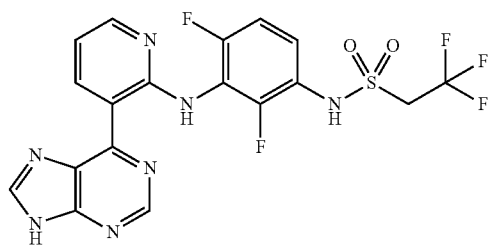 [SMILES: O=S(=O)(CC(F)(F)F)Nc1ccc(F)c(Nc2ncccc2-c2ncnc3[nH]cnc23)c1F]

To the solution of N$^1$-(3-(9H-purin-6-yl)pyridin-2-yl)-2,6-difluorobenzene-1,3-diamine (10 mg, 0.029 mmol) in pyridine (1 mL) was added 2,2,2-trifluoroethanesulfonyl chloride (6 mg, 0.03 mmol), the result mixture was stirred at r.t. for 20 h. The solvent was removed in vacuo, the residue was purified with column chromatography (petrol ether: EtOAc=1:2) to give the desired product (6.9 mg, 48%).

$^1$H NMR (CD$_3$OD): δ 9.55 (1H, s), 8.91 (1H, s), 8.05 (1H, dd, J=1.6, 4.8 Hz), 7.27-7.33 (1H, m), 6.98-7.03 (1H, m), 6.91-6.94 (1H, m), 4.13 (2H, q, J=9.6 Hz).

Example 20

N-(3-(3-(9H-purin-6-yl)pyridin-2-ylamino)-2,4-difluorophenyl)ethenesulfonamide

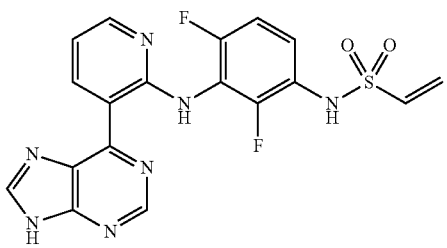 [SMILES: C=CS(=O)(=O)Nc1ccc(F)c(Nc2ncccc2-c2ncnc3[nH]cnc23)c1F]

Step 1: N-(3-(3-(9H-purin-6-yl)pyridin-2-ylamino)-2,4-difluorophenyl)ethenesulfonamide

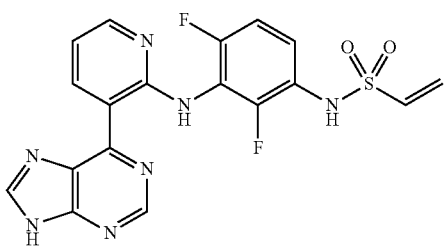 [SMILES: C=CS(=O)(=O)Nc1ccc(F)c(Nc2ncccc2-c2ncnc3[nH]cnc23)c1F]

N-(3-(3-(9H-purin-6-yl)pyridin-2-ylamino)-2,4-difluorophenyl)ethenesulfonamide was synthesized from N$^1$-(3-(9H-purin-6-yl)pyridin-2-yl)-2,6-difluorobenzene-1,3-diamine and 2-chloroethanesulfonyl chloride in a similar manner as described in Example 19, Step 1.

$^1$H NMR (CD$_3$OD): δ 9.64 (1H, br), 9.02 (1H, s), 8.53 (1H, s), 8.17 (1H, dd, J=1.6, 4.8 Hz), 7.33-7.39 (1H, m), 7.00-7.08 (2H, m), 6.73-6.79 (1H, m), 6.11-6.15 (1H, m), 5.97-6.00 (1H, m).

Example 21

N-(3-(3-(9H-purin-6-yl)pyridin-2-ylamino)-2,4-difluorophenyl)-2-phenylcyclopropane-1-sulfonamide

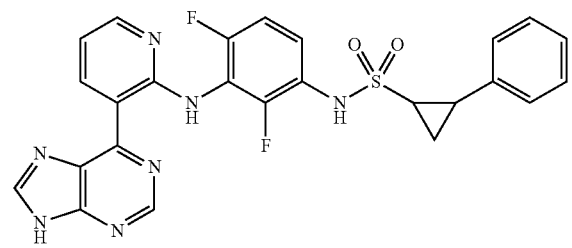 [SMILES: O=S(=O)(Nc1ccc(F)c(Nc2ncccc2-c2ncnc3[nH]cnc23)c1F)C1CC1c1ccccc1]

Step 1: N-(3-(3-(9H-purin-6-yl)pyridin-2-ylamino)-2,4-difluorophenyl)-2-phenylcyclopropane-1-sulfonamide

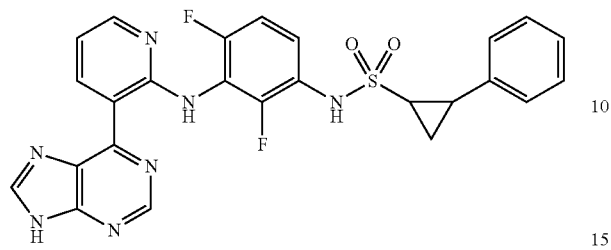

N-(3-(3-(9H-purin-6-yl)pyridin-2-ylamino)-2,4-difluorophenyl)-2-phenylcyclopropane-1-sulfon amide was synthesized from $N^1$-(3-(9H-purin-6-yl)pyridin-2-yl)-2,6-difluorobenzene-1,3-diamine and 2-phenylcyclopropane-1-sulfonyl chloride in a similar manner as described in Example 19, Step 1.

$^1$H NMR (CD$_3$OD): δ 9.55 (1H, br), 8.96 (1H, s), 8.50 (1H, s), 8.08 (1H, d, 0.1=4.8 Hz), 7.34-7.36 (1H, m), 6.93-7.09 (6H, m), 2.79-2.83 (1H, m), 2.41-2.43 (1H, m), 1.54-1.57 (1H, m), 1.40-1.43 (1H, m).

Example 22

N-(3-(3-(9H-purin-6-yl)pyridin-2-ylamino)-2,4-difluorophenyl)-2-(4-methoxyphenyl)cyclopropane-1-sulfonamide

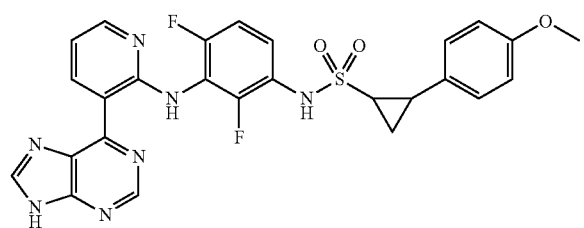 [SMILES: COc1ccc(C2CC2S(=O)(=O)Nc2ccc(F)c(Nc3ncccc3-c3ncnc4[nH]cnc34)c2F)cc1]

Step 1: N-(3-(3-(9H-purin-6-yl)pyridin-2-ylamino)-2,4-difluorophenyl)-2-(4-methoxyphenyl)cyclopropane-1-sulfonamide

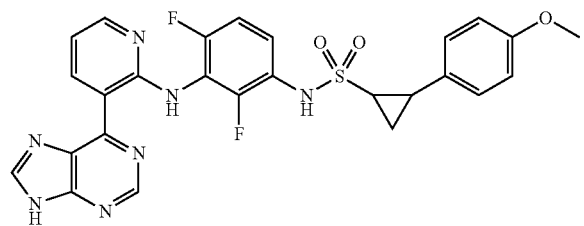 [SMILES: COc1ccc(C2CC2S(=O)(=O)Nc2ccc(F)c(Nc3ncccc3-c3ncnc4[nH]cnc34)c2F)cc1]

N-(3-(3-(9H-purin-6-yl)pyridin-2-ylamino)-2,4-difluorophenyl)-2-(4-methoxyphenyl)cyclopropane-1-sulfonamide was synthesized from $N^1$-(3-(9H-purin-6-yl)pyridin-2-yl)-2,6-difluorobenzene-1,3-diamine and 2-(4-methoxyphenyl)cyclopropane-1-sulfonyl chloride in a similar manner as described in Example 19, Step 1.

$^1$H NMR (CD$_3$OD): δ 9.50 (1H, br), 8.93 (1H, s), 8.50 (1H, s), 8.07 (1H, dd, J=4.8, 2.0 Hz), 7.34-7.36 (1H, m), 7.02-7.05 (1H, m), 6.95-6.98 (1H, m), 6.82-6.85 (2H, m), 6.61-6.64 (2H, m), 3.50 (3H, s), 2.71-2.74 (1H, m), 2.36-2.38 (1H, m), 1.50-1.53 (1H, m), 1.34-1.36 (1H, m).

Example 23

N-(3-(3-(9H-purin-6-yl)pyridin-2-ylamino)-2,4-difluorophenyl)-4-fluorobenzenesulfonamide

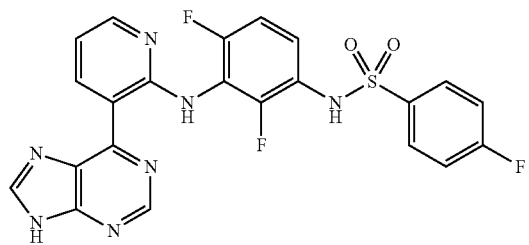 [SMILES: O=S(=O)(Nc1ccc(F)c(Nc2ncccc2-c2ncnc3[nH]cnc23)c1F)c1ccc(F)cc1]

Step 1: N-(3-(3-(9H-purin-6-yl)pyridin-2-ylamino)-2,4-difluorophenyl)-4-fluorobenzenesulfonamide

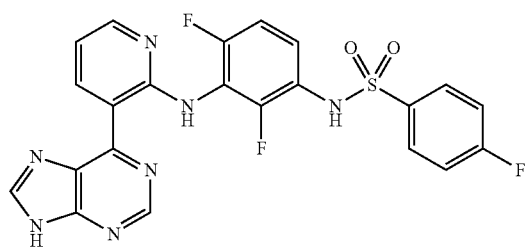

N-(3-(3-(9H-purin-6-yl)pyridin-2-ylamino)-2,4-difluorophenyl)-4-fluorobenzenesulfonamide was synthesized from $N^1$-(3-(9H-purin-6-yl)pyridin-2-yl)-2,6-difluorobenzene-1,3-diamine and 4-fluorobenzene-1-sulfonyl chloride in a similar manner as described in Example 19, Step 1.

$^1$H NMR (DMSO-d$_6$): δ 12.95 (1H, br), 11.45 (1H, br), 10.05 (1H, br), 9.65 (1H, br), 8.98 (1H, s), 8.72 (1H, s), 8.14 (1H, d, J=3.6 Hz), 7.77-7.79 (2H, m), 7.40-7.44 (2H, m), 7.11-7.15 (2H, m), 7.00-7.03 (1H, m).

Example 24

N-(3-(3-(9H-purin-6-yl)pyridin-2-ylamino)-2,4-difluorophenyl)thiophene-3-sulfonamide

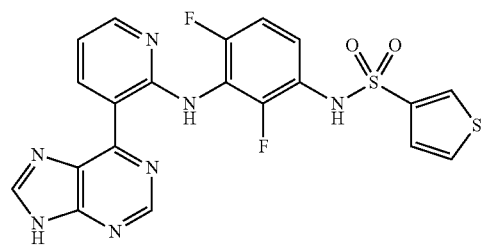 [SMILES: O=S(=O)(Nc1ccc(F)c(Nc2ncccc2-c2ncnc3[nH]cnc23)c1F)c1ccsc1]

Step 1: N-(3-(3-(9H-purin-6-yl)pyridin-2-ylamino)-2,4-difluorophenyl)thiophene-3-sulfonamide

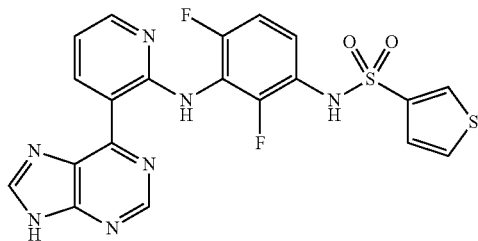 [SMILES: O=S(=O)(Nc1ccc(F)c(Nc2ncccc2-c2ncnc3[nH]cnc23)c1F)c1ccsc1]

N-(3-(3-(9H-purin-6-yl)pyridin-2-ylamino)-2,4-difluorophenyl)thiophene-3-sulfonamide was synthesized from $N^1$-(3-(9H-purin-6-yl)pyridin-2-yl)-2,6-difluorobenzene-1,3-diamine and thiophene-3-sulfonyl chloride in a similar manner as described in Example 19, Step 1.

$^1$H NMR (CD$_3$OD): δ 9.45 (1H, br), 8.86 (1H, s), 8.40 (1H, s), 8.02 (1H, dd, J=1.6, 4.8 Hz), 7.87 (1H, s), 7.87 (1H, dd, J=2.8, 4.8 Hz), 7.21 (2H, m), 6.88 (2H, m).

Example 25

N-(3-(3-(1H-pyrazolo[3,4-d]pyrimidin-4-yl)pyridin-2-ylamino)-2,4-difluorophenyl)propane-1-sulfonamide

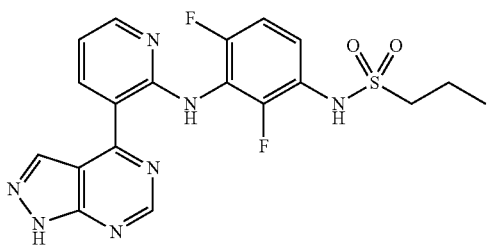 [SMILES: CCCS(=O)(=O)Nc1ccc(F)c(Nc2ncccc2-c2ncnc3[nH]ncc23)c1F]

Step 1: 4-chloro-1-(tetrahydro-2H-pyran-2-yl)-1H-pyrazolo[3,4-d]pyrimidine

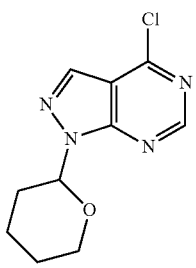 [SMILES: Clc1ncnc2c1cnn2C1CCCCO1]

To a solution of 4-chloro-1H-pyrazolo[3,4-d]pyrimidine (2.00 g, 12.9 mmol) in EtOAc (30 mL) was added 3,4-dihydro-2H-pyran (3.29 g, 39.1 mmol), followed by 4-methylbenzenesulfonic acid (1%) and the resulting reaction mixture was heated to refluxing for 3 hrs. The mixture was diluted with water, extracted with EtOAc, washed with brine, dried over Na$_2$SO$_4$, filtered and concentrated in vacuo. The residue was purified by column chromatography (petrol ether: EtOAc=6:1 to 4:1) to afford the desired product (0.85 g, 29%).

$^1$H NMR (DMSO-d$_6$): δ 8.62 (1H, s), 7.93 (1H, s), 5.53-5.56 (1H, m), 3.92-3.95 (1H, m), 3.64-3.67 (1H, m), 2.08-2.14 (1H, m), 1.89-1.99 (3H, m), 1.60-1.75 (2H, m).

Step 2: 4-(2-fluoropyridin-3-yl)-1-(tetrahydro-2H-pyran-2-yl)-1H-pyrazolo[3,4-d]pyrimidine

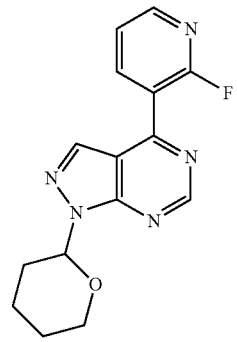 [SMILES: Fc1ncccc1-c1ncnc2c1cnn2C1CCCCO1]

4-(2-fluoropyridin-3-yl)-1-(tetrahydro-2H-pyran-2-yl)-1H-pyrazolo[3,4-d]pyrimidine was synthesized from 4-chloro-1-(tetrahydro-2H-pyran-2-yl)-1H-pyrazolo[3,4-d]pyrimidine (Example 10, Step 1) and 2-fluoro-3-(4,4,5,5-tetramethyl-1,3,2-dioxaborolan-2-yl)pyridine (Example 1, Step 8) in a similar manner as described in Example 1, Step 9.

$^1$H NMR (CDCl$_3$): δ 9.15 (1H, s), 8.51-8.56 (1H, m), 8.44-8.46 (1H, m), 8.33-8.34 (1H, m), 6.14-6.17 (1H, m), 4.10-4.17 (1H, m), 3.81-3.88 (1H, m), 2.63-2.73 (1H, m), 2.18-2.21 (1H, m), 2.00-2.02 (2H, m), 1.80-1.85 (3H, m).

Step 3: N-(2,4-difluoro-3-(3-(1-(tetrahydro-2H-pyran-2-yl)-1H-pyrazolo[3,4-d]pyrimidin-4-yl)pyridin-2-ylamino)phenyl)propane-1-sulfonamide

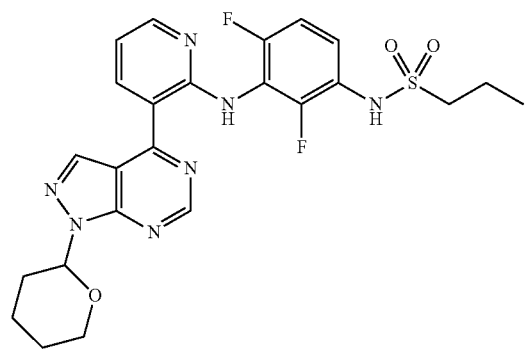 [SMILES: CCCS(=O)(=O)Nc1ccc(F)c(Nc2ncccc2-c2ncnc3c2cnn3C2CCCCO2)c1F]

N-(2,4-difluoro-3-(3-(1-(tetrahydro-2H-pyran-2-yl)-1H-pyrazolo[3,4-d]pyrimidin-4-yl)pyridin-2-ylamino)phenyl)propane-1-sulfonamide was synthesized from 4-(2-fluoropyridin-3-yl)-1-(tetrahydro-2H-pyran-2-yl)-1H-pyrazolo[3,4-d]pyrimidine (Example 10, Step 2) and N-(3-amino-2,4-difluorophenyl)propane-1-sulfonamide (Example 1, Step 7) in a similar manner as described in Example 1, Step 10.

$^1$H NMR (CDCl$_3$): δ 11.06 (1H, s), 9.09 (1H, s), 8.44 (1H, s), 8.34-8.37 (1H, m), 8.29-8.31 (1H, m), 7.39-7.45 (1H, m), 6.98-7.04 (2H, m), 6.35 (1H, s), 6.15-6.18 (1H, m), 4.14-4.18 (1H, m), 3.82-3.88 (1H, m), 3.07-3.11 (2H, m), 2.61-2.71 (1H, m), 2.17-2.22 (1H, m), 2.00-2.04 (1H, m), 1.80-1.94 (5H, m), 1.05 (3H, t, J=7.2 Hz).

Step 4: N-(3-(3-(1H-pyrazolo[3,4-d]pyrimidin-4-yl)pyridin-2-ylamino)-2,4-difluorophenyl)propane-1-sulfonamide

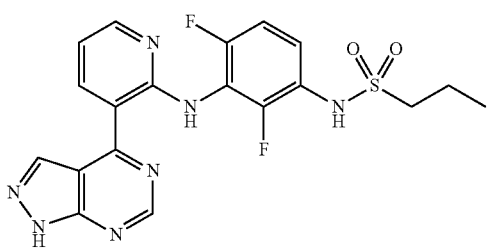 [SMILES: CCCS(=O)(=O)Nc1ccc(F)c(Nc2ncccc2-c2ncnc3[nH]ncc23)c1F]

N-(3-(3-(1H-pyrazolo[3,4-d]pyrimidin-4-yl)pyridin-2-ylamino)-2,4-difluorophenyl)propane-1-sulfonamide was synthesized from N-(2,4-difluoro-3-(3-(1-(tetrahydro-2H-pyran-2-yl)-1H-pyrazolo[3,4-d]pyrimidin-4-yl)pyridin-2-ylamino)phenyl)propane-1-sulfonamide (Example 10, Step 3) in a similar manner as described in Example 1, Step 11.

$^1$H NMR (CDCl$_3$): δ 11.35 (1H, s), 11.21 (1H, br), 9.14 (1H, s), 8.49 (1H, s), 8.42 (1H, dd, J=2.0 Hz, 8.0 Hz), 8.36 (1H, dd, J=1.6 Hz, 4.8 Hz), 7.43-7.48 (1H, m), 7.35 (1H, s), 7.01-7.04 (2H, m), 3.10-3.14 (2H, m), 1.88-1.94 (2H, m), 1.05 (3H, t, J=7.2 Hz).

Example 26

N-(3-(3-(7H-pyrrolo[2,3-d]pyrimidin-4-yl)pyridin-2-ylamino)-2,4-difluorophenyl)propane-1-sulfonamide

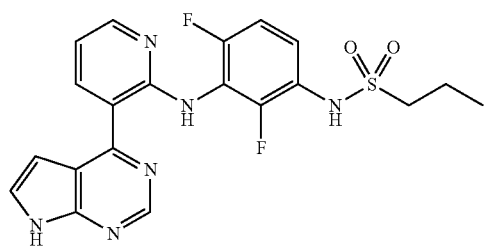 [SMILES: CCCS(=O)(=O)Nc1ccc(F)c(Nc2ncccc2-c2ncnc3[nH]ccc23)c1F]

Step 1: 4-(2-fluoropyridin-3-yl)-7H-pyrrolo[2,3-d]pyrimidine

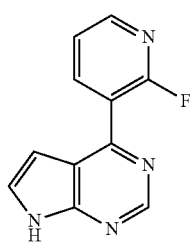 [SMILES: Fc1ncccc1-c1ncnc2[nH]ccc12]

To the mixture of 4-chloro-7H-pyrrolo[2,3-d]pyrimidine (300 mg, 1.95 mmol) and 2-fluoro-3-(4,4,5,5-tetramethyl-1,3,2-dioxaborolan-2-yl)pyridine (653 mg, 2.93 mmol) in ethylene glycol dimethyl ether (40 mL) was added water (10 mL), Na$_2$CO$_3$ (414 mg, 3.90 mmol) and Pd(PPh$_3$)$_4$ (5%) under N$_2$ atmosphere. The mixture was stirred at 80° C. for 20 h, filtered, the solvent was removed in vacuo. The residue was purified with column chromatography (petrol ether: EtOAc=1:2) to give the desired product (202 mg, 48%).

$^1$H NMR (DMSO-d$_6$): δ 12.36 (1H, s), 8.89 (1H, s), 8.37-8.44 (1H, m), 7.67-7.68 (1H, m), 7.58-7.61 (1H, m), 6.56-6.58 (1H, m).

Step 2: N-(3-(3-(7H-pyrrolo[2,3-d]pyrimidin-4-yl)pyridin-2-ylamino)-2,4-difluorophenyl)propane-1-sulfonamide

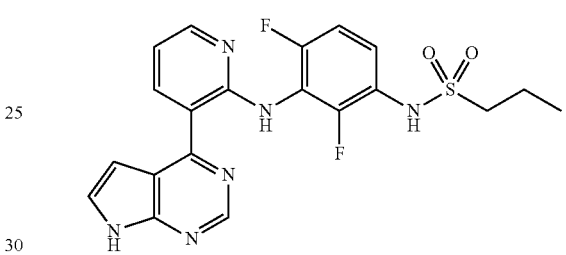

To the mixture of 4-(2-fluoropyridin-3-yl)-7H-pyrrolo[2,3-d]pyrimidine (5.8 mg, 0.027 mmol) and N-(3-amino-2,4-difluorophenyl)propane-1-sulfonamide (6.7 mg, 0.027 mmol) in tertiary butyl alcohol (3 mL) was added con. HCl (0.15 mL). The mixture was stirred at 150° C. under microwave for 2 h, then solvent was removed in vacuo, the residue was purified with column chromatography (petrol ether: EtOAc=1:1) to give the desired product (1.1 mg, 9%).

$^1$H NMR (CDCl$_3$): δ 11.42 (1H, s), 10.27 (1H, s), 9.18 (1H, s), 9.08 (1H, s), 8.37 (1H, dd, J=2.0, 7.6 Hz), 8.33 (1H, dd, J=2.0, 4.8 Hz), 7.49-7.54 (1H, m), 7.42-7.47 (1H, m), 6.97-7.04 (2H, m), 6.93 (1H, dd, J=2.0, 3.6 Hz), 3.15 (2H, t, J=8.0 Hz), 1.91-1.97 (2H, m), 1.03 (3H, t, J=7.6 Hz).

Example 27

N-(3-(2-(9H-purin-6-yl)phenylamino)-4-methylphenyl)propane-1-sulfonamide

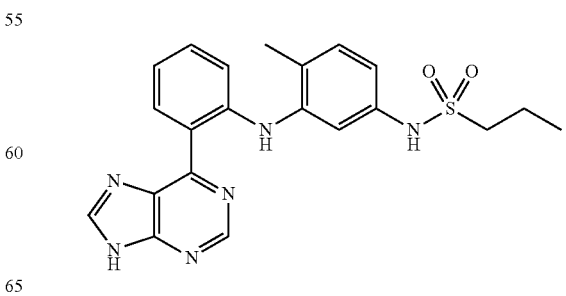

Step 1: 2-(4,4,5,5-tetramethyl-1,3,2-dioxaborolan-2-yl)aniline

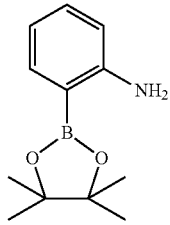 [SMILES: CC1(C)OB(c2ccccc2N)OC1(C)C]

To a solution of 2-bromoaniline (860 mg, 5 mmol) in dioxane (20 mL) was added 4,4,4',4',5,5,5',5'-octamethyl-2,2'-bi(1,3,2-dioxaborolane) (1.91 g, 7.5 mmol) and pumped $N_2$ for 30 min, followed by $PdCl_2(dppf)$ (5%) and potassium acetate (980 mg, 10 mmol). The resulting reaction mixture was heated to 80° C. for 15 hrs under $N_2$ atmosphere. After cooling, the mixture was diluted with water, extracted with EtOAc, washed with brine, dried over $Na_2SO_4$, filtered and concentrated in vacuo. The residue was purified by column chromatography to afford the desired product (517 mg, 47%).

$^1$H NMR (CDCl$_3$): δ 7.61 (1H, dd, J=1.6 Hz, 7.6 Hz), 7.23-7.19 (1H, m), 6.67 (1H, t, J=7.6 Hz), 6.59 (1H, d, J=8.0 Hz), 4.72 (2H, br), 1.34 (12H, s).

Step 2: 2-(9-(tetrahydro-2H-pyran-2-yl)-9H-purin-6-yl)aniline

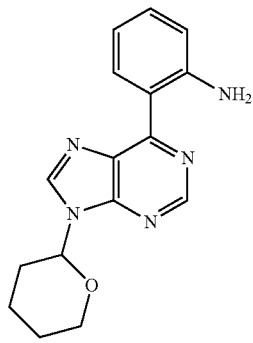 [SMILES: Nc1ccccc1-c1ncnc2c1ncn2C1CCCCO1]

To a solution of 6-chloro-9-(tetrahydro-2H-pyran-2-yl)-9H-purine (119 mg, 0.5 mmol) in toluene (20 mL) was added 2-(4,4,5,5-tetramethyl-1,3,2-dioxaborolan-2-yl)aniline (219 mg, 1.0 mmol) and pumped $N_2$ for 30 min, followed by $PdCl_2(dppf)$ (73 mg, 0.1 mmol) and cesium carbonate (489 mg, 1.5 mmol). The resulting reaction mixture was heated to 80° C. for 48 hrs under $N_2$ atmosphere. After cooling, the mixture was diluted with water, extracted with EtOAc, washed with brine, dried over $Na_2SO_4$, filtered and concentrated in vacuo. The residue was purified by column chromatography to afford the desired product (35 mg, 12%).

$^1$H NMR (CDCl$_3$): δ 8.97-8.94 (2H, m), 8.31 (1H, s), 7.27-7.23 (1H, m), 6.89-6.85 (1H, m), 6.78-6.76 (1H, dd, J=1.2 Hz, 8.0 Hz), 6.44 (1H, d, J=13.6 Hz), 5.86 (1H, dd, J=2.4 Hz, 10.4 Hz), 4.22-4.18 (1H, m), 3.85-3.78 (1H, m), 2.20-2.06 (3H, m), 1.84-1.62 (3H, m).

Step 3: N-(4-methyl-3-(2-(9-(tetrahydro-2H-pyran-2-yl)-9H-purin-6-yl)phenylamino)phenyl)propane-1-sulfonamide

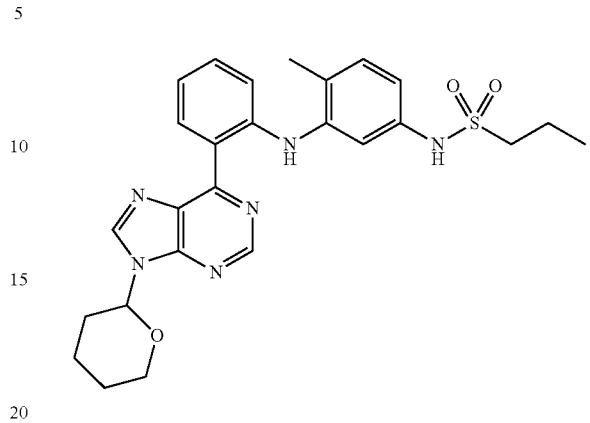

To a solution of 2-(9-(tetrahydro-2H-pyran-2-yl)-9H-purin-6-yl)aniline (35 mg, 0.12 mmol) in toluene (20 mL) was added N-(3-bromo-4-methylphenyl)propane-1-sulfonamide (38 mg, 0.13 mmol) and pumped $N_2$ for 30 min, followed by X-phos (6 mg, 10%), $Pd_2(dba)_3$ (6 mg, 5%) and cesium carbonate (78 mg, 0.23 mmol). The resulting reaction mixture was heated to 80° C. for 20 hrs under $N_2$ atmosphere. After cooling, the mixture was diluted with water, extracted with EtOAc, washed with brine, dried over $Na_2SO_4$, filtered and concentrated in vacuo. The residue was purified by column chromatography to afford the desired product (13 mg, 21%).

$^1$H NMR (CDCl$_3$): δ 10.89 (1H, s), 8.97-8.94 (2H, m), 8.36 (1H, s), 7.37-7.31 (2H, m), 7.20-7.16 (2H, m), 7.05-7.01 (1H, m), 6.82-6.79 (1H, m), 6.24 (1H, s), 5.88-5.85 (1H, m), 4.23-4.19 (1H, m), 3.85-3.79 (1H, m), 3.06-3.02 (2H, m), 2.23-2.07 (3H, m), 1.88-1.67 (5H, m), 1.01 (3H, t, J=7.2 Hz).

Step 4: N-(3-(2-(9H-purin-6-yl)phenylamino)-4-methylphenyl)propane-1-sulfonamide

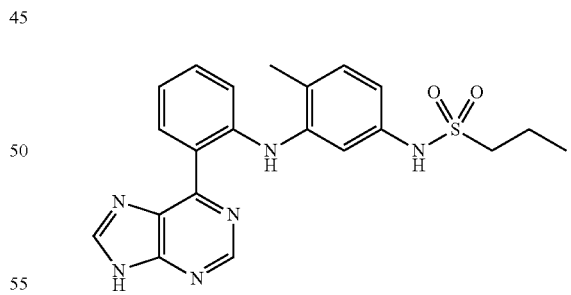

N-(3-(2-(9H-purin-6-yl)phenylamino)-4-methylphenyl)propane-1-sulfonamide was synthesized from N-(4-methyl-3-(2-(9-(tetrahydro-2H-pyran-2-yl)-9H-purin-6-yl)phenylamino)phenyl)propane-1-sulfonamide (Example 11, Step 3) in a similar manner as described in Example 1, Step 11.

$^1$H NMR (CDCl$_3$): δ 10.98-10.91 (2H, m), 9.05-9.00 (2H, m), 8.30 (1H, s), 7.38-7.34 (1H, m), 7.22-7.19 (1H, m), 7.05-7.00 (1H, m), 6.90-6.86 (2H, m), 5.30 (1H, s), 3.10-3.06 (2H, m), 2.35 (3H, s), 1.89-1.81 (2H, m), 1.02 (3H, t, J=7.2 Hz).

Example 28

N-(3-(2-(9H-purin-6-yl)phenylamino)-2,4-difluoro-phenyl)propane-1-sulfonamide

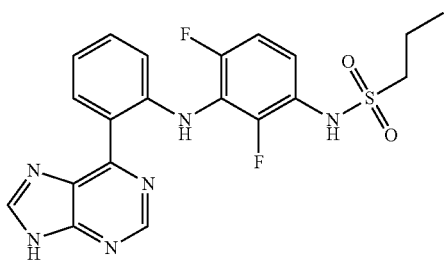 [SMILES: CCCS(=O)(=O)Nc1ccc(F)c(Nc2ccccc2-c2ncnc3[nH]cnc23)c1F]

Step 1: 1,3-difluoro-2-iodobenzene

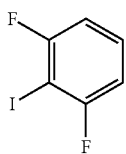

To a solution of 1,3-difluorobenzene (10.00 g, 87 mmol) in anhydrous THF (50 mL) was added n-BuLi (42 mL, 105 mmol) at −78° C. under $N_2$ atmosphere over 10 min, then the mixture was warmed to room temperature for 5 min and iodine (26.7 g, 105 mmol) in THF (200 mL) was added slowly and continued to stirred at room temperature for 4 hrs. The mixture was quenched with water, extracted with $CH_2Cl_2$, washed with brine, dried over $Na_2SO_4$, filtered and concentrated in vacuo to afford the desired product (12.5 g, 74%).

$^1$H NMR (CDCl$_3$): δ 7.24-7.30 (1H, m), 6.89 (2H, dd, J=6.6 Hz, 8.4 Hz).

Step 2: 1,3-difluoro-2-iodo-4-nitrobenzene

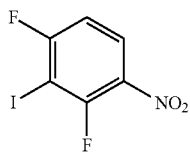

To a solution of 1,3-difluoro-2-iodobenzene (3.00 g, 12.5 mmol) in con.$H_2SO_4$ (10 mL) was added nitric acid (98%) (1.97 g, 31.3 mmol) at 0° C. and the resulting reaction mixture was stirred at room temperature for 4 min. The mixture was dropped into ice-water (80 mL), neutralized to pH=9 with aqueous NaOH (5%) and extracted with EtOAc. The extract was washed with brine, dried over $Na_2SO_4$, filtered and concentrated in vacuo to afford the desired product (3.1 g, 89%).

$^1$H NMR (CDCl$_3$): δ 8.12-8.17 (1H, m), 7.04-7.08 (1H, m).

Step 3: 2,4-difluoro-3-iodoaniline

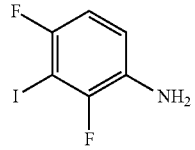

To a solution of 1,3-difluoro-2-iodo-4-nitrobenzene (1.14 g, 4 mmol) in con.HCl (4 mL) was added Satannous chloride dehydrate (2.71 g, 12 mmol) and the resulting reaction mixture was heated to 50° C. for 1 hrs. The mixture was diluted with water, neutralized to pH=9 with aqueous NaOH (5%) and extracted with $CH_2Cl_2$. The extract was washed with brine, dried over $Na_2SO_4$, filtered and concentrated in vacuo to afford the desired product (0.93 g, 91%).

1H NMR (CDCl$_3$): δ 6.70-6.93 (2H, m), 6.65 (2H, br).

Step 4: N-(2,4-difluoro-3-iodophenyl)propane-1-sulfonamide

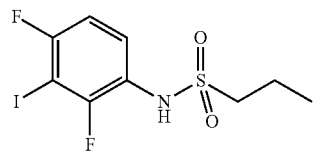 [SMILES: CCCS(=O)(=O)Nc1ccc(F)c(I)c1F]

To a solution of 2,4-difluoro-3-iodoaniline (255 mg, 1 mmol) in 1,2-dichloroethane (3 mL) was added pyridine (1 mL), followed by propane-1-sulfonyl (157 mg, 1.1 mmol) and the resulting reaction mixture was heated to refluxing for 2 hrs. The solvent was removed in vacuo. The residue was dissolved in EtOAc, washed with aqueous NaHCO$_3$, brine, dried over $Na_2SO_4$, filtered and concentrated in vacuo to afford the desired product (298 mg, 83%).

1H NMR (CDCl$_3$): δ 7.56-7.58 (1H, m), 6.90-6.95 (1H, m), 6.44 (1H, br), 3.03-3.07 (2H, m), 1.84-1.90 (2H, m), 1.03-1.07 (3H, m).

Step 5: N-(2,4-difluoro-3-(2-(9-(tetrahydro-2H-pyran-2-yl)-9H-purin-6-yl)phenylamino)phenyl)propane-1-sulfonamide

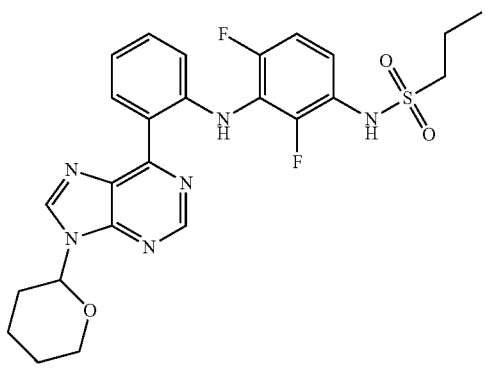 [SMILES: CCCS(=O)(=O)Nc1ccc(F)c(Nc2ccccc2-c2ncnc3c2ncn3C2CCCCO2)c1F]

To a solution of 2-(9-(tetrahydro-2H-pyran-2-yl)-9H-purin-6-yl)aniline (50 mg, 0.17 mmol) in THF (6 mL), was added N-(2,4-difluoro-3-iodophenyl)propane-1-sulfonamide (61 mg, 0.17 mmol) and pumped N₂ for 30 min, followed by Cu (20 mg) and K₂CO₃ (70 mg, 0.51 mmol). The resulting reaction mixture was heated to refluxing for 20 hrs under N₂ atmosphere. After cooling, the mixture was diluted with water, extracted with EtOAc, washed with brine, dried over Na₂SO₄, filtered and concentrated in vacuo. The residue was purified by column chromatography (Petrol ether: EtOAc=6:1 to 4:1) to afford the desired product (7 mg, 8%).

¹H NMR (CDCl₃): δ 11.01 (1H, s), 9.02 (1H, d, J=7.6 Hz), 8.99 (1H, s), 8.38 (1H, s), 7.32-7.36 (2H, m), 7.02-7.08 (2H, m), 6.74-6.76 (1H, d, J=4.4 Hz), 6.40 (1H, s), 5.87-5.89 (1H, m), 4.20-4.23 (1H, m), 3.80-3.84 (1H, m), 3.03-3.08 (2H, m), 2.05-2.18 (3H, m), 1.65-1.86 (5H, m), 1.08-1.10 (3H, m).

Step 6: N-(3-(2-(9H-purin-6-yl)phenylamino)-2,4-difluorophenyl)propane-1-sulfonamide

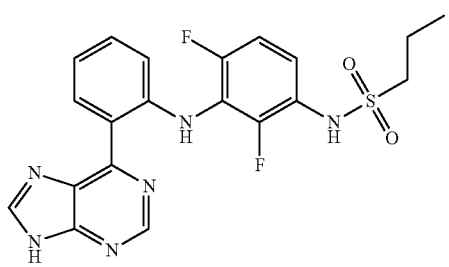 [SMILES: CCCS(=O)(=O)Nc1ccc(F)c(Nc2ccccc2-c2ncnc3[nH]cnc23)c1F]

N-(3-(2-(9H-purin-6-yl)phenylamino)-2,4-difluorophenyl)propane-1-sulfonamide was synthesized from. N-(2,4-difluoro-3-(2-(9-(tetrahydro-2H-pyran-2-yl)-9H-purin-6-yl)phenylamino)phenyl)propane-1-sulfonamide (Example 12, Step 5) in a similar manner as described in Example 1, Step 11.

¹H NMR (CD₃OD): δ 8.95 (1H, s), 8.75-8.77 (1H, m), 8.45 (1H, s), 7.31-7.33 (1H, m), 7.24-7.26 (1H, m), 7.03-7.05 (2H, m), 6.76-6.77 (1H, m), 3.04-3.06 (2H, m), 1.80-1.86 (2H, m), 1.02-1.04 (3H, m).

Example 29

N-(2-(2-(9H-purin-6-yl)phenylamino)pyridin-4-yl)propane-1-sulfonamide

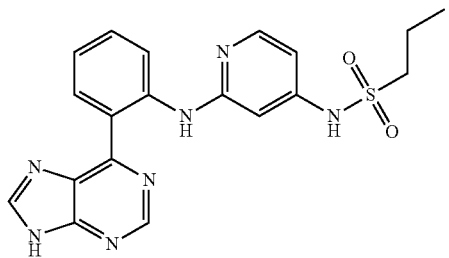 [SMILES: CCCS(=O)(=O)Nc1ccnc(Nc2ccccc2-c2ncnc3[nH]cnc23)c1]

Step 1: 2-(9-(tetrahydro-2H-pyran-2-yl)-9H-purin-6-yl)aniline

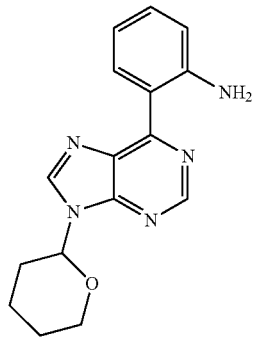 [SMILES: Nc1ccccc1-c1ncnc2c1ncn2C1CCCCO1]

To a solution of 6-chloro-9-(tetrahydro-2H-pyran-2-yl)-9H-purine (220 mg, 0.92 mmol) in MeCN (5 mL) and H₂O (2 mL) was added 2-(4,4,5,5-tetramethyl-1,3,2-dioxaborolan-2-yl)aniline (250 mg, 1.20 mmol), followed by K₂CO₃ (380 mg, 2.76 mmol) and Pd(PPh₃)₄ (106 mg, 0.09 mmol). After pumped N₂ for 2 min, the resulting reaction mixture was heated to 170° C. for 15 min with CEM microwave synthesis system. After cooling, the mixture was diluted with water, extracted with EtOAc, washed with brine, dried over Na₂SO₄, filtered and concentrated in vacuo. The residue was purified by column chromatography (Petrol ether: EtOAc=4:1 to 3:1) to afford the desired product (120 mg, 44%).

¹H NMR (CDCl₃): δ 8.97 (1H, d, J=4.4 Hz), 8.94 (1H, s), 8.31 (1H, s), 7.24-7.26 (1H, m), 6.85-6.90 (1H, m), 6.77 (1H, d, J=4.4 Hz), 6.37 (2H, s), 5.84-5.88 (1H, m), 4.18-4.23 (1H, m), 3.75-3.85 (1H, m), 2.05-2.18 (3H, m); 1.65-1.86 (3H, m).

Step 2: N-(2-chloropyridin-4-yl)propane-1-sulfonamide

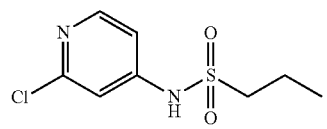

To a solution of 2-chloropyridin-4-amine (1.00 g, 7.80 mmol) in 1,2-dichloroethane (30 mL) was added pyridine (3 mL), followed by propane-L-sulfonyl (1.28 g, 8.9 mmol) and the resulting reaction mixture was heated to refluxing for 20 hrs. The solvent was removed in vacuo. The residue was dissolved in EtOAc, washed with aqueous NaHCO₃ (5%), brine, dried over Na₂SO₄, filtered and concentrated in vacuo. The residue was purified by column chromatography (Petrol ether:EtOAc=5:1 to 3:1) to afford the desired product (400 mg, 22%).

¹H NMR (CDCl₃): δ 8.27 (1H, d, J=5.6 Hz), 7.40 (1H, br), 7.15 (1H, d, J=2.0 Hz), 7.00-7.03 (1H, dd, J=5.6 Hz, J=2.0 Hz), 3.14-3.18 (2H, m), 1.82-1.92 (2H, m), 1.08-1.10 (3H, m).

Step 3: N-(2-(2-(9-(tetrahydro-2H-pyran-2-yl)-9H-purin-6-yl)phenylamino)pyridin-4-yl)propane-1-sulfonamide

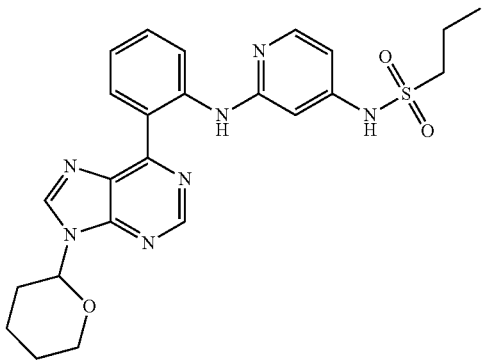 [SMILES: CCCS(=O)(=O)Nc1ccnc(Nc2ccccc2-c2ncnc3c2ncn3C2CCCCO2)c1]

To a solution of 2-(9-(tetrahydro-2H-pyran-2-yl)-9H-purin-6-yl)aniline (20 mg, 0.067 mmol) in toluene (2 mL) was added N-(2-chloropyridin-4-yl)propane-1-sulfonamide (16 mg, 0.067 mmol), followed by Pd$_2$(dba)$_3$ (3 mg, 0.006 mmol), Xant-Phos (4 mg, 0.006 mmol and t-BuONa (10 mg, 0.17 mmol). After pumped N$_2$ for 5 min, the resulting reaction mixture was heated to 170° C. for 2 hrs with CEM microwave synthesis system. After cooling, the mixture was diluted with water, extracted with EtOAc, washed with brine, dried over Na$_2$SO$_4$, filtered and concentrated in vacuo. The residue was purified by column chromatography (Petrol ether:EtOAc=5:1 to 3:1) to afford the desired product (5 mg, 15%).

$^1$H NMR (CDCl$_3$): δ 11.44 (1H, s), 9.04 (1H, s), 8.76-8.78 (1H, m), 8.38 (1H, s), 8.09-8.15 (2H, m), 7.18-7.20 (1H, m), 6.69 (1H, d, J=2.0 Hz), 6.53-6.56 (1H, dd, J=2.0 Hz, 5.6 Hz), 5.84-5.88 (1H, m), 4.18-4.21 (1H, m), 3.80-3.84 (1H, m), 3.14-3.18 (2H, m), 2.05-2.18 (3H, m), 1.65-1.92 (5H, m), 1.08-1.10 (3H, m).

Step 4: N-(2-(2-(9H-purin-6-yl)phenylamino)pyridin-4-yl)propane-1-sulfonamide

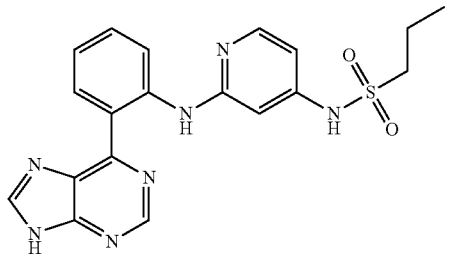 [SMILES: CCCS(=O)(=O)Nc1ccnc(Nc2ccccc2-c2ncnc3[nH]cnc23)c1]

N-(2-(2-(9H-purin-6-yl)phenylamino)pyridin-4-yl)propane-1-sulfonamide was synthesized from N-(2-(2-(9-(tetrahydro-2H-pyran-2-yl)-9H-purin-6-yl)phenylamino)pyridin-4-yl)propane-1-sulfonamide (Example 13, Step 3) in a similar manner as described in Example 1, Step 11.

$^1$H NMR (CDCl$_3$): δ 11.82 (1H, s), 9.14 (1H, s), 8.95 (1H, s), 8.43 (1H, s), 8.33 (1H, s), 8.20 (1H, d, J=2.8 Hz), 7.49-7.53 (1H, m), 7.16-7.20 (2H, m), 6.85-6.88 (1H, m), 6.59 (1H, d, J=2.0 Hz), 3.21-3.25 (2H, m), 1.82-1.92 (2H, m), 1.08-1.10 (3H, m).

Testing of Compounds of the Invention In Vitro

In vitro B-RAF Kinase Assay. To determine in vitro activities of recombinant B-RAF enzyme, a Homogeneous Time-Resolved Fluorescence (HTRF) assay was performed. Inactive (unphosphorylated) 6HIS-Mek1 was utilized as a protein substrate, the phosphorylated product was detected with Eu3+ cryptate-labeled anti-phosphotyrosine PT66 antibody (Anti-Phospho Mek1/2(Ser217/221)-Cryptate, Cisbio International). Meanwhile, an Anti-6HIS-d2 antibody (Anti-6HIS-d2, Cisbio international) was added to detection system. When the two antibodies were close enough, energy, transfer was happened between Eu and d2, then activities of enzyme was determine by measuring fluorescence intensity (320 nm excitation, 665 nm emission).

IC$_{50}$ determination. To evaluate in vitro potency of compounds against B-RAF enzyme, the IC$_{50}$ values of compounds of this invention were determined. Compounds were 3-fold serially diluted with 100% DMSO from 1 mM, then 4 ml of compounds were transferred to 96 ml of reaction buffer (50 mM HEPES pH7.4, 10 mM MgCl$_2$, 1 mM EGTA, 0.01% Tween-20, 0.005% BAS, 2 mM DTT). After mixed, 2.5 ml of 4×compound and 5 ml of 2×B-RAF of was added to a 384-well plate (OptiPlate-384, PerkinElmer), centrifuged and incubated for 5 min. Then 2.5 ml of 4×ATP (2 mM) was added to the reaction system and initiated the reaction. The assay plate was incubated in an incubator for 60 min at 23° C., then the reaction was terminated by adding 5 ml of detection solution containing Eu3+ cryptate-labeled anti-phosphotyrosine PT66 antibody, and 5 ml of Anti-6HIS-d2 antibody. The plate was incubated for 1 h at 23° C. and the fluorescent signal was read with an EnVision multilable plate reader (PerkinElmer). IC$_{50}$ values of compounds were generated using GraFit software (Version 6.0).

| Biologic Activity | |
|---|---|
| Compounds of the invention | IC$_{50}$ (nM) |
| Compound of Example 1 | <100 |
| Compound of Example 3 | <500 |
| Compound of Example 4 | <100 |
| Compound of Example 5 | <100 |
| Compound of Example 6 | <100 |
| Compound of Example 7 | <100 |
| Compound of Example 8 | <100 |
| Compound of Example 9 | <100 |
| Compound of Example 10 | <100 |
| Compound of Example 11 | <500 |
| Compound of Example 12 | <1000 |
| Compound of Example 13 | <500 |
| Compound of Example 14 | <500 |
| Compound of Example 15 | <100 |
| Compound of Example 17 | <500 |
| Compound of Example 18 | <100 |
| Compound of Example 19 | <100 |
| Compound of Example 20 | <500 |
| Compound of Example 21 | <500 |
| Compound of Example 22 | <1000 |
| Compound of Example 23 | <1000 |
| Compound of Example 24 | <100 |
| Compound of Example 25 | <500 |
| Compound of Example 26 | <500 |
| Compound of Example 27 | <100 |
| Compound of Example 28 | <1000 |

We claim:
1. A compound represented by Formula (I):

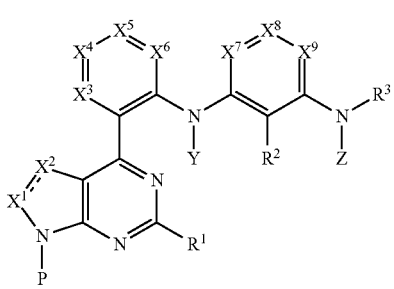

wherein:
R¹ is selected from hydrogen, alkyl, alkenyl, alkynyl, cycloalkyl, heterocycloalkyl, aryl, heteroaryl, alkoxy, alkylthio, or halogen, wherein the said groups are optionally substituted with one or more substituents selected from the group consisting of halogen, —OH, —NH₂, lower alkyl, lower alkoxy, lower alkylthio, lower mono-alkylamino, lower di-alkylamino, and lower cycloalkylamino;

R² is selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein the above said groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino;

R³ is selected from the group consisting of —S(=O)₂Rᵃ and —S(=O)Rᵃ;

Rᵃ is selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein those groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, cycloalkylamino, and aryl optionally substituted with one or more halogen, hydroxyl, amino, lower alkyl, lower alkoxy, and lower alkylthio; or Rᵃ is selected from the group consisting of —(CRᶜRᵈ)ₙRᵉ and —(CRᶜRᵈ)ₙORᵉ;

Rᶜ and Rᵈ are independently selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein those groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino; or Rᶜ and Rᵈ combine to form a cycloalkyl or heterocycloalkyl, wherein the cycloalkyl or heterocycloalkyl is optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, cycloalkylamino, aryl optionally substituted with one or more halogen, hydroxyl, amino, lower alkyl, lower alkoxy, and lower alkylthio;

Rᵉ is selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein those groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino;

n is 0, 1, 2, 3, 4, 5 or 6;

X¹ is CR⁴ and X² is N to form imidazolyl;

R⁴ is selected from the group consisting of hydrogen, halogen, lower alkyl, alkenyl, alkynyl, cycloalkyl, heterocycloalkyl, aryl, heteroaryl, alkoxy, alkylthio, alkoxycarbonyl, cyano, —OH, —NHC(=O)-alkyl, —S(=O)₂-alkyl, —S(=O)₂-cycloalkyl, —S(=O)₂NH₂, —S(=O)₂NH-alkyl, —N(alkyl)-S(=O)₂-alkyl, —C(=O)-alkyl, —NO₂, —NHS(=O)₂-alkyl, —NHS(=O)₂-cycloalkyl, —NHS(=O)₂-aryl, —NHS(=O)₂-heteroaryl, —S(=O)₂N-(alkyl)₂, —C(=O)NH-alkyl, —C(=O)N-(alkyl)₂, —S(=O)-alkyl, —S(=O)-lower cycloalkyl, —S(=O)-heteroalkyl, —C(=O)NH₂, triazolyl, and tetrazolyl, wherein the said groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino;

X³, X⁴, X⁵ and X⁶ are independently selected from the group consisting of CR⁶ and N to form phenyl or pyridinyl;

each R⁶ is independently selected from the group consisting of hydrogen, halogen, alkyl, alkenyl, alkynyl, cycloalkyl, heterocycloalkyl, aryl, heteroaryl, alkoxy, alkoxycarbonyl, cyano, —OH, —NHC(=O)-alkyl, —S(=O)₂-alkyl, —S(=O)₂-cycloalkyl, —S(=O)₂NH₂, —S(=O)₂NH-alkyl, —N(alkyl)-S(=O)₂-alkyl, —C(=O)-alkyl, —NO₂, —NHS(=O)₂-alkyl, —NHS(=O)₂-cycloalkyl, —NHS(=O)₂-aryl, —NHS(=O)₂-heteroaryl, —S(=O)₂N-(alkyl)₂, —C(=O)NH-alkyl, —C(=O)N-(alkyl)₂, —S(=O)-alkyl, —S(=O)-heteroalkyl, —C(=O)NH₂, triazolyl, and tetrazolyl, wherein the said groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino;

X⁷, X⁸ and X⁹ are independently selected from the group consisting of CR⁸ and N to form phenyl or pyridinyl;

each R⁸ is independently selected from the group consisting of hydrogen, halogen, alkyl, alkenyl, alkynyl, cycloalkyl, heterocycloalkyl, aryl, heteroaryl, alkoxy, alkylthio, alkoxycarbonyl, cyano, —NHC(=O)-alkyl, —S(=O)₂-alkyl, —S(=O)₂-cycloalkyl, —S(=O)₂NH₂, —S(=O)₂NH-alkyl, —N(alkyl)-S(=O)₂-alkyl, —C(=O)-alkyl, —NO₂, —NHS(=O)₂-alkyl, —NHS(=O)₂-cycloalkyl, —NHS(=O)₂-aryl, —NHS(=O)₂-heteroaryl, —S(=O)₂N-(alkyl)₂, —C(=O)NH-alkyl, —C(=O)N-(alkyl)₂, —S(=O)-alkyl, —S(=O)-heteroalkyl, —C(=O)NH₂, triazolyl, and tetrazolyl, wherein the said groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino; and P, Y and Z are independently selected from the group consisting of hydrogen, alkyl, alkenyl, alkynyl, cycloalkyl, heterocycloalkyl, aryl and heteroaryl, wherein those groups are optionally substituted with one or more substituents selected from the group consisting of halogen, hydroxyl, amino, and cyano;

with a provision that when X³, X⁴, X⁵ and X⁶ are independently selected from the group consisting of CR⁶ and N to form pyridinyl, X⁷, X⁸ and X⁹ are independently CR⁸ to form phenyl; and when X³, X⁴, X⁵ and X⁶ are independently selected from the group consisting of CR⁶ to form phenyl, X⁷, X⁸ and X⁹ are independently CR⁸ and N to form phenyl or pyridinyl;

or a pharmaceutically acceptable salt, solvate, polymorph, or tautomer thereof.

2. A compound according to claim 1, wherein
R³ is —S(=O)₂R¹⁰;
R¹⁰ is selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein those groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, cycloalkylamino and aryl optionally substituted with one or more halogen, hydroxyl, amino, lower alkyl, lower alkoxy, and lower alkylthio; or
R¹⁰ is selected from the group consisting of —(CR¹¹R¹²)ₘR¹³ and —(CR¹¹R¹²)ₘOR¹³;
R¹¹ and R¹² are independently selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein those groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino; or
R¹¹ and R¹² combine to form a cycloalkyl or heterocycloalkyl, wherein the cycloalkyl or heterocycloalkyl is optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, cycloalkylamino, and aryl optionally substituted with one or more halogen, hydroxyl, amino, lower alkyl, lower alkoxy, and lower alkylthio;

R¹³ is selected from the group consisting of hydrogen, halogen, alkyl, alkenyl, alkynyl, cycloalkyl, heterocycloalkyl, aryl, heteroaryl, alkoxy, alkoxycarbonyl, alkylthio, cyano, —OH, and —NH₂, wherein those groups are optionally substituted with one or more substituents selected from the group consisting of halogen, —OH, —NH₂, lower alkyl, halogen substituted lower alkyl, cycloalkyl, halogen substituted cycloalkyl, lower alkoxy, halogen substituted lower alkoxy, lower alkylthio, halogen substituted lower alkylthio, mono-alkylamino, di-alkylamino, and cycloalkylamino; and m is 0, 1, 2, 3, 4, 5 or 6.

3. A compound of claim 1 represented by Formula (A):

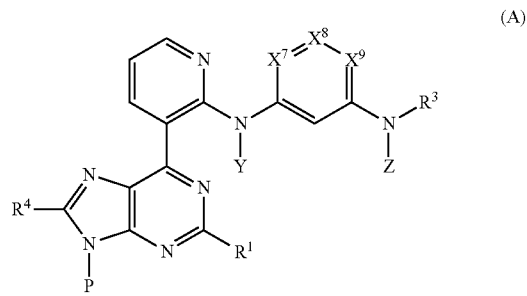

(A)

or a pharmaceutically acceptable salt, solvate, polymorph, or tautomer thereof.

4. A compound of claim 1, wherein
R¹ is selected from hydrogen, lower alkyl, lower alkenyl, lower alkynyl, lower cycloalkyl, lower heterocycloalkyl, lower alkoxy, lower alkylthio, or halogen, wherein the said groups are optionally substituted with one or more substituents selected from the group consisting of halogen, —OH and —NH₂;
R³ is —S(=O)₂R¹⁰, wherein
R¹⁰ is selected from the group consisting of hydrogen, lower alkyl, lower alkenyl, lower alkynyl, lower cycloalkyl, lower heterocycloalkyl, monocyclic aryl, monocyclic heteroaryl, lower alkoxy and lower alkylthio, wherein those groups are optionally substituted with one or more substituents selected from the group consisting of halogen, —OH, —NH₂, lower alkyl, halogen substituted lower alkyl, lower cycloalkyl, halogen substituted lower cycloalkyl, lower alkoxy, halogen substituted lower alkoxy, lower alkylthio, halogen substituted lower alkylthio, mono-lower alkylamino, di-lower alkylamino, lower cycloalkylamino, and aryl optionally substituted with one or more halogen, hydroxyl, amino, lower alkyl, lower alkoxy and lower alkylthio;
R⁴ is selected from the group consisting of hydrogen, halogen, lower alkyl, lower alkenyl, lower alkynyl, lower cycloalkyl, lower heterocycloalkyl, monocyclic aryl, monocyclic heteroaryl, lower alkoxy, lower alkylthio, lower alkoxycarbonyl, cyano, —OH, —NHC(=O)-lower alkyl, —S(=O)₂-lower alkyl, —S(=O)₂-lower cycloalkyl, —S(=O)₂NH₂, —S(=O)₂NH-lower alkyl, —N(lower alkyl)-S(=O)₂-lower alkyl, —C(=O)-lower alkyl, —NO₂, —NHS(=O)₂-lower alkyl, —NHS(=O)₂-lower cycloalkyl, —NHS(=O)₂-monocyclic aryl, —NHS(=O)₂-monocyclic heteroaryl, —S(=O)₂N-(lower alkyl)₂, —C(=O)NH-lower alkyl, —C(=O)N-(lower alkyl)₂, —S(=O)-lower alkyl, —S(=O)-lower cycloalkyl, —C(=O)NH₂, triazolyl, and tetrazolyl, wherein the said groups are optionally substituted with one or more substituents selected from the group consisting of halogen, —OH, —NH₂, lower alkyl, lower alkoxy, lower alkylthio, lower cycloalkyl, halogen substituted lower alkyl, halogen substituted lower alkoxy, halogen substituted lower alkylthio, halogen substituted lower cycloalkyl, mono-lower alkylamino, di-lower alkylamino, and lower cycloalkylamino;

X⁷, X⁸ and X⁹ are independently selected from CR⁸ to form phenyl; wherein each R⁸ is independently selected from the group consisting of hydrogen, halogen, lower alkyl, lower alkenyl, lower alkynyl, lower cycloalkyl, lower heterocycloalkyl, monocyclic aryl, monocyclic heteroaryl, lower alkoxy, lower alkylthio, lower alkoxycarbonyl, cyano, —OH, —NHC(=O)-lower alkyl, —S(=O)₂-lower alkyl, —S(=O)₂-lower cycloalkyl, —S(=O)₂NH₂, —S(=O)₂NH-lower alkyl, —S(=O)₂N-(lower alkyl)₂, —N(lower alkyl)-S(=O)₂-alkyl, —C(=O)-lower alkyl, —NO₂, —NHS(=O)₂-lower alkyl, —NHS(=O)₂-lower cycloalkyl, —NHS(=O)₂-monocyclic aryl, —NHS(=O)₂-monocyclic heteroaryl, —C(=O)NH-lower alkyl, —C(=O)N-(lower alkyl)₂, —S(=O)-lower alkyl, —S(=O)-lower heteroalkyl, —C(=O)NH₂, triazolyl, and tetrazolyl, wherein the said groups are optionally substituted with one or more substituents selected from the group consisting of halogen, —OH, —NH₂, lower alkyl, halogen substituted lower alkyl, lower cycloalkyl, halogen substituted lower cycloalkyl, lower alkoxy, halogen substituted lower alkoxy, lower alkylthio, halogen substituted lower alkylthio, mono-lower alkylamino, di-lower alkylamino, and lower cycloalkylamino; and P, Y and Z are independently selected from the group consisting of hydrogen, lower alkyl, lower alkenyl, lower alkynyl, lower cycloalkyl, lower heterocycloalkyl, monocyclic aryl and monocyclic heteroaryl, wherein said groups are optionally substituted with one or more substituents selected from the group consisting of halogen, hydroxyl, amino, and cyano.

5. A compound of claim 1, wherein P, Y and Z are hydrogen.

6. A compound of claim 1, wherein

R¹ is selected from hydrogen, lower alkyl, lower cycloalkyl, lower heterocycloalkyl, lower alkoxy or halogen, wherein the said groups are optionally substituted with one or more substituents selected from the group consisting of halogen, —OH and —NH₂; and/or R³ is —S(=O)₂R¹⁰, wherein R¹⁰ is selected from the group consisting of hydrogen, lower alkyl, lower alkenyl, lower alkynyl, lower cycloalkyl, lower heterocycloalkyl, lower alkoxy, lower alkylthio, monocyclic or bicyclic aryl, and monocyclic or bicyclic heteroaryl, wherein those above groups are optionally substituted with one or more substituents selected from the group consisting of halogen, —OH, —NH₂, lower alkyl and aryl optionally substituted with one or more halogen, hydroxyl, amino, lower alkyl, lower alkoxy and lower alkylthio.

7. A compound of claim 1, wherein

R⁴ is selected from the group consisting of hydrogen, halogen, lower alkyl, lower alkenyl, lower alkynyl, lower cycloalkyl, lower heterocycloalkyl, lower alkoxy, cyano and —OH, wherein the said groups are optionally substituted with one or more substituents selected from the group consisting of halogen, —OH and —NH₂.

8. A compound of claim 1, wherein

X⁷, X⁸ and X⁹ are independently selected from CR⁸ to form phenyl; wherein each R⁸ is independently selected from the group consisting of hydrogen, halogen, lower alkyl, lower cycloalkyl, lower heterocycloalkyl and lower alkoxy; wherein the said groups are optionally substituted with one or more substituents selected from the group consisting of halogen, —OH and —NH₂.

9. A compound according to claim 1, represented by any of the following formula:

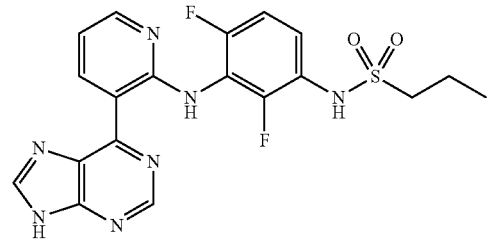

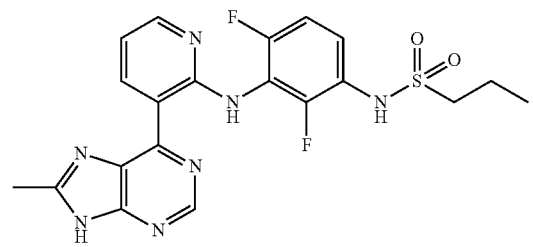

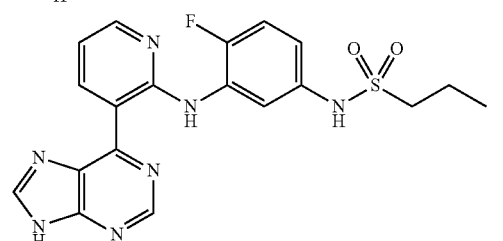

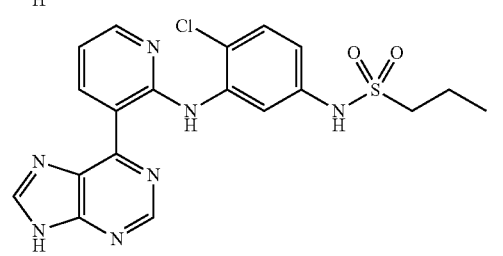

83
-continued
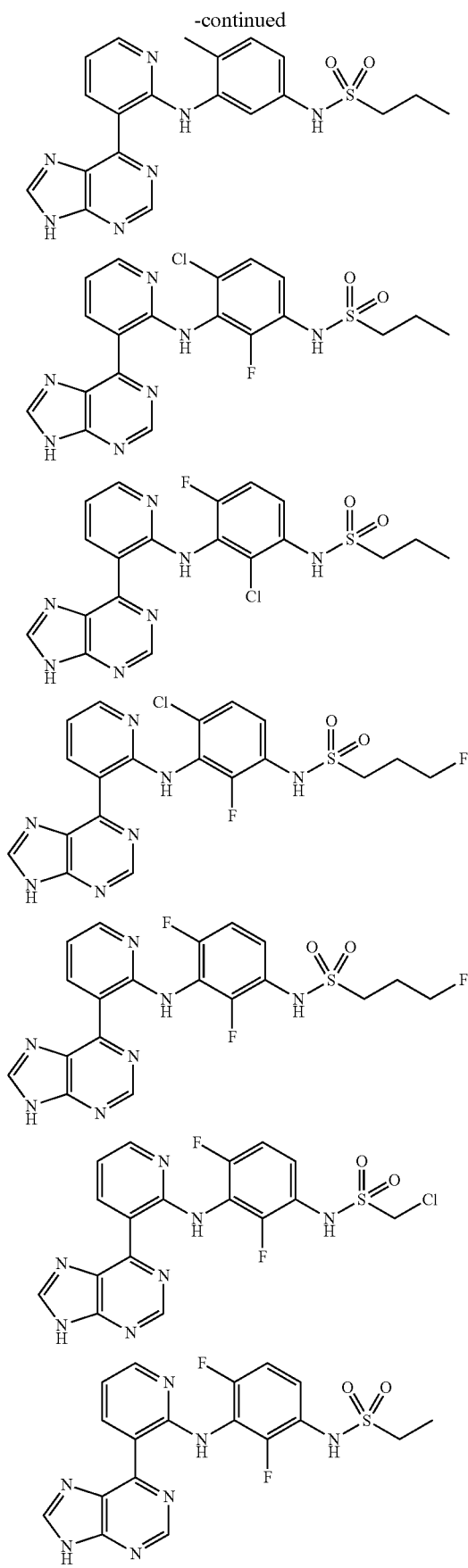
84
-continued
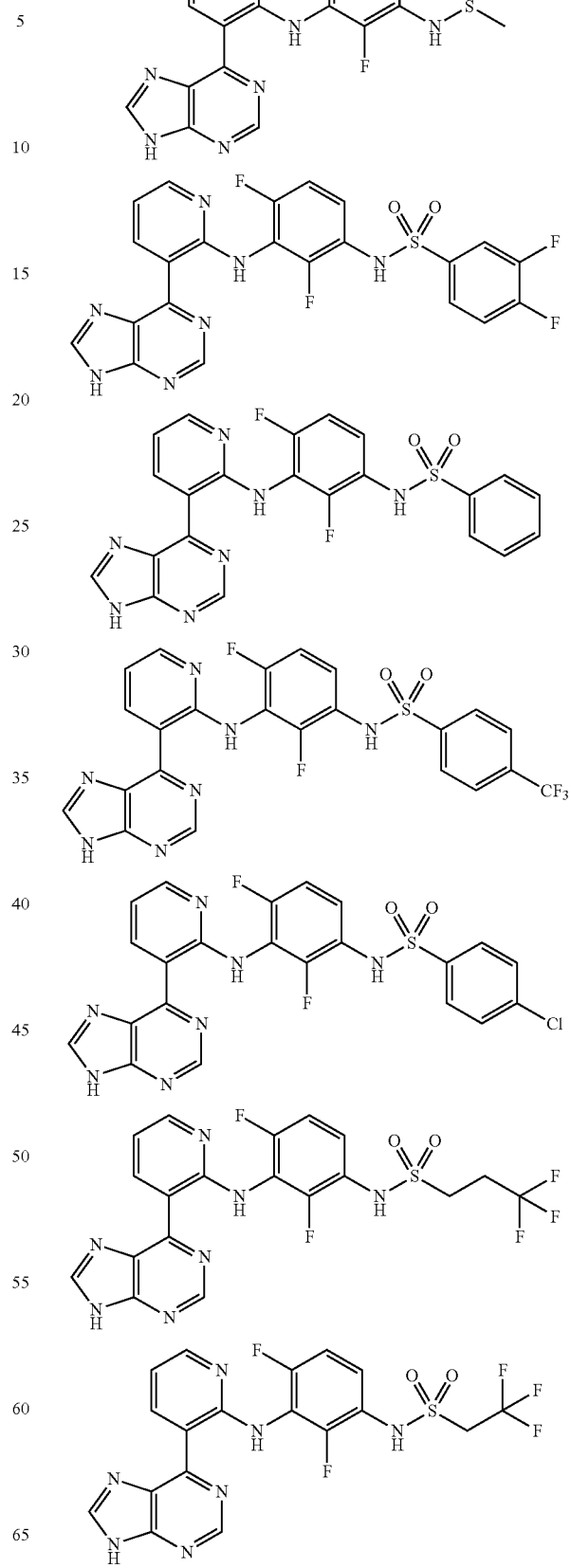

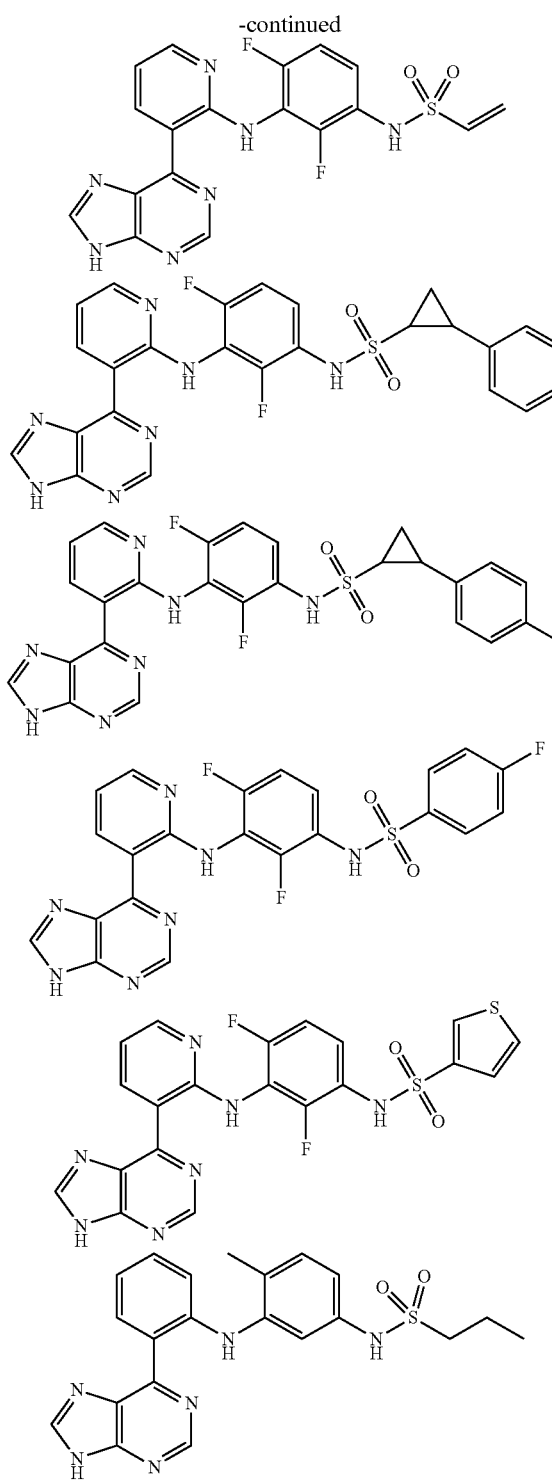
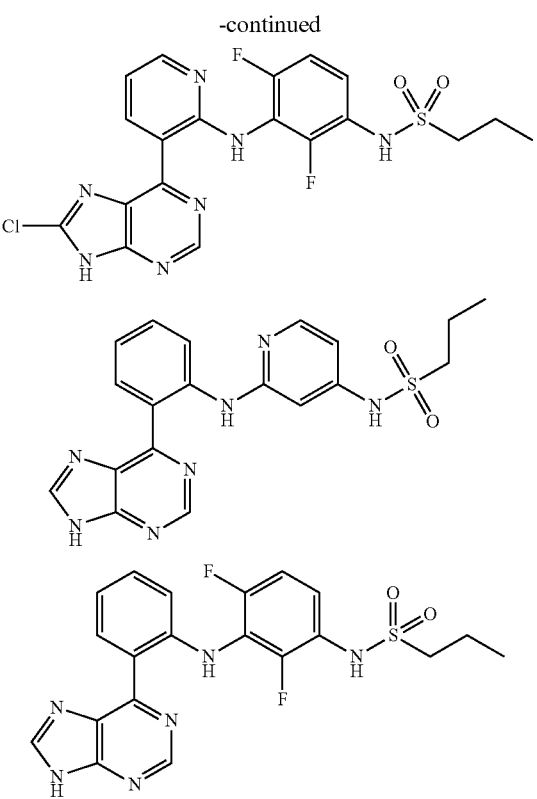

or a pharmaceutically acceptable salt, solvate, polymorph, or tautomer thereof.

10. A pharmaceutical composition comprising at least one compound according to claim 1 and a pharmaceutically acceptable carrier.

11. A method for treating a subject suffering from a protein kinase mediated disease or condition, comprising: administering to said subject an effective amount of the compound of claim 1, wherein said disease or condition is selected from the group consisting of melanoma, lung cancer, and small cell lung cancer.

12. The method according to claim 11, wherein said subject is a mammal.

13. A method for treating a subject suffering from a protein kinase mediated disease or condition, comprising: administering to said subject an effective amount of a pharmaceutical composition according to claim 10, wherein said disease or condition is selected from the group consisting of melanoma, lung cancer, and small cell lung cancer.

14. The method according to claim 12, wherein said subject is a human.

* * * * *